US012679869B2

(12) United States Patent
Burton et al.

(10) Patent No.: US 12,679,869 B2
(45) Date of Patent: Jul. 14, 2026

(54) RECOMBINANT HIV Env POLYPEPTIDES AND THEIR USES

(71) Applicants: International AIDS Vaccine Initiative, New York, NY (US); The Scripps Research Institute, La Jolla, CA (US)

(72) Inventors: Dennis R. Burton, La Jolla, CA (US); Raiees Andrabi, New York, NY (US)

(73) Assignees: INTERNATIONAL AIDS VACCINE INITIATIVE, New York, NY (US); THE SCRIPPS RESEARCH INSTITUTE, La Jolla, CA (US)

( * ) Notice: Subject to any disclaimer, the term of this patent is extended or adjusted under 35 U.S.C. 154(b) by 1154 days.

(21) Appl. No.: 17/299,062

(22) PCT Filed: Dec. 3, 2019

(86) PCT No.: PCT/US2019/064138
§ 371 (c)(1),
(2) Date: Jun. 2, 2021

(87) PCT Pub. No.: WO2020/117740
PCT Pub. Date: Jun. 11, 2020

(65) Prior Publication Data
US 2025/0059238 A1 Feb. 20, 2025

Related U.S. Application Data

(60) Provisional application No. 62/774,693, filed on Dec. 3, 2018.

(51) Int. Cl.
*A61K 39/21* (2006.01)
*A61K 39/00* (2006.01)
*A61K 39/12* (2006.01)
*C07K 14/005* (2006.01)
*C07K 14/155* (2006.01)

(52) U.S. Cl.
CPC ............ *C07K 14/005* (2013.01); *A61K 39/21* (2013.01); *C12N 2740/16122* (2013.01); *C12N 2740/16134* (2013.01)

(58) Field of Classification Search
CPC .. A61K 39/12; A61K 39/21; A61K 2039/575; C07K 14/155; C07K 14/16
See application file for complete search history.

(56) References Cited

FOREIGN PATENT DOCUMENTS

| WO | 2011109511 A2 | 9/2011 |
| WO | 2013039792 A1 | 3/2013 |
| WO | 2014043220 A2 | 3/2014 |
| WO | 2016/037154 A1 | 3/2016 |
| WO | 2017/023857 A1 | 2/2017 |

OTHER PUBLICATIONS

International Search Report for PCT/US2019/064138, mailed Mar. 30, 2020.
Written Opinion of the International Searching Authority for PCT/US2019/064138, dated Jan. 2, 2020.
Third Party Observation submitted in PCT/US2019/064138, dated Apr. 6, 2021.
Rantalainen, K., et al. "Co-Evolution of HIV Envelope and Apex Targeting Neutralizing Antibody Lineage Provides Benchmarks for Vaccine Design," Cell Reports, Jun. 12, 2018.
Stamatatos, L., et al. "Germline-Targeting Immunogens," Immunological Reviews, Jan. 30, 2017.
Crooks, et al., "Glycoengineering HIV-1 Env Creates 'Super-charged' and 'Hybrid' Glycans to Increase Neutralizing Antibody Potency, Breadth and Saturation," PLos Pathogens, May 2, 2018, vol. 14, No. 5.
Voss, et al., "Elicitation of Neutralizing Antibodies Targeting the V2 Apex of the HIV Envelope Trimer in a Wild-Type Animal Model," Cell Reports, Oct. 3, 2017, vol. 21, No. 1, pp. 222-235.
Andrabi et al., Identification of Common Features in Prototype Broadly Neutralizing Antibodies to HIV Envelope V2 Apex to Facilitate Vaccine Design, Immunity, 2015, vol. 43, Issue 5, p. 959-973.
Sanders et al., A Next-Generation Cleaved, Soluble HIV-1 Env Trimer, BG505 SOSIP.664 gp140, Expresses Multiple Epitopes for Broadly Neutralizing but Not Non-Neutralizing Antibodies, PLOS Pathogens, 2013, vol. 9, No. 9, p. e1003618.

*Primary Examiner* — Barry A Chestnut
(74) *Attorney, Agent, or Firm* — Nixon & Vanderhye, PC

(57) ABSTRACT

The present disclosure relates to recombinant HIV Env polypeptides and their use in the treatment and prevention of HIV/AIDS.

19 Claims, 12 Drawing Sheets

Specification includes a Sequence Listing.

A ZM197-ZM233V1V2 SOSIP.664

CRF250-ZM233V1V2 SOSIP.664

BG505-ZM233V1V2 SOSIP.664

B ZM233 virus

A  ELISA binding

V2-immunofocusing: Immunizations with ZM233V1V2 chimeric trimers in CH01
UCA HC-only knock-in mice elicit nAb responses with moderate breadth for
heterologous HIV isolates

GL-CH01 HC/ WT mouse LC

Top: CH01 UCA HC-only knock in mouse model design
Bottom: Immunization schedule of CH01 UCA HC-only KI mice immunized with
ZM233V1V2 chimeric trimers and HIV Env derived trimers.

Figure 5 cont.

V2-immunofocusing: Immunizations with ZM233V1V2 chimeric trimers in CH01 UCA HC-only knock-in mice elicit nAb responses with moderate breadth for heterologous HIV isolates

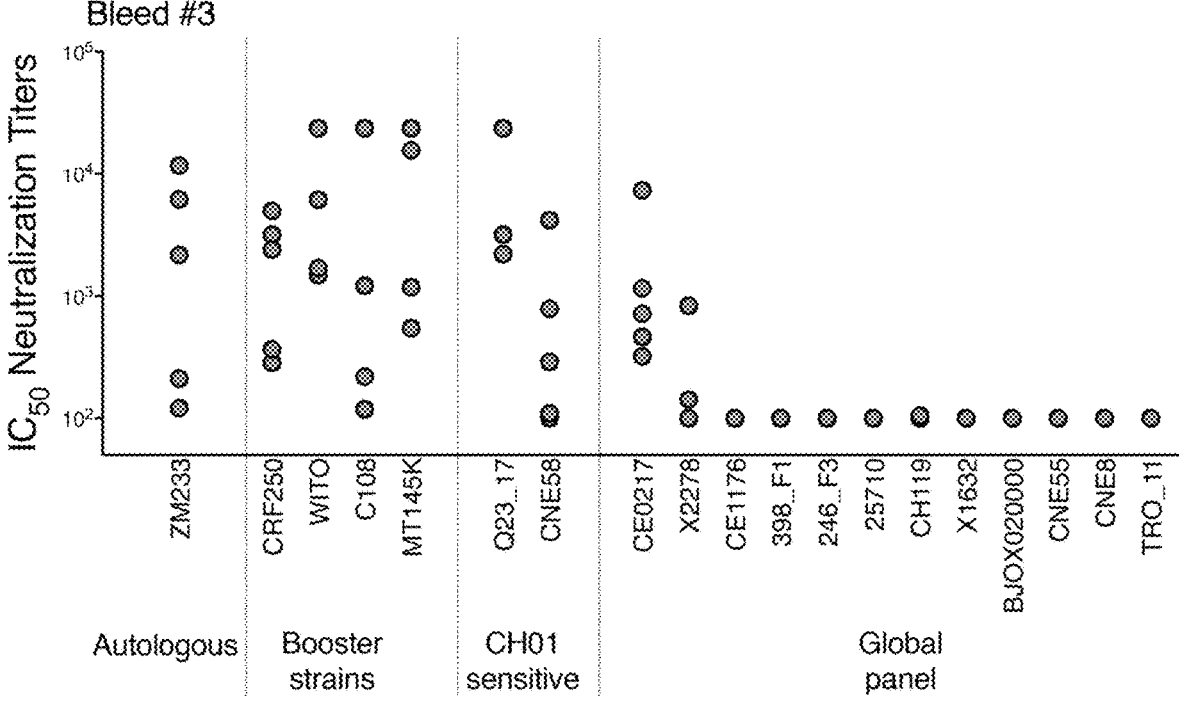

Plot showing $IC_{50}$ Neutralization titers of the Bleed #3 plasma samples (post 2nd boost immunization with 4-trimer cocktail) from 5 CH01 UCA HC-only mice, against the priming immunogen-matched autologous virus, ZM233, booster immunogen-matched, CH01 sensitive, and global panel HIV Env-encoding viruses.

RECOMBINANT HIV Env POLYPEPTIDES AND THEIR USES

CROSS-REFERENCE TO RELATED APPLICATIONS

This application is the U.S. national phase of International Application No. PCT/US2019/064138, filed Dec. 3, 2019, which designated the U.S. and claims the benefit of priority of U.S. Provisional Application No. 62/774,693, filed Dec. 3, 2018, which is herein incorporated herein in its entirety.

REFERENCE TO SEQUENCE LISTING SUBMITTED ELECTRONICALLY

The content of the electronically submitted sequence listing (Name: 6765_0410_Sequence_Listing_21APR2022.txt; Size: 55.2 kilobytes; and Date of Creation: Apr. 21, 2022) is incorporated herein by reference in its entirety.

FIELD OF THE INVENTION

The field of the invention generally relates to recombinant HIV Env polypeptides and their use in the treatment and prevention of HIV/AIDS.

BACKGROUND

Induction of HIV protective broadly neutralizing antibodies (bnAbs), i.e. Abs that neutralize multiple global isolates, will be a key feature of a prophylactic HIV vaccine. BnAbs to HIV envelope (Env) trimer protein are produced over time in a subset of infected donors in natural infection but their elicitation through vaccination has so far proved elusive (reviewed in (Burton and Hangartner, 2016; Escolano et al., 2017; Kwong and Mascola, 2018). A recognized challenge in inducing bnAbs is to design strategies that can guide an immunofocused response to a bnAb epitope and reduce off-target B cell responses.

Thus, there remains a need for immunization strategies that can select rare bnAb precursors, reduce off-target responses and effectively recall epitope-specific B cells at secondary immunization to drive a B cell response towards a desired bnAb epitope.

BRIEF SUMMARY

In one aspect, described herein are engineered or non-naturally occurring HIV Env polypeptides that are missing glycan sequons at N156 and N130 and have one or more basic residues at positions 168 to 171, wherein the HIV Env polypeptides bind to a Human Immunodeficiency Virus (HIV) broadly neutralizing antibody (bnAb), and wherein the HIV Env polypeptide positions correspond to the HXB2 reference (SEQ ID NO: 1).

In one aspect, described herein are engineered or non-naturally occurring HIV Env polypeptides that are missing glycan sequons at N156 and N130 and have one or more basic residues at positions 168 to 171, wherein the HIV Env polypeptides bind to an HIV broadly neutralizing antibody (bnAb) directed to the V2 apex region of HIV envelope, and wherein the HIV Env polypeptide positions correspond to the HXB2 reference.

In one aspect, described herein are engineered or non-naturally occurring HIV Env polypeptides that are missing glycan sequons at N156 and N130 and have one or more basic residues at positions 168 to 171, wherein the HIV Env polypeptides bind to a germline or germline reverted HIV broadly neutralizing antibody (bnAb) directed to the V2 apex region of HIV envelope, and wherein the HIV Env polypeptide positions correspond to the HXB2 reference.

In one aspect, described herein are chimeric HIV Env polypeptides comprising an HIV Env polypeptide backbone and the V1V2 region of the ZM233 HIV Env polypeptide.

In one aspect, described herein are chimeric HIV Env polypeptides comprising an HIV Env polypeptide backbone and the amino acid residues of the ZM233 HIV Env polypeptide corresponding to positions about 131 to about 196, wherein the HIV Env polypeptide positions correspond to the HXB2 reference.

In one aspect, described herein are engineered or non-naturally occurring ZM233 HIV Env polypeptides missing glycan sequons at N156 and N130, wherein the HIV Env polypeptide positions correspond to the HXB2 reference.

In one aspect, described herein are HIV Env polypeptides comprising the amino acid sequence of SEQ ID NO: 6, 7, or 8.

In one aspect, described herein are nucleic acid molecules encoding an HIV Env polypeptide described herein.

In one aspect, described herein are vectors comprising a regulatory element operable in a eukaryotic cell operably linked to a nucleic acid molecule described herein.

In one aspect, described herein are methods of eliciting an immune response in a mammal comprising administering an HIV Env polypeptide described herein, a nucleic acid described herein, or a vector described herein.

In one aspect, described herein are methods of engineering an immunogen capable of eliciting a broadly neutralizing antibody (bnAb) against a V2 epitope of an immunodeficiency virus which comprises a) identifying a V2 epitope conserved across two different HIV viruses, b) selecting or designing an antibody that binds to the epitope, and c) designing an immunogen that comprises the V2 epitope and binds to the germline or germline reverted antibody.

In one aspect, described herein are methods of identifying an HIV binder which comprises contacting a candidate binder with an HIV Env polypeptide described herein and identifying a candidate binder that binds to the HIV Env polypeptide.

In one aspect, described herein are method of identifying a broadly neutralizing antibody (bnAb) against HIV which comprises contacting a candidate antibody with an HIV Env polypeptide described herein and identifying an antibody that binds to the HIV Env polypeptide as a bnAb.

In some embodiments, the disclosure provides:

[1.] An engineered or non-naturally occurring HIV Env polypeptide that is missing glycan sequons at N156 and N130 and has one or more basic residues at positions 168 to 171, wherein the HIV Env polypeptide binds to a Human Immunodeficiency Virus (HIV) broadly neutralizing antibody (bnAb), and wherein the HIV Env polypeptide positions correspond to the HXB2 reference (SEQ ID NO: 1).

[2.] An engineered or non-naturally occurring HIV Env polypeptide that is missing glycan sequons at N156 and N130 and has one or more basic residues at positions 168 to 171, wherein the HIV Env polypeptide binds to an HIV broadly neutralizing antibody (bnAb) directed to the V2 apex region of HIV envelope, and wherein the HIV Env polypeptide positions correspond to the HXB2 reference.

[3.] An engineered or non-naturally occurring HIV Env polypeptide that is missing glycan sequons at N156 and N130 and has one or more basic residues at positions 168 to 171, wherein the HIV Env polypeptide binds to a germline or germline reverted HIV broadly neutralizing antibody (bnAb) directed to the V2 apex region of HIV envelope, and wherein the HIV Env polypeptide positions correspond to the HXB2 reference.

[4.]A chimeric HIV Env polypeptide comprising an HIV Env polypeptide backbone and the V1V2 region of the ZM233 HIV Env polypeptide.

[5.] The chimeric HIV Env polypeptide of [4], wherein the V1V2 region of the ZM233 HIV Env polypeptide comprises the amino acid sequence of SEQ ID NO: 9.

[6.]A chimeric HIV Env polypeptide comprising an HIV Env polypeptide backbone and the amino acid residues of the ZM233 HIV Env polypeptide corresponding to positions about 131 to about 196, wherein the HIV Env polypeptide positions correspond to the HXB2 reference.

[7.] The chimeric HIV Env polypeptide of any one of [4] to [6], wherein the HIV Env polypeptide backbone comprises a BG505, ZM197, or CFR250 backbone.

[8.] The chimeric HIV Env polypeptide of any one of [4] to [7], wherein the HIV Env polypeptide backbone misses glycan sequons at N156 and N130.

[9.] The chimeric HIV Env polypeptide of any one of [4] to [8 that binds to a Human Immunodeficiency Virus (HIV) broadly neutralizing antibody (bnAb).

[10.] The chimeric HIV Env polypeptide of any one of [4] to [8] that binds to an HIV broadly neutralizing antibody (bnAb) directed to the V2 apex region of HIV envelope.

[11.] The chimeric HIV Env polypeptide of any one of [4] to [8] that binds to a germline or germline reverted HIV broadly neutralizing antibody (bnAb) directed to the V2 apex region of HIV envelope.

[12.] An engineered or non-naturally occurring ZM233 HIV Env polypeptide missing glycan sequons at N156 and N130, wherein the HIV Env polypeptide positions correspond to the HXB2 reference.

[13.] The engineered or non-naturally occurring ZM233 HIV Env polypeptide of [12] that binds to a broadly neutralizing antibody (bnAb) directed to the V2 apex region of HIV envelope.

[14.] The engineered or non-naturally occurring ZM233 HIV Env polypeptide of [12] that binds to a germline or germline reverted HIV broadly neutralizing antibody (bnAb) directed to the V2 apex region of HIV envelope.

[15.] The HIV Env polypeptide of any one of [1] to [14], wherein the bnAb is PG9, PG16, CAP256.08, CAP256.09, CH01, CH04, PGT145, or PGDM1400.

[16.] The HIV Env polypeptide of any one of [1] to [14], wherein the germline or germline reverted bnAb is CAP256 UCA, PG9 iGL, CH01 iGL, or PGT145 iGL.

[17.] The HIV Env polypeptide any one of [1] to [14], wherein the germline or germline reverted bnAb is CH01 iGL.

[18.] The HIV Env polypeptide of any one [1] to [17], which comprises a complex of gp120 and gp41.

[19.] The HIV Env polypeptide of any one of [1] to [17], which comprises a stabilized trimer.

[20.] The HIV Env polypeptide of [19], wherein the trimer is a SOSIP, NFL, or UFO trimer.

[21.] The HIV Env polypeptide of any one of [1] to [20], which comprises a V2 apex epitope of ZM233 Env.

[22.] The HIV Env polypeptide of [21], which comprises basic amino acid substitutions at positions 168 to 171, wherein the HIV Env polypeptide positions correspond to the HXB2 reference.

[23.] The HIV Env polypeptide of [21], wherein the V2 apex region of positions 156 to 175 comprises one glycan and four consecutive basic amino acids, wherein the HIV Env polypeptide positions correspond to the HXB2 reference.

[24.] The HIV Env polypeptide of any one of [1] to [23] comprising the amino acid sequence of I-C-$X_1$-F-N-$X_2$-$X_3$-$X_4$-$X_5$-$X_6$-$X_7$-$X_8$-$X_9$-$X_{10}$-$X_{11}$-$X_{12}$-V-N-V-L (SEQ ID NO: 10) at positions 156 to 175, wherein $X_1$ comprises S, T, N, or F; $X_2$ comprises I, V, T, Q, of M; $X_3$ comprises S or T; $X_4$ comprises S or T; $X_5$ comprises S, E, or G; $X_6$ comprises I, L, or V; $X_7$ comprises K or R; $X_8$ comprises G or D; $X_9$ comprises K, R, E, or Q; $X_{10}$ comprises K, R, E, or Q; $X_{11}$ comprises K, R, E, or Q; and $X_{12}$ comprises K, E, or Q.

[25.] The HIV Env polypeptide of [24], wherein at least three of $X_9$, $X_{10}$, $X_{11}$, and $X_{12}$ comprise basic amino acid residues.

[26.] The HIV Env polypeptide of [24], wherein all of $X_9$, $X_{10}$, $X_{11}$, and $X_{12}$ comprise basic amino acid residues.

[27.] The HIV Env polypeptide of [24], wherein $X_9$, $X_{10}$, $X_{11}$, and $X_{12}$ comprise K.

[28.] The HIV Env polypeptide of [21] comprising the amino acid sequence of ICSFNMTTELRDKKRKVNVL (SEQ ID NO: 11) at positions 156 to 175.

[29.] An HIV Env polypeptide comprising the amino acid sequence of SEQ ID NO: 6, 7, or 8.

[30.] The HIV Env polypeptide of any one of [1] to [17], which comprises gp140.

[31.] The HIV Env polypeptide of [19], wherein the trimer comprises gp120-gp41 heterodimers.

[32.] The HIV Env polypeptide of [31], wherein the heterodimers are covalently linked.

[33.] The HIV Env polypeptide of [31], wherein the heterodimers comprise gp120-gp41 fusions proteins.

[34.]A nucleic acid molecule encoding the HIV Env polypeptide of any one of [1] to [33].

[35.]A vector comprising a regulatory element operable in a eukaryotic cell operably linked to the nucleic acid molecule of [34].

[36.] The vector of [35], wherein the vector comprises a viral vector.

[37.] The vector of [36], wherein the vector comprise AAV.

[38.]A method of eliciting an immune response in a mammal comprising administering the HIV Env polypeptide of any one of [1] to [33], the nucleic acid of [34], or the vector of any one of [35] to [37].

[39.] The method of stimulating of a broadly neutralizing HIV antibody (bnAb) in a mammal comprising administering the HIV Env polypeptide of any one of [1] to [33], the nucleic acid of [34], or the vector of any one of [35] to [37].

[40.] The method of [39], which comprises stimulating a germline precursor of a bnAb.

[41.] The method of any one of [38] to [40], wherein the mammal is a human.

[42.] The method of any one of [38] to [40], wherein the mammal is a non-human primate.

[43.] The method of any one of [38] to [40], wherein the mammal is a mouse.

[44.] The method of [43], wherein the mammal comprises elements of a human immune system.

[45.] The method of any one of [38] to [44], wherein the method comprises administering two or more of the HIV Env polypeptide of any one of [1] to [33].

[46.] The method of any one of [38] to [44], wherein the method comprises administering two or more of the HIV Env polypeptide of any one of [1] to [33], each of which comprises a V2 apex epitope of ZM233 trimer.

[47.] The method of [45] or [46], wherein two or more different HIV Env polypeptide are administered.

[48.] The method of any one of [45] to [47], wherein the HIV Env polypeptides are administered sequentially.

[49.] The method of any one of [45] to [48], wherein the HIV Env polypeptides are administered together.

[50.] The method of [38] to [49], wherein the HIV Env polypeptide is administered with an adjuvant.

[51.] The method of [50], wherein the adjuvant comprises a lecithin.

[52.] The method of [51], wherein the lecithin is (a) combined with an acrylic polymer, (b) in a coated oil droplet in an oil-in-water emulsion or (c) in an acrylic polymer in an oil-in-water emulsion.

[53.] The method of [52], wherein the adjuvant is ISCO-MATRIX or Adjuplex.

[54.] The method of [50], wherein the adjuvant comprises alum.

[55.] The method of any one of [38] to [54], wherein the trimer is administered in a liposome or in a nanoparticle.

[56.] The method of any one of [38] to [54], wherein the trimer is fixed.

[57.] The method of [56], wherein the trimer is fixed in glutaraldehyde.

[58.] The method of any one of [38] to [57], wherein the trimer is quenched with glycine.

[59.] The method of any one of [38] to [44], wherein the method comprises administering two or more of the nucleic acid molecule of [34] or two or more of the vector of any one of [35] to [37].

[60.] A method of engineering an immunogen capable of eliciting a broadly neutralizing antibody (bnAb) against a V2 epitope of an immunodeficiency virus which comprises a) identifying a V2 epitope conserved across two different HIV viruses, b) selecting or designing an antibody that binds to the epitope, and c) designing an immunogen that comprises the V2 epitope and binds to the germline or germline reverted antibody.

[61.] The method of [60], wherein the antibody is a germline antibody.

[62.] The method of [60], which comprises engineering the V2 epitope to improve binding of the V2 epitope to the germline or germline reverted antibody.

[63.] The method of [60], wherein designing the immunogen comprises substituting an amino acid in the immunogen.

[64.] A method of identifying an HIV binder which comprises contacting a candidate binder with an HIV Env polypeptide of any one of [1] to [33] and identifying a candidate binder that binds to the HIV Env polypeptide.

[65.] A method of identifying a broadly neutralizing antibody (bnAb) against HIV which comprises contacting a candidate antibody with an HIV Env polypeptide of any one of [1] to [33] and identifying an antibody that binds to the HIV Env polypeptide as a bnAb.

[66.] The method of [65], wherein the bnAb is a germline or germline reverted bnAb.

DETAILED DESCRIPTION

Figure 1:
FIG. 1. Design and characterization of ZM233V1V2 chimeric SOSIP.664 trimer immunogens. Design of ZM233V1V2 chimeric SOSIP.664 trimers. The V1V2 loop sequence derived from ZM233 envelope was engrafted onto three different Env backbones, ZM197 (subtype-C), CRF250 (subtype-AG) and BG505 (subtype-A) and is depicted in maroon. The SOSIP.664 stabilizing modifications include (i) insertion of a disulfide bond between residue 501 (A501C) and 605 (T605C) of gp120 and gp41 subunits, respectively, (ii) replacement of the natural cleavage site between gp120 and gp41 by a furin R6-cleavage site, (iii) gp41 residue I559P substitution, and (iv) truncation at residue 664 of the gp41 subunit. The potential N-glycosylation sites (PNGS) in the gp120 and gp41 subunits of ZM197-ZM233V1V2 SOSIP.664 are labelled and the equivalent glycan positions on the other two SOSIP.664 constructs are aligned unless indicated for unmatched or unique positions. A glycan site at position 332 of the gp120-C3 region (N332-labeled by an asterisk) was introduced into the BG505 backbone. C. Size Exclusion Chromatography (SEC) profiles of PGT145 antibody-affinity purified trimers on Superdex 200 Increase 10/300 GL column. The SEC profiles show the aggregate and trimer peaks. D. SDS-PAGE of chimeric V1V2 trimer proteins under non-reducing (NR) and reducing (R) conditions (dithiothreitol (DTT) was added as reducing agent). The trimers were efficiently cleaved into gp120 and gp41 subunits as indicated. E. Negative Stain Electron-Microscopy (NS-EM) of the trimer; 2D class averages show that the trimers adopt well-ordered, native-like conformations. F. ELISA binding curves of V2-apex bnAbs (mature), their iGL versions, and other bnAbs (PGT121, PGT128, PGT151, VRC01 and PGV04) and non-neutralizing Abs (non-nAbs: F105, 17b, 447-52D and 2557). Dengue specific antibody (DEN3) was used as control.
Figure 1:
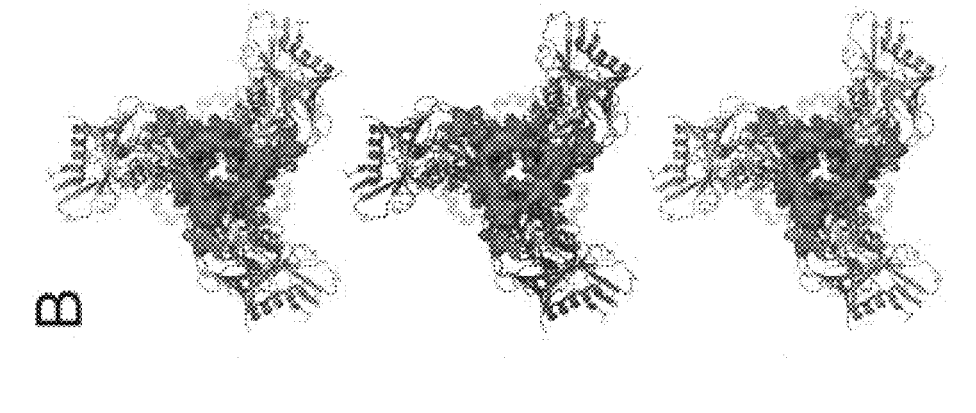
Figure 1:
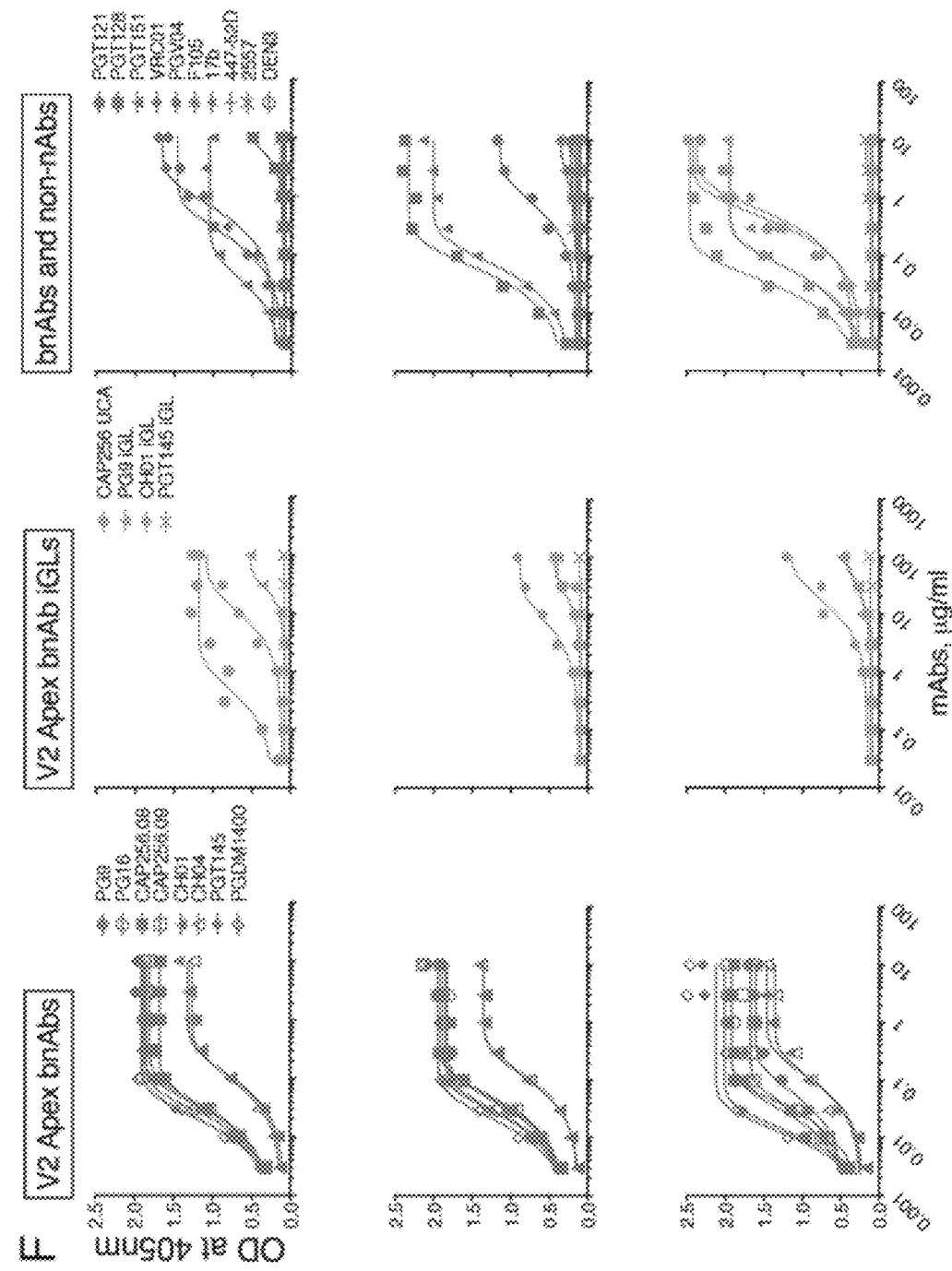

Induction of an HIV envelope (Env) specific broadly neutralizing antibody (bnAb) response will be a key feature of a prophylactic vaccine immunogen. The induction of such Abs will require an immunization strategy capable of focusing responses on to bnAb epitopes in the presence of immunodominant non-desired epitopes. The inventors show herein that immunization with chimeric HIV Env trimers, in which the common V1V2 region was transplanted on to different Env backbones molecules, administered sequentially or as cocktails, produced V2-apex specific neutralizing antibody responses. Thus, the chimeric Env strategy disclosed herein is capable of focusing the immune response to the V2-apex recognized by broadly neutralizing antibodies.

I. Definitions

To facilitate an understanding of the present invention, a number of terms and phrases are defined below.

The terms "human immunodeficiency virus" or "HIV," as used herein, refer generally to a retrovirus that is the causative agent for acquired immunodeficiency syndrome (AIDS), variants thereof (e.g., simian acquired immunodeficiency syndrome, SAIDS), and diseases, conditions, or opportunistic infections associated with AIDS or its variants, and includes HIV-Type 1 (HIV-1) and HIV-Type 2 (HIV-2) of any clade or strain therein, related retroviruses (e.g., simian immunodeficiency virus (SIV)), and variants thereof (e.g., engineered retroviruses, e.g., chimeric HIV viruses, e.g., simian-human immunodeficiency viruses (SHIVs)). In some embodiments, an HIV virus is an HIV-Type-1 virus. Previous names for HIV include human T-lymphotropic virus-Ill (HTLV-III), lymphadenopathy-associated virus (LAV), and AIDS-associated retrovirus (ARV).

Acquired immune deficiency syndrome ("AIDS") is a disease caused by the human immunodeficiency virus, or HIV.

As used herein, the term "envelope glycoprotein" or "Env" refers to the glycoprotein that is expressed on the surface of the envelope of HIV virions and the surface of the plasma membrane of HIV infected cells. "Envelope glycoprotein" or "Env" encompass, but are not limited to, native Env, an isoform of Env, or a recombinant variant of Env (e.g., SOSIP) derived from an HIV isolate. Env is the sole virally encoded gene product on the surface of the virus and, as such, is the only target of neutralizing antibodies. Env is a trimer of heterodimers composed of two non-covalently associated subunits: the receptor-binding gp120 and the fusion machinery-containing gp41. Each subunit is derived from a gp160 precursor glycoprotein following cleavage by cellular furins. HIV-1 gp120 binds the CD4 molecule on the surface of human target T cells to initiate the viral entry process, and following co-receptor engagement, fusion is mediated by gp41. gp140 env is the uncleaved ectodomain of gp160. In some embodiments, Env is a BG505, ZN233, ZM197, or CFR250 Env polypeptide. In some embodiments, the Env is a BG505 Env polypeptide. UniProtKB accession number Q2NOS5-1, Q2NOS6-1, and Q2NOS7-1 provide BG505 env gp160 polypeptide sequences. In some embodiments, the Env is a BG505 Env polypeptide comprising the amino acid sequence of SEQ ID NO: 2. In some embodiments, the Env is a ZM197 Env polypeptide comprising the amino acid sequence of SEQ ID NO: 3. In some embodiments, the Env is a CFR250 Env polypeptide comprising the amino acid sequence of SEQ ID NO: 4. In some embodiments, the Env is a ZM233 Env polypeptide comprising the amino acid sequence of SEQ ID NO: 5. In some embodiments, the Env is a well-ordered Env trimer.

The ectodomain of HIV Env comprises 5 variable domain loops: V1, V2, V3, V4, V5 loops. The position of the loops is determined using the HXB2 Env polypeptide (SEQ ID NO: 1) as a reference. In some embodiments, the V1 loop includes positions 131-157 in HXB2, and is bounded by a disulfide bond in the Cysteines at the base (C). In some embodiments, the V2 region begins where V1 ends, starting at S158 and continuing through C196 in HXB2. In some embodiments, the V1V2 region of HIV Env comprises positions starting at 125-135 and ending at positions 191-200, wherein the positions correspond to the HXB2 reference (SEQ ID NO: 1). In some embodiments, the V1V2 region of HIV Env comprises positions starting at about 131 and ending at about 196, wherein the positions correspond to the HXB2 reference (SEQ ID NO: 1). In some embodiments, the V1V2 region of HIV Env comprises positions starting at about 137 and ending at about 197, wherein the positions correspond to the HXB2 reference (SEQ ID NO: 1).

The term "chimeric Env polypeptide" refers to Env polypeptides wherein the amino acid sequence is derived from two or more HIV isolates. In some embodiments, a chimeric Env polypeptide comprises a backbone from one HIV isolate, and a V1V2 region from a second isolate. In some embodiments, a chimeric Env polypeptide comprises a backbone from one HIV isolate, and a V2 region from a second isolate.

The term "well-ordered Env trimer" or "well-ordered trimer" as used herein refers to an envelope glycoprotein trimer comprising three cleaved gp140 polypeptides that closely mimic the quaternary structure of the Env ectodomain on the surface of the envelope of HIV or SIV virions and the surface of the plasma membrane of HIV or SIV infected cells. In one embodiment, the gp140 polypeptides comprise MPER. In one embodiment, the well-ordered trimer comprises three MPERs. In one embodiment, the gp120 and gp41 ectodomain is linked by a covalent linkage, for example, a disulfide bond. In one embodiment, the gp140 polypeptide comprises one or more mutations to promote trimer formation. In one embodiment, the gp140 polypeptide comprises one or more Cys substitutions to promote disulfide formation. In one embodiment, the well-ordered trimer is a SOSIP gp140 trimer. Well-ordered SOSIP trimers have been disclosed in US Patent Appl. Pub. No. 2014/0212458, and Sanders, R. W. et al., PLoS Pathog. 9, e1003618 (2013), each of which is incorporated by reference herein in its entirety. In one embodiment, a well-ordered trimer is formed from a clade A Env. In one embodiment, a well-ordered trimer is formed from a clade B Env. In one embodiment, a well-ordered trimer is formed from a clade C Env. In one embodiment, a well-ordered trimer is formed from a circulating recombinant form Env, wherein 'circulating recombinant form' (CRF) refers to a hybrid virus comprising a combination of genetic material from different subtypes. In one embodiment, a well-ordered trimer is Du156.12 SOSIP comprising MPER. In one embodiment, a well-ordered Env trimer is a native flexibly linked (NFL) trimer as described in Sharma, et al., Cell Reports, 11(4):539-50 (2015). In one embodiment, a well-ordered Env trimer is a DS-SOSIP as described in Chuang G Y, et al., J. Virology, 91(10). pii: e02268-16 (2017). In one embodiment, a well-ordered trimer is formed from an SIV Env. In one embodiment, a well-ordered trimer is an SIV Env SOSIP. In one embodiment, a well-ordered trimer is formed from an Env comprising a mutation (e.g., substitution or deletion) in the CD4 binding site. In one embodiment, a well-ordered trimer is formed from an Env comprising a mutation (e.g., substitution or deletion) in the CD4 binding site wherein the mutation reduces or disrupts the binding between Env and CD4. In one embodiment, a well-ordered trimer is a CRF or C108 SOSIP. See, e.g., Andrabi R., et al, Immunity 43(5): 959-973 (2015). In some embodiments, the gp120 and gp41 ectodomain is linked by a peptide linker, for example, a Gly-Ser linker, as described in Georgiev I S, et al., J. Virology 89(10): 5318-5329 (2015). In some embodiments, the well-ordered Env trimer is stable.

The term "antibody" means an immunoglobulin molecule (or a group of immunoglobulin molecules) that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), affybodies, Fab fragments, F(ab')$_2$ fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclasses (isotypes) thereof (e.g. IgG1, IgG2, IgG3, IgG4, IgA1 and IgA2), of immunoglobulin molecule, based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated or fused to other molecules such as toxins, radioisotopes, other polypeptides etc.

As used herein, the terms "antigen-binding domain," "antigen-binding region," "antigen-binding site," and similar terms refer to the portion of antibody molecules, which comprises the amino acid residues that confer on the antibody molecule its specificity for the antigen (e.g., HIV Env MPER). The antigen-binding region can be derived from any animal species, such as mouse and humans.

As used herein, the terms "variable region" or "variable domain" are used interchangeably and are common in the art. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen (e.g., HIV Env MPER). In certain embodiments, the variable region comprises 3 CDRs (CDR1, CDR2, and CDR3) and 4 framework regions (FR1, FR2, FR3, and FR4) in the order of FR1-CDR1-FR2-CDR2-FR3-CDR3-FR4 from the N terminus to the C terminus. In certain embodiments, the variable region is a human variable region. In certain embodiments, the variable region comprises human CDRs and human framework regions (FRs). In certain embodiments, the variable region comprises CDRs and framework regions (FRs) wherein one or more of the CDRs were modified by a substitution, deletion, or insertion relative to the CDRs of a parental antibody. In certain embodiments, the variable region comprises CDRs and framework regions (FRs) wherein one or more of the FRs were modified by a substitution, deletion, or insertion relative to the FRs of a parental antibody. In certain embodiments, the variable region comprises CDRs and framework regions (FRs) wherein one or more of the CDRs and one or more of the FRs were modified by a substitution, deletion, or insertion relative to the CDRs and FRs of a parental antibody. In certain embodiments, the parental antibody is PGZL1. In certain embodiments, the variable region comprises human CDRs and primate (e.g., non-human primate) framework regions (FRs).

A skilled artisan understands that there are several methods for determining CDRs. One approach is based on cross-species sequence variability (i.e., Kabat E A, et al., Sequences of Proteins of Immunological Interest, (5th ed., 1991, National Institutes of Health, Bethesda Md.) ("Kabat"). Another approach is based on crystallographic studies of antigen-antibody complexes (Al-lazikani B., et al, J. Mol. Biol. 273:927-948 (1997)) ("Chothia"). In addition, combinations of these two approaches are sometimes used in the art to determine CDRs. In some embodiments, the CDR sequences are identified according to Kabat. In some embodiments, the CDR sequences are identified according to Chothia. It is understood that the identification of CDRs in a variable region also identifies the FRs as the sequences flanking the CDRs.

The Kabat numbering system is generally used when referring to a residue in the variable domain (approximately residues 1-107 of the light chain and residues 1-113 of the heavy chain) (e.g., Kabat E A, et al., Sequences of Immunological Interest. (5th Ed., 1991, National Institutes of Health, Bethesda, Md.) ("Kabat").

The terms "VL" and "VL domain" are used interchangeably to refer to the light chain variable region of an antibody.

The terms "VH" and "VH domain" are used interchangeably to refer to the heavy chain variable region of an antibody.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')$_2$, and Fv fragments, linear antibodies, and single chain antibodies.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Or better" when used herein to refer to binding affinity refers to a stronger binding between a molecule and its binding partner. "Or better" when used herein refers to a stronger binding, represented by a smaller numerical $K_D$ value. For example, an antibody, which has an affinity for an antigen of "0.6 nM or better", the antibody's affinity for the antigen is <0.6 nM, i.e. 0.59 nM, 0.58 nM, 0.57 nM etc. or any value less than 0.6 nM.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), ELISA, biolayer interferometry (BLI), flow cytometry or other assays known in the art. In a specific embodiment, molecules that immunospecifically bind to an antigen bind to the antigen with a $K_D$ that is at least 2 logs, 2.5 logs, 3 logs, or 4 logs lower than the $K_D$ when the molecules bind nonspecifically to another antigen. In one example, the antibody may specifically bind to cells that express functional, well-ordered HIV-1 membrane Env trimers. In one example, the antibody may specifically bind to Env trimers from detergent-solubilized HIV-1 virions. In one example, the antibody may specifically bind to Env trimers from detergent-solubilized HIV-1 virions in an ELISA assay. In one example, the antibody may specifically bind to Env trimers from detergent-solubilized HIV-1 virions in a BN-PAGE gel mobility-shift assay. The antibody may bind to an HIV Env polypeptide described herein with a $K_D$ at least 2 logs, 2.5 logs, 3 logs, or 4 logs lower than $K_D$ of binding to other viral or non-viral polypeptides. An antibody that specifically binds to Env encompass, but are not limited to, antibodies that specifically bind to native Env, an isoform of Env, or a variant of Env (e.g., SOSIP) derived from an HIV isolate. In some embodiments, the antibody is a broadly neutralizing antibody. In some embodiments, the antibody is a broadly neutralizing antibody (bnAb) directed to the V2 apex region of HIV envelope. In some embodiments, the antibody is a germline or germline reverted HIV broadly neutralizing antibody (bnAb) directed to the V2 apex region of HIV envelope. In some embodiments, the broadly neutralizing antibody is PG9, PG16, CAP256.08, CAP256.09, CH01, CH04, PGT145, or PGDM1400. See, e.g., Walker L. et al. Science. 326:285-9 (2009); U.S. Pat. No. 9,464,131; U.S. Pat. Appl. Pub. No. 20150361160, each of which is incorporated herein by reference in its entirety for all purposes. In some embodiments, the germline or germline reverted broadly neutralizing antibody (bnAb) is CAP256 UCA, PG9 iGL, CH01 iGL, or PGT145 iGL.

By "preferentially binds," it is meant that the antibody specifically binds to an epitope more readily than it would bind to a related, similar, homologous, or analogous epitope. Thus, an antibody, which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "broadly neutralizing antibody" or "bnAb," as used herein, with respect to HIV (e.g., HIV-1), refers to an antibody that recognizes HIV Env of more than one isolate or strain of HIV and inhibits or prevents receptor binding of target cells as evaluated in an in vitro neutralization assay. In one embodiment, a broadly neutralizing antibody inhibits infection of a susceptible target cell by HIV. In one embodiment, a broadly neutralizing antibody specifically binds an HIV Env and inhibits infection of a susceptible target cell (e.g., TZM-bl) by an HIV pseudovirus comprising an Env polypeptide. HIV pseudovirus neutralization assays have been disclosed in the art, for example, in Walker L. M., et al., Nature 477, 466-470 (2011), Li M., et al., J. Virol. 79:10108-10125 (2005), each of which is incorporated herein by reference in its entirety for all purposes. In one embodiment, a broadly neutralizing antibody neutralizes 2, 3, 4, 5, 6, 7, 8, 9, or more HIV strains or pseudoviruses. In one embodiment, a broadly neutralizing antibody neutralizes 2, 3, 4, 5, 6, 7, 8, 9, or more HIV strains or pseudoviruses that belong to the same or different clades. In one embodiment, a broadly neutralizing antibody is capable of neutralizing HIV strains or pseudoviruses from at least two different clades. In one embodiment, a broadly neutralizing antibody is capable of neutralizing at least one clade B strain or pseudovirus and one clade C strain or pseudovirus. In one embodiment, a broadly neutralizing antibody is capable of neutralizing more than one clade B strain or pseudovirus and more than one clade C strain or pseudovirus. In one embodiment, a broadly neutralizing antibody is capable of neutralizing an HIV strain or pseudovirus from at least one, at least two, at least three, at least four, at least five, at least six, at least seven, at least eight, at least nine, at least ten, or at least eleven clades represented in the 130-member indicator virus panel. In one embodiment, a broadly neutralizing antibody is capable of neutralizing an HIV strain or pseudovirus from at least one, at least two, at least three, at least four, at least five, at least six, at least seven, at least eight, at least nine, at least ten, at least eleven, at least twelve, at least thirteen, at least fourteen, or all fifteen clades selected from the group consisting of clades A, A (T/F), AC, ACD, B, B (T/F), BC, C, C (T/F), CD, CRF01_AE, CRF01_AE (T/F), CRF02_AG, D, and G. In one embodiment, a broadly neutralizing antibody is capable of neutralizing an HIV strain or pseudovirus from at least one, at least two, at least three, at least four, at least five, at least six, at least seven, at least eight, at least nine, at least ten, or all eleven clades selected from the group consisting of clades A, AC, ACD, AE, AG, B, BC, C, CD, D, G. In some embodiments, the broadly neutralizing antibody is PG9, PG16, CAP256.08, CAP256.09, CH01, CH04, PGT145, or PGDM1400. See, e.g., Walker L. et al. Science. 326:285-9 (2009); U.S. Pat. No. 9,464,131; U.S. Pat. Appl. Pub. No. 20150361160, each of which is incorporated herein by reference in its entirety for all purposes.

In one embodiment, the breadth of neutralization is tested on an indicator virus panel comprising cross-clade HIV isolates. In one embodiment, the virus panel comprises the 9 cross-clade isolates of 92TH021, JRCSF, C22, 94UG103, 92BR020, Du156.12, HIV-2, HIV-2C1, and HIV-2C4. In one embodiment, the virus panel comprises the 130 cross-clade isolates of NIH-065_191955 All, NIH-063_0330.v4.c3, NIH-066_191084 B7.19, NAC_BG505, NIH-057_MS208. A1, NIH-064_0260.v5.c1, NAC_KNH1144, NAC_94UG103, NAC_92RW020, NIH-060_Q769ENVd22, NIH-058_Q23ENV17, NIH-056_Q168ENVa2, NIH-061_Q259ENVd2.17, NIH-059_Q461ENVe2, NIH-117_T278.5, NIH-100_6041.v3.c23, NIH-099_3301.v1.c24, NIH-102_6545.v4.c1, NIH-101_6540.v4.c1, NIH-103_0815.v3.c3, NIH-104_3103.v3.c10, NIH-073_C3347.c11, NIH-080_BJOX025000.01.1, NIH-075_CNE8, NAC_92TH021, NIH-081_BJOX028000.10.3, NIH-078_BJOX015000.11.5, NIH-079_BJOX010000.06.2, NIH-074_C4118.c09, NIH-069_C1080.c03, NIH-077_BJOX009000.02.4, NIH-068_620345.c01, NIH-076_CNE5, NIH-070_R2184.c04, NIH-072_R3265.c06, NIH-071_R1166.c01, NIH-115_928.28, NIH-118_T255.34, NIH-116_T263.8, NIH-108_T235.47, NIH-114_T257.31, NIH-107_T251.18, NIH-106_T250.4, NIH-119_T211.9, NAC_MN, NAC_HxB2, NIH-012_1012.11. TC21.3257, NAC_ADA, NAC_WITO.33, NIH-006_AC10.0.29, NIH-003_SC422661.8, NAC_89.6, NAC_BaL.26, NAC_RHPA4.7, NIH-014_6244.13. B5.4567, NAC_TRJO.58, NAC_92BR020, NIH-008_WE-AU.d15.410.787, NAC_REJO.67, NIH-009_1006.11. C3.1601, NAC_SS1196.1, NAC_YU2, NAC_JRCSF, NAC_JRFL, NIH-004_PVO.4, NAC_DH12, NIH-005_TRO.11, NAC_SF162, NIH-011_1056.10. TA11.1826, NIH-016_SC05.8C11.2344, NIH-013_6240.08. TA5.4622, NIH-007_CAAN5342. A2, NIH-010_1054.07. TC4.1499, NIH-001_6535.3, NIH-015_62357.14. D3.4589, NIH-002_QH0692 0.42, NIH-050_CNE21, NIH-054_CNE53, NIH-055_CNE58, NIH-048_CNE19, NIH-053_CNE52, NIH-051_CNE17, NIH-052_CNE30, NIH-049_CNE20, NIH-030_HIV-0013095.2.11, NIH-026_ZM135M.PL10a, NIH-017_Du156.12, NIH-019_Du422.1, NIH-018_Du172.17, NIH-032_HIV-16845.2.22, NIH-039_Ce2060 G9, NAC_93IN905, NIH-029_HIV-001428.2.42, NIH-041_BF1266.431a, NIH-023_ZM249M.PL1, NIH-031_HIV-16055.2.3, NIH-043_ZM249M. B10, NIH-025_ZM109F.PB4, NIH-040_Ce703010054 2A2, NIH-036_Ce2010 F5, NIH-020_ZM197M.PB7, NIH-044_ZM247F.F7, NIH-046_1394C9G1(Rev.), NIH-047_Ce704809221 1B3, NAC_IAVIC22, NIH-034_Ce0393 C3, NIH-045_7030102001E5(Rev.), NIH-021_ZM214M.PL15, NIH-024_ZM53M.PB12, NIH-035_Ce1176 A3, NIH-022_ZM233M.PB6, NIH-027_CAP45. G3, NIH-042_ZM246F. D5, NHI-028_CAP210. E8, NIH-038_Ce1172 H1, NIH-095_6480.v4.c25, NIH-096_6952.v1.c20, NIH-097_6811.v7.c18, NIH-094_3817.v2.c59, NIH-098_89. F1 2 25, NIH-089_3016.v5.c45, NIH-090_A07412M1.vrc12, NIH-091_231965.c01, NIH-086_X2131 C1 B5, NIH-082_X1193 c1, NIH-084_X1254 c3, NIH-083_P0402 c2 11, NIH-087_P1981 C5 3, NIH-088_X1632 S2 B10, and NIH-085_X2088 c9. In one embodiment, a broadly neutralizing antibody is capable of neutralizing at least 4, 5, 6, 7, 8 or 9 of the cross-clade HIV isolates in the 9-member indicator virus panel. In one embodiment, a broadly neutralizing antibody is capable of neutralizing at least 6 of the cross-clade HIV isolates in the 9-member indicator virus panel. In one embodiment, a broadly neutralizing antibody is capable of neutralizing at least about 50%, 60%, 70%, 80%, 90%, 95%, or 100% of cross-clade HIV isolates in the 130-member indicator virus panel. In one embodiment, a broadly neutralizing antibody is capable of neutralizing at least about 60% of cross-clade HIV isolates in the 130-member indicator virus panel. In one embodiment, a broadly neutralizing antibody is capable of neutralizing at least about 70% of cross-clade HIV isolates in the 130-member indicator virus panel. In one embodiment, a broadly neutralizing antibody is capable of neutralizing at least about 75% of cross-clade HIV isolates in the 130-member indicator virus panel. In one embodiment, a broadly neutralizing antibody is capable of neutralizing at least about 80% of cross-clade HIV isolates in the 130-member indicator virus panel. In one embodiment, a broadly neutralizing antibody is capable of neutralizing at least about 90% of cross-clade HIV isolates in the 130-member indicator virus panel. In one embodiment, a broadly neutralizing antibody is capable of neutralizing at least about 95% of cross-clade HIV isolates in the 130-member indicator virus panel. In one embodiment, a broadly neutralizing antibody is capable of neutralizing at least about 98% of cross-clade HIV isolates in the 130-member indicator virus panel. In one embodiment, a broadly neutralizing antibody is capable of neutralizing at least about 100% of cross-clade HIV isolates in the 130-member indicator virus panel.

The phrase "substantially similar," or "substantially the same", as used herein, denotes a sufficiently high degree of similarity between two numeric values (generally one associated with an antibody described herein and the other associated with a reference/comparator antibody) such that one of skill in the art would consider the difference between the two values to be of little or no biological and/or statistical significance within the context of the biological characteristic measured by said values (e.g., $K_D$ values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition, which is "isolated" is a polypeptide, antibody, polynucleotide, vector, cell, or composition, which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition, which is isolated is substantially pure.

As used herein, "substantially pure" refers to material, which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides described herein are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin S., et al, Proc. Natl. Acad. Sci., 87:2264-2268 (1990), as modified in Karlin S., et al., Proc. Natl. Acad. Sci., 90:5873-5877 (1993), and incorporated into the NBLAST and XBLAST programs (Altschul S F, et al., Nucleic Acids Res., 25:3389-3402 (1991)). In certain embodiments, Gapped BLAST can be used as described in Altschul S F, et al., Nucleic Acids Res. 25:3389-3402 (1997). BLAST-2, WU-BLAST-2 (Altschul S F, et al., Methods in Enzymology, 266:460-480 (1996)), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna. CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman (Advances in Applied Mathematics 2: 482 489 (1981)) to find the best segment of homology between two sequences. When using Bestfit or any other sequence alignment program to determine whether a particular sequence is, for instance, 95% identical to a reference sequence described herein, the parameters are set such that the percentage of identity is calculated over the full length of the reference nucleotide sequence and that gaps in identity of up to 5% of the total number of nucleotides in the reference sequence are allowed.

In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies described herein do not abrogate the binding of the polypeptide or antibody containing the amino acid sequence, to the antigen(s). Methods of identifying nucleotide and amino acid conservative substitutions, which do not eliminate antigen binding are well-known in the art (see, e.g., Brummell D A, et al., Biochem. 32: 1180-1 187 (1993); Kobayashi et al., Protein Eng. 12(10):879-884 (1999); and Burks E A, et al., Proc. Natl. Acad. Sci. USA 94: 412-417 (1997)).

As used herein, the terms "treatment" or "therapy" (as well as different forms thereof, including curative or palliative) refer to treatment of an infected person. As used herein, the term "treating" includes alleviating or reducing at least one adverse or negative effect or symptom of a condition, disease or disorder. This condition, disease or disorder can be HIV infection.

Terms such as "treating" or "treatment" or "to treat" or "alleviating" or "to alleviate" refer to therapeutic measures that cure, slow down, lessen symptoms of, and/or halt progression of a diagnosed pathologic condition or disorder, such as HIV or AIDS. Thus, those in need of treatment include those already diagnosed with or suspected of having the disorder. In certain embodiments, a subject is successfully "treated" for the disorder according to the methods described herein if the patient shows one or more of the following: a reduction in the number of or complete absence of viral load; a reduction in the viral burden; inhibition of or an absence of the virus into peripheral organs; relief of one or more symptoms associated with the disorder; reduced morbidity and mortality; improvement in quality of life; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

As used herein, the terms "prevention" or "prophylaxis" refer to preventing a subject from becoming infected with, or reducing the risk of a subject from becoming infected with, or halting transmission of, or the reducing the risk of transmission of a virus. Prophylactic or preventative measures refer to measures that prevent and/or slow the development of a targeted pathological condition or disorder. Thus, those in need of prophylactic or preventative measures include those prone to have the disorder and those in whom the disorder is to be prevented. In one embodiment, prevention encompasses passive immunization of a subject in need thereof comprising administering an effective amount of an antibody described herein.

As employed above and throughout the disclosure the term "effective amount" refers to an amount effective, at dosages, and for periods of time necessary, to achieve the desired result with respect to the treatment of the relevant disorder, condition, or side effect. An "effective amount" can be determined empirically and in a routine manner, in relation to the stated purpose. It will be appreciated that the effective amount of components of the present invention will vary from patient to patient not only with the particular vaccine, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors, which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

The term "therapeutically effective amount" refers to an amount of an antibody, recombinant virus, immunoconjugate, or other drug effective to "treat" a disease or disorder in a subject or mammal. To the extent an antibody can prevent growth and/or kill existing cells, it can be cytostatic and/or cytotoxic. A "prophylactically effective amount" refers to an amount effective, at dosages and for periods of time necessary, to achieve the desired prophylactic result.

Typically but not necessarily, since a prophylactic dose is used in subjects prior to or at an earlier stage of disease, the prophylactically effective amount will be less than the therapeutically effective amount.

The terms "subject," "individual," and "patient" are used interchangeably herein, and refer to an animal, for example a human, to whom treatment, including prophylactic treatment, with the antibody or pharmaceutical composition according to the present disclosure, is provided. In one embodiment, the subject, individual, or patient has been infected with HIV. In one embodiment, the subject, individual, or patient suffers from AIDS. In one embodiment, the subject, individual, or patient has been exposed to HIV. In one embodiment, the subject, individual, or patient is at risk of being exposed to HIV.

Administration "in combination with" one or more further therapeutic agents includes simultaneous (concurrent) or consecutive administration in any order.

The terms "pharmaceutically composition," "pharmaceutical formulation," "pharmaceutically acceptable formulation," or "pharmaceutically acceptable composition" all of which are used interchangeably, refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. "Pharmaceutically acceptable" or "pharmaceutical formulation" refers to a preparation, which is in such form as to permit the biological activity of the active ingredient to be effective, and which contains no additional components, which are unacceptably toxic to a subject to which the formulation would be administered. The formulation can be sterile.

The term "antiretroviral therapy" or "ART," as used herein, refers to any of the therapies used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include, but are not limited to, lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine (ETR), delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir (RTV), darunavir (DRV), atazanavir sulfate (ATV), nelfinavir mesylate (NFV), enfuvirtide (T-20), maraviroc and raltegravir. ART drugs can also include antibodies that target HIV proteins or cellular proteins associated with disease progression. Also included are immune-based therapies, such as IL-2, IL-12, and alpha-epibromide. Each of these drugs can be administered alone or in combination with any other ART drug or any HIV-specific neutralizing antibody, such as a broadly neutralizing antibody, which is incorporated by reference herein in its entirety for all purposes.

The term "reservoir activator," as used herein, refers to an agent capable of activating a viral reservoir (e.g., an HIV reservoir). In one embodiment, a reservoir activator comprises a histone deacytelase (HDAC) inhibitor (e.g., romidepsin, vorinostat, and panobinostat), immunologic activator (e.g., cytokines and TLR agonists), or a dedicated small molecule drug.

The term "immunomodulator," as used herein, refers to an agent, such as an antibody or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Immunomodulators include, but are not limited to immune checkpoint inhibitors, for example, a PD-1, PD-L1, LAG-3, or TIGIT antagonist. In one embodiment, an immunomodulator used in the methods described herein comprises an anti-PD-1 antibody, anti-PD-L1 antibody, anti-LAG3 antibody, or an anti-TIGIT antibody. An immunomodulator can be administered in conjunction with (e.g., prior to, concurrently with, or subsequent to, or within the context of a treatment regimen that includes the administration of a broadly neutralizing antibody described herein.

As used in this specification and the appended claims, the singular forms "a," "an," and "the" include plural referents unless the content clearly dictates otherwise. Thus, for example, reference to "a cell" includes a combination of two or more cells, and the like.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein when referring to a measurable value such as an amount, a temporal duration, and the like, is meant to encompass variations of up to ±20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope described herein are approximations, the numerical values set forth in the specific examples are reported as precisely as possible. Any numerical value, however, inherently contain certain errors necessarily resulting from the standard deviation found in their respective testing measurements.

It is understood that wherever embodiments are described herein with the language "comprising," otherwise analogous embodiments described in terms of "consisting of" and/or "consisting essentially of" are also provided.

II. Polypeptides

In one aspect, provided herein are isolated polypeptides derived from an HIV Env polypeptide. In some embodiments, an isolated polypeptide described herein comprises a variant gp160 polypeptide. In some embodiments, an isolated polypeptide described herein comprises a variant gp140 polypeptide. In some embodiments, an isolated polypeptide described herein comprises a variant gp120 polypeptide. It is understood that in some embodiments, a variant gp160 or gp140 polypeptide described herein comprises a variant gp120 polypeptide described herein.

In some embodiments, an engineered or non-naturally occurring HIV Env polypeptide described herein is missing glycan sequons at N156 and N130 and has one or more basic residues at positions 168 to 171 that binds to a Human Immunodeficiency Virus (HIV) broadly neutralizing antibody (bnAb), wherein the HIV Env polypeptide positions correspond to the HXB2 reference (SEQ ID NO: 1). In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, an engineered or non-naturally occurring HIV Env polypeptide described herein is missing glycan sequons at N156 and N130 and has one or more basic residues at positions 168 to 171 that binds to an HIV broadly neutralizing antibody (bnAb) directed to the V2 apex region of HIV envelope, wherein the HIV Env polypeptide positions correspond to the HXB2 reference (SEQ ID NO: 1). In some embodiments, the bnAb is PG9, PG16, CAP256.08, CAP256.09, CH01, CH04, PGT145, or PGDM1400. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, an engineered or non-naturally occurring HIV Env polypeptide described herein is missing glycan sequons at N156 and N130 and has one or more basic residues at positions 168 to 171 that binds to a germline or germline reverted HIV broadly neutralizing antibody (bnAb) directed to the V2 apex region of HIV envelope, wherein the HIV Env polypeptide positions correspond to the HXB2 reference (SEQ ID NO: 1). In some embodiments, the germline or germline reverted bnAb is CAP256 UCA, PG9 iGL, CH01 iGL, or PGT145 iGL. In some embodiments, the germline or germline reverted bnAb is CH01 iGL. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, a chimeric HIV Env polypeptide described herein comprises an Env polypeptide backbone and the V1V2 region of the ZM233 HIV Env polypeptide. In some embodiments, the V1V2 region of the ZM233 HIV Env polypeptide comprises the amino acid sequence of SEQ ID NO: 9. In some embodiments, the HIV Env polypeptide backbone comprises a BG505, ZM197, or CFR250 backbone. In some embodiments, the chimeric HIV Env polypeptide misses glycan sequons at N156 and N130, wherein the HIV Env polypeptide positions correspond to the HXB2 reference (SEQ ID NO: 1). In some embodiments, the chimeric HIV Env polypeptide binds to an HIV broadly neutralizing antibody (bnAb) directed to the V2 apex region of HIV envelope. In some embodiments, the chimeric HIV Env polypeptide binds to a germline or germline reverted HIV broadly neutralizing antibody (bnAb) directed to the V2 apex region of HIV envelope. In some embodiments, the bnAb is PG9, PG16, CAP256.08, CAP256.09, CH01, CH04, PGT145, or PGDM1400. In some embodiments, the germline or germline reverted bnAb is CAP256 UCA, PG9 iGL, CH01 iGL, or PGT145 iGL. In some embodiments, the germline or germline reverted bnAb is CH01 iGL. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, a chimeric HIV Env polypeptide described herein comprises an Env polypeptide backbone and the amino acid residues of the ZM233 HIV Env polypeptide corresponding to positions about 131 to about 196, wherein the HIV Env polypeptide positions correspond to the HXB2 reference (SEQ ID NO: 1). In some embodiments, the HIV Env polypeptide backbone comprises a BG505, ZM197, or CFR250 backbone. In some embodiments, the chimeric HIV Env polypeptide misses glycan sequons at N156 and N130, wherein the HIV Env polypeptide positions correspond to the HXB2 reference (SEQ ID NO: 1). In some embodiments, the chimeric HIV Env polypeptide binds to an HIV broadly neutralizing antibody (bnAb) directed to the V2 apex region of HIV envelope. In some embodiments, the chimeric HIV Env polypeptide binds to a germline or germline reverted HIV broadly neutralizing antibody (bnAb) directed to the V2 apex region of HIV envelope. In some embodiments, the bnAb is PG9, PG16, CAP256.08, CAP256.09, CH01, CH04, PGT145, or PGDM1400. In some embodiments, the germline or germline reverted bnAb is CAP256 UCA, PG9 iGL, CH01 iGL, or PGT145 iGL. In some embodiments, the germline or germline reverted bnAb is CH01 iGL. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, a chimeric HIV Env polypeptide described herein is missing glycan sequons at N156 and N130 and comprises an Env polypeptide backbone and the V1V2 region of the ZM233 HIV Env polypeptide. In some embodiments, the V1V2 region of the ZM233 HIV Env polypeptide comprises the amino acid sequence of SEQ ID NO: 9. In some embodiments, the HIV Env polypeptide backbone comprises a BG505, ZM197, or CFR250 backbone. In some embodiments, the chimeric HIV Env polypeptide binds to an HIV broadly neutralizing antibody (bnAb) directed to the V2 apex region of HIV envelope. In some embodiments, the chimeric HIV Env polypeptide binds to a germline or germline reverted HIV broadly neutralizing antibody (bnAb) directed to the V2 apex region of HIV envelope. In some embodiments, the bnAb is PG9, PG16, CAP256.08, CAP256.09, CH01, CH04, PGT145, or PGDM1400. In some embodiments, the germline or germline reverted bnAb is CAP256 UCA, PG9 iGL, CH01 iGL, or PGT145 iGL. In some embodiments, the germline or germline reverted bnAb is CH01 iGL. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, a chimeric HIV Env polypeptide described herein is missing glycan sequons at N156 and N130 and comprises an Env polypeptide backbone and the amino acid residues of the ZM233 HIV Env polypeptide corresponding to positions about 131 to about 196, wherein the HIV Env polypeptide positions correspond to the HXB2 reference (SEQ ID NO: 1). In some embodiments, the HIV Env polypeptide backbone comprises a BG505, ZM197, or CFR250 backbone. In some embodiments, the chimeric HIV Env polypeptide binds to an HIV broadly neutralizing antibody (bnAb) directed to the V2 apex region of HIV envelope. In some embodiments, the chimeric HIV Env polypeptide binds to a germline or germline reverted HIV broadly neutralizing antibody (bnAb) directed to the V2 apex region of HIV envelope. In some embodiments, the bnAb is PG9, PG16, CAP256.08, CAP256.09, CH01, CH04, PGT145, or PGDM1400. In some embodiments, the germline or germline reverted bnAb is CAP256 UCA, PG9 iGL, CH01 iGL, or PGT145 iGL. In some embodiments, the germline or germline reverted bnAb is CH01 iGL. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, an engineered or non-naturally occurring ZM233 HIV Env polypeptide described herein is missing glycan sequons at N156 and N130, wherein the HIV Env polypeptide positions correspond to the HXB2 reference (SEQ ID NO: 1). In some embodiments, the engineered or non-naturally occurring ZM233 HIV Env polypeptide binds to a germline or germline reverted HIV broadly neutralizing antibody (bnAb) directed to the V2 apex region of HIV envelope. In some embodiments, the engineered or non-naturally occurring ZM233 HIV Env polypeptide binds to a germline or germline reverted HIV broadly neutralizing antibody (bnAb) directed to the V2 apex region of HIV envelope. In some embodiments, the bnAb is PG9, PG16, CAP256.08, CAP256.09, CH01, CH04, PGT145, or PGDM1400. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, an HIV Env polypeptide described herein comprises a V2 apex epitope from envelope sequence of virus ZM233. In some embodiments, the HIV Env polypeptide comprises basic amino acid substitutions at positions 168 to 171. In some embodiments, the V2 apex region of positions 156 to 175 comprises one glycan and four consecutive basic amino acids.

In some embodiments, an HIV Env polypeptide described herein comprises the amino acid sequence of I-C-$X_1$-F-N-$X_2$-$X_3$-$X_4$-$X_5$-$X_6$-$X_7$-$X_8$-$X_9$-$X_{10}$-$X_{11}$-$X_{12}$-V-N-V-L (SEQ ID NO: 10) at positions 156 to 175, wherein $X_1$ comprises S, T, N, or F; $X_2$ comprises I, V, T, Q, of M; $X_3$ comprises S or T; $X_4$ comprises S or T; $X_5$ comprises S, E, or G; $X_6$ comprises I, L, or V; $X_7$ comprises K or R; $X_8$ comprises G or D; $X_9$ comprises K, R, E, or Q; $X_{10}$ comprises K, R, E, or Q; $X_{11}$ comprises K, R, E, or Q; and $X_{12}$ comprises K, E, or Q. In some embodiments, at least three of $X_9$, $X_{10}$, $X_{11}$, and $X_{12}$ comprise basic amino acid residues. In some embodiments, all of $X_9$, $X_{10}$, $X_{11}$, and $X_{12}$ comprise basic amino acid residues. In some embodiments, $X_9$, $X_{10}$, $X_{11}$, and $X_{12}$ comprise K. In some embodiments, the HIV Env polypeptide comprises the amino acid sequence of ICSFNMTTELRDKKRKVNVL (SEQ ID NO: 11) at positions 156 to 175. In some embodiments, the HIV Env polypeptide binds to a germline or germline reverted HIV broadly neutralizing antibody (bnAb) directed to the V2 apex region of HIV envelope. In some embodiments, the Env polypeptide binds to a germline or germline reverted HIV broadly neutralizing antibody (bnAb) directed to the V2 apex region of HIV envelope. In some embodiments, the bnAb is PG9, PG16, CAP256.08, CAP256.09, CH01, CH04, PGT145, or PGDM1400. In some embodiments, the HIV Env polypeptide comprises gp140. In some embodiments, the HIV Env polypeptide comprises a complex of gp120 and gp41. In some embodiments, the HIV Env polypeptide comprises a stabilized trimer. In some embodiments, the trimer is a SOSIP, NFL, or UFO trimer. In some embodiments, the trimer is a SOSIP trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, an HIV Env polypeptide described herein comprises an amino acid sequence having at least about 80%, at least about 90%, at least about 95%, at least about 97%, at least about 99%, or 100% sequence identity to the amino acid sequence of SEQ ID NO: 6, 7, or 8. In some embodiments, the HIV Env polypeptide comprises the amino acid sequence of SEQ ID NO: 6, 7, or 8.

In some embodiments, an HIV Env polypeptide described herein comprises a complex of gp120 and gp41. In some embodiments, an HIV Env polypeptide described herein comprises gp140. In some embodiments, an HIV Env polypeptide described herein comprises a stabilized trimer. In some embodiments, the trimer is a SOSIP, NFL, or UFO trimer. In some embodiments, the trimer is a SOSIP trimer. In some embodiments, the trimer is a NFL trimer. In some embodiments, the trimer is a UFO trimer. In some embodiments, the trimer comprises gp120-gp41 heterodimers. In some embodiments, the heterodimers are covalently linked. In some embodiments, the heterodimers comprise gp120-gp41 fusion proteins.

In some embodiments, a chimeric HIV Env polypeptide described herein binds to a Human Immunodeficiency Virus (HIV) broadly neutralizing antibody (bnAb). In some embodiments, a chimeric HIV Env polypeptide described herein binds to an HIV broadly neutralizing antibody (bnAb) directed to the V2 apex region of HIV envelope. In some embodiments, a chimeric HIV Env polypeptide described herein binds to a germline or germline reverted HIV broadly neutralizing antibody (bnAb) directed to the V2 apex region of HIV envelope. In some embodiments, the bnAb is PG9, PG16, CAP256.08, CAP256.09, CH01, CH04, PGT145, or PGDM1400. In some embodiments, the germline or germline reverted bnAb is CAP256 UCA, PG9 iGL, CH01 iGL, or PGT145 iGL. In some embodiments, the germline or germline reverted bnAb is CH01 iGL.

The affinity of an isolated polypeptide disclosed for an antibody described herein (e.g., BG18 iGL0) can be determined experimentally using any suitable method well-known in the art, e.g., flow cytometry, enzyme-linked immunoabsorbent assay (ELISA), biolayer interferometry (BLI) assay, radioimmunoassay (RIA), or kinetics (e.g., BIA-CORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art and such as the buffer described herein.

In some embodiments, an isolated polypeptide described herein comprises a gp140. In some embodiments, an isolated polypeptide described herein comprises a gp120.

In one aspect, provided herein are HIV Env trimers comprising an isolated polypeptide described herein. In some embodiments, an HIV Env trimer described herein is a homotrimer. In some embodiments, an HIV Env trimer described herein a heterotrimer. In some embodiments, an HIV Env trimer described herein comprises gp120-gp41 heterodimers. In some embodiments, an HIV Env trimer described herein comprises gp120-gp41 heterodimers wherein the heterodimers are covalently linked. In some embodiments, an HIV Env trimer described herein comprises gp120-gp41 fusions. In some embodiments, an HIV Env trimer described herein is a stabilized trimer. In some embodiments, an HIV Env trimer described herein is an SOSIP, NFL or UFO trimer. In some embodiments, an HIV Env trimer described herein is an SOSIP trimer. In some embodiments, an HIV Env trimer described herein comprises a variant gp120 polypeptide described herein.

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci US All 1(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-I primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci US A 109(30):12111-12116; Nkolola J P, et al. (2014) Comparison of multiple adjuvants on the stability and immunogenicity of a clade C HIV-I gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bnAbs, (GE148 and GE136) generated following immunization of uncleaved gp140 trimers (YU2 gp140-foldon) in non-human primates (NHP). Non-bnAbs, represented by GE136 and 148, can only neutralize the sensitive so-called "tier I viruses" that are not representative of the more neutralization resistant tier 2-like primary isolates circulating in the human population. Using crystallography, EM reconstructions, paratope scanning and molecular modeling, Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci USA 111(7):E738-747).

The cumulative historical data have led to the hypothesis that a more faithful mimic of the HIV-I spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNHI 144 SOSIP is also available but does not provide atomic level details (Bartesaghi A, Merk A, Borgnia M J, Milne J L, & Subramaniam S (2013) Nat Struct Mol Biol 20(12):1352-1357). The BG505 SOSIP and KNH1144 SOSIP trimers are derived from the Env sequences of the subtype A BG505 and KNHI 144 strains. These soluble trimers possess an engineered disulfide linkage between the gp120 and gp41 (at residues 501C and 605C, respectively) and an additional mutation in the heptad repeat I (HRI) of gp41 (1559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al.

(2013) PLoS Pathog 9(9):e1003618; Sanders R W, et al. (2002) J Virol 76(17):8875-8889). Although SOSIP molecules based on other HIV-I primary strains were attempted over the past decade, the BG505- and KNHI 144-derived SOSIP trimers are the two limited examples of SOSIPs that yield homogeneous trimers suitable for high resolution biophysical and structural analysis. The structural explanation for the difficulty to readily transfer the SOSIP design to other HIV-I strain-derived sequences is not yet fully understood and would be valuable information to broaden the trimer design horizon.

Since the initial soluble native-like BG505 SOPIP.664 Env trimer was confirmed to adopt a near-native conformation by high-resolution structural analysis, multiple efforts to produce stable, soluble Env mimetics derived from multiple HIV-1 strains were pursued. Multiple solutions to this objective include the improved cleavage-independent NFL trimers, UFOs and modified SOSIPs. Both the SOSIP and NFL well-ordered trimers are efficiently recognized by broadly neutralizing antibodies (bnAbs) which arise sporadically during the course of natural infection. In some cases, including the important advances described here, have been used to isolate such bnAbs. One approach to elicit tier 2 neutralizing Abs has been to immunize the existing well-ordered trimers using prime:boosting in selected animal models. For BG505 and 16055 native-like trimers this approach does elicit tier 2 neutralizing antibodies, but of limited cross-reactive breadth.

Most cross-conserved sites on the HIV Env spike are occluded by evolved, incorporated self-N-glycans, limiting naïve B cell recognition of the underlying polypeptide surface. The exceptions are the protein surfaces of the primary receptor CD4 binding site (CD4bs) and the furin cleavage site (proximal to the gp120:41 interface). Infrequently, during the course of the natural HIV infection process, bnAbs are elicited to these aforementioned sites of vulnerability. In addition, other bnAbs directed to the V2 apex, the 332N-glycan supersite and to the fusion peptide or the high-mannose patch are elicited during the course of chronic HIV infection.

After decades of development, advances in soluble HIV-1 Env mimics design permits the generation of a diverse array of native-like trimers (Ward and Wilson, 2017. The HIV-1 envelope glycoprotein structure: nailing down a moving target. Immunol Rev 275:21-32; Karlsson et al., 2017. Evolution of B cell analysis and Env trimer redesign. Immunol Rev 275:183-202). The successful development of the soluble SOSIP trimers provided proof-of-principle (Sanders et al, 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618) forming a prefusion native-like conformation (Lyumkis et al., 2013. Cryo-EM structure of a fully glycosylated soluble cleaved HIV-1 envelope trimer. Science 342:1484-1490; Julien et al, 2013. Crystal structure of a soluble cleaved HIV-1 envelope trimer. Science 342:1477-1483; Garces et al., 2015. Affinity Maturation of a Potent Family of HIV Antibodies Is Primarily Focused on Accommodating or Avoiding Glycans. Immunity 43:1053-1063; Pancera et al., 2014. Structure and immune recognition of trimeric pre-fusion HIV-1 Env. Nature 514:455-461). The SOSIP gp140 trimer is proteolytically cleaved by cellular furins to gp120 and gp41 subunits and covalently linked by an engineered intra-protomer disulfide bond A501C-T605C (SOS). These trimers also require mutation (I559P) in the gp41 heptad repeat 1 (HR1) to maintain well-ordered oligomers, as well as expression of exogenous furin for full conformational integrity (Sanders et al., 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618; Guenaga et al., 2015. Well-Ordered Trimeric HIV-1 Subtype B and C Soluble Spike Mimetics Generated by Negative Selection Display Native-like Properties. PLoS Pathog 11:e1004570; Julien et al., 2015. Design and structure of two HIV-1 clade C SOSIP.664 trimers that increase the arsenal of native-like Env immunogens. Proc Natl Acad Sci USA 112:11947-11952; de Taeye et al. 2015. Immunogenicity of Stabilized HIV-1 Envelope Trimers with Reduced Exposure of Non-neutralizing Epitopes. Cell 163:1702-1715; Pugach et al. 2015. A native-like SOSIP.664 trimer based on an HIV-1 subtype B env gene. J Virol 89:3380-3395; Ringe et al. 2013. Cleavage strongly influences whether soluble HIV-1 envelope glycoprotein trimers adopt a native-like conformation. Proc Natl Acad Sci USA 110:18256-18261; Ringe et al. 2015. Influences on the Design and Purification of Soluble, Recombinant Native-Like HIV-1 Envelope Glycoprotein Trimers. J Virol 89:12189-12210; Ringe et al. 2017. Reducing V3 Antigenicity and Immunogenicity on Soluble, Native-Like HIV-1 Env SOSIP Trimers. J Virol 91; Ahmed et al. 2017. Stabilization of a soluble, native-like trimeric form of an efficiently cleaved Indian HIV-1 clade C envelope glycoprotein. J Biol Chem 292:8236-8243; Sanders et al. 2002. Stabilization of the soluble, cleaved, trimeric form of the envelope glycoprotein complex of human immunodeficiency virus type 1. J Virol 76:8875-8889; Binley et al. 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 74:627-643). In the past years, Applicants developed an improved native-like trimer design, generating well-ordered soluble Env mimics that are fully cleavage-independent, termed native flexibly linked (NFL) trimers. This design uses a flexible linker (two copies of Gly4-Ser, "G4S") to replace the natural cleavage site and sequence (Sharma et al. 2015. Cleavage-independent HIV-1 Env trimers engineered as soluble native spike mimetics for vaccine design. Cell Rep 11:539-550). The flexible linker between the natural C-terminus of gp120 and N-terminus of gp4l, allows the un-cleaved trimers to achieve a native-like conformation without the need of furin for precursor processing. However, the original NFL trimer design contains the I559P mutation (Sharma et al. 2015. Cleavage-independent HIV-1 Env trimers engineered as soluble native spike mimetics for vaccine design. Cell Rep 11:539-550) that was initially identified in the SOSIP context to disfavor the post fusion state (Sanders et al. 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618). Both the original SOSIP and NFL designs do not form a high percentage of well-ordered trimers in all Env contexts. In the original NFL design, it is relatively inefficient in generating high yields of trimers derived from clade C strains, such as 16055 (Guenaga et al. 2015. Structure-Guided Redesign Increases the Propensity of HIV Env To Generate Highly Stable Soluble Trimers. J Virol 90:2806-2817). To improve trimer design, Applicants incorporated residues from BG505 (called trimer-derived (TD) residues) into 16055 NFLs, substantially improving the propensity to form native-like trimers (Guenaga et al. 2015. Structure-Guided Redesign Increases the Propensity of HIV Env To Generate Highly Stable Soluble Trimers. J Virol 90:2806-2817) and the elicitation of tier 2 clade C neutralizing antibodies (Martinez-Murillo et al., GB. 2017. Particulate Array of Well-Ordered HIV Clade C Env Trimers Elicits Neutralizing Antibodies that Display a Unique V2 Cap Approach. Immunity 46:804-817 e807; Dubrovskaya et al. 2017. Targeted N-glycan deletion at the receptor-binding site retains HIV Env NFL trimer integrity and accelerates the elicited antibody response. PLoS Pathog 13:e1006614). Further improvements on the TD design by targeted glycine substitutions at helix-to-coil transitions that disfavor the post-fusion state of Env (TD CC+, namely "TD+"), significantly improve trimer homogeneity, yield, stability and antigenicity, resulting in the first high-resolution clade C Env structure (Guenaga et al. 2017. Glycine Substitution at Helix-to-Coil Transitions Facilitates the Structural Determination of a Stabilized Subtype C HIV Envelope Glycoprotein. Immunity 46:792-803 e793).

In one aspect, provided herein are nanoparticles comprising an isolated polypeptide described herein. In some embodiments, a nanoparticle described herein is a ferritin nanoparticle, an encapsulin nanoparticle, a Sulfur Oxygenase Reductase (SOR) nanoparticle, a lumazine synthase nanoparticle or a pyruvate dehydrogenase nanoparticle. In some embodiments, a nanoparticle described herein is a ferritin nanoparticle. In some embodiments, a nanoparticle described herein comprises an amino acid sequence having at least about 80%, at least about 90%, at least about 95%, at least about 97%, at least about 99%, or 100% sequence identity to the amino acid sequence of SEQ ID NO: 6, 7, or 8. In some embodiments, a nanoparticle described herein comprises the amino acid sequence of SEQ ID NO: 6, 7, or 8. In some embodiments, a nanoparticle described herein is a ferritin nanoparticle comprising the amino acid sequence of SEQ ID NO. 6, 7, or 8.

In one aspect, provided herein are virus-like particles (VLPs) comprising an isolated polypeptide described herein.

It should be understood that in some embodiments, the polypeptides (e.g., Env trimers, nanoparticles, and other antigens) described herein can differ from the exact sequences illustrated and described herein. Thus, the invention contemplates deletions, additions and substitutions to the sequences shown, so long as the sequences function in accordance with the methods described herein. In this regard, in some embodiments, substitutions are conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, praline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention

III. Polynucleotides

In one aspect, provided herein are isolated polynucleotides encoding an HIV Env polypeptide described herein.

In some embodiments, an isolated polynucleotide described herein is a DNA. In some embodiments, an isolated polynucleotide described herein is an mRNA. In some embodiments, an isolated polynucleotide described herein is an mRNA comprising a modified nucleotide.

Further provided herein are vectors comprising a polynucleotide described herein. In some embodiments, a vector described herein can be used for recombinant expression of an HIV Env polypeptide described herein, an HIV Env trimer described herein, or a nanoparticle described herein. In one embodiment, a vector described herein can be used for administration of an HIV Env polypeptide described herein, an HIV Env trimer described herein, or a nanoparticle described herein to a patient in need thereof.

In one aspect, provided herein are RNA replicons comprising an isolated polynucleotide described herein.

In some embodiments, an isolated polynucleotide described herein encodes an HIV Env polypeptide described herein. In some embodiments, the HIV Env polypeptide misses glycan sequons at N156 and N130 and has one or more basic residues at positions 168 to 171 that binds to a Human Immunodeficiency Virus (HIV) broadly neutralizing antibody (bnAb), wherein the HIV Env polypeptide positions correspond to the HXB2 reference (SEQ ID NO: 1). In some embodiments, the HIV Env polypeptide described herein misses glycan sequons at N156 and N130 and has one or more basic residues at positions 168 to 171 that binds to an HIV broadly neutralizing antibody (bnAb) directed to the V2 apex region of HIV envelope, wherein the HIV Env polypeptide positions correspond to the HXB2 reference. In some embodiments, the HIV Env polypeptide described herein misses glycan sequons at N156 and N130 and has one or more basic residues at positions 168 to 171 that binds to a germline or germline reverted HIV broadly neutralizing antibody (bnAb) directed to the V2 apex region of HIV envelope, wherein the HIV Env polypeptide positions correspond to the HXB2 reference.

In some embodiments, the HIV Env polypeptide comprises an Env polypeptide backbone and the V1V2 region of the ZM233 HIV Env polypeptide. In some embodiments, the HIV Env polypeptide is missing glycan sequons at N156 and N130 and comprises an Env polypeptide backbone and the V1V2 region of the ZM233 HIV Env polypeptide. In some embodiments, the V1V2 region of the ZM233 HIV Env polypeptide comprises the amino acid sequence of SEQ ID NO: 9. In some embodiments, the HIV Env polypeptide comprises an Env polypeptide backbone and the amino acid residues of the ZM233 HIV Env polypeptide corresponding to positions about 131 to about 196, wherein the HIV Env polypeptide positions correspond to the HXB2 reference. In some embodiments, the HIV Env polypeptide is missing glycan sequons at N156 and N130 and comprises an Env polypeptide backbone and the amino acid residues of the ZM233 HIV Env polypeptide corresponding to positions about 131 to about 196, wherein the HIV Env polypeptide positions correspond to the HXB2 reference. In some embodiments, the HIV Env polypeptide backbone comprises a BG505, ZM197, or CFR250 backbone.

In some embodiments, the ZM233 HIV Env polypeptide is missing glycan sequons at N156 and N130, wherein the HIV Env polypeptide positions correspond to the HXB2 reference.

In some embodiments, the HIV Env polypeptide comprises the amino acid sequence of I-C-$X_1$-F-N-$X_2$-$X_3$-$X_4$-$X_5$-$X_6$-$X_7$-$X_8$-$X_9$-$X_{10}$-$X_{11}$-$X_{12}$-V-N-V-L (SEQ ID NO: 10) at positions 156 to 175, wherein $X_1$ comprises S, T, N, or F; $X_2$ comprises I, V, T, Q, of M; $X_3$ comprises S or T; $X_4$ comprises S or T; $X_5$ comprises S, E, or G; $X_6$ comprises I, L, or V; $X_7$ comprises K or R; $X_8$ comprises G or D; $X_9$ comprises K, R, E, or Q; $X_{10}$ comprises K, R, E, or Q; $X_{11}$ comprises K, R, E, or Q; and $X_{12}$ comprises K, E, or Q.

In some embodiments, the HIV Env polypeptide comprises the amino acid sequence of SEQ ID NO: 6, 7, or 8.

In some embodiments, an isolated polynucleotide described herein encodes a nanoparticle described herein. In some embodiments, a nanoparticle described herein comprises the amino acid sequence of SEQ ID NO: 6, 7, or 8. In some embodiments, a nanoparticle described herein is a ferritin nanoparticle comprising the amino acid sequence of SEQ ID NO: 6, 7, or 8.

In some embodiments, an isolated polynucleotide described herein encodes an HIV Env trimer described herein. In some embodiments, the HIV Env trimer described herein comprises the amino acid sequence of SEQ ID NO: 6, 7, or 8.

In one embodiment, an isolated polynucleotide described herein encodes a polypeptide (e.g., HIV Env trimer or nanoparticle) described herein and comprises an mRNA. In one embodiment, the mRNA comprises at least one modified nucleotide. In one embodiment, a modified mRNA encoding a polypeptide (e.g., HIV Env trimer or nanoparticle) described herein is for administering to a subject to treat or prevent HIV infection.

As used herein, an "isolated" polynucleotide or nucleic acid molecule is one, which is separated from other nucleic acid molecules, which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a polypeptide (e.g., HIV Env trimer or nanoparticle) described herein is isolated or purified.

In yet another specific embodiment, a polynucleotide provided herein comprises a nucleotide sequence encoding a polypeptide (e.g., HIV Env trimer or nanoparticle) described herein that is optimized, e.g., by codon/RNA optimization, replacement with heterologous signal sequences, and elimination of mRNA instability elements. Methods to generate optimized nucleic acids for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding a polypeptide (e.g., HIV Env trimer or nanoparticle) described herein can hybridize to an antisense (e.g., complementary) polynucleotide of an unoptimized polynucleotide sequence encoding polypeptide described herein or a fragment thereof (e.g., VL domain or VH domain). In specific embodiments, an optimized nucleotide sequence encoding a polypeptide (e.g., HIV Env trimer or nanoparticle) described herein or a fragment hybridizes under high stringency conditions to antisense polynucleotide of an unoptimized polynucleotide sequence encoding a polypeptide (e.g., HIV Env trimer or nanoparticle) described herein or a fragment thereof. In a specific embodiment, an optimized nucleotide sequence encoding a polypeptide (e.g., HIV Env trimer or nanoparticle) described herein hybridizes under high stringency, intermediate or lower stringency hybridization conditions to an antisense polynucleotide of an unoptimized nucleotide sequence encoding a polypeptide (e.g., HIV Env trimer or nanoparticle) described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, and modified versions of these antibodies can be determined using methods well-known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-246), which, briefly, involves the synthesis of overlapping oligonucleotides containing portions of the sequence encoding the antibody, annealing and ligating of those oligonucleotides, and then amplification of the ligated oligonucleotides by PCR.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a polypeptide (e.g., HIV Env trimer or nanoparticle) provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

IV. Vectors, Cells, and Methods of Producing a Polypeptide

In one aspect, provided herein are isolated vectors comprising a polynucleotide described herein. In some embodiments, an isolated vector described herein is a viral vector.

In one aspect, provided herein are recombinant viruses comprising a polynucleotide described herein. In some embodiments, a recombinant virus described herein is a recombinant adeno-associated virus (AAV).

In one aspect, provided herein are host cells comprising a polynucleotide described herein, or a vector described herein. In some embodiments, a host cell described herein is selected from the group consisting of E. coli, Pseudomonas, Bacillus, Streptomyces, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

In one aspect, provided herein are methods of producing an HIV Env polypeptide described herein, an HIV Env trimer described herein, or a nanoparticle described herein comprising, culturing the host cell described herein so that the polynucleotide is expressed and the HIV Env polypeptide, HIV Env trimer, or the nanoparticle is produced.

In certain aspects, provided herein are cells (e.g., host cells) expressing (e.g., recombinantly) polypeptides described herein and related polynucleotides and expression vectors. Provided herein are vectors (e.g., expression vectors) comprising polynucleotides comprising nucleotide sequences encoding polypeptides described herein. In one embodiment, the vectors can be used for recombinant expression of a polypeptide described herein in host cells (e.g., mammalian cells). In one embodiment, the vectors can be used for administration of a polypeptide described herein to a patient in need thereof. Also provided herein are host cells comprising such vectors for recombinantly expressing polypeptides described herein. In a particular aspect, provided herein are methods for producing a polypeptide described herein, comprising expressing such polypeptides in a host cell.

In certain aspects, provided herein is an isolated vector comprising a polynucleotide described herein. In one embodiment, the vector is a viral vector.

In certain aspects, provided herein is a recombinant virus comprising a polynucleotide described herein. In one embodiment, the recombinant virus encodes a polypeptide described herein. In one embodiment, the recombinant virus encodes a variant HIV Env polypeptide described herein. In one embodiment, the recombinant virus is a replication defective virus. Suitable replication defective viral vectors are known to those skilled in the art, for example, as disclosed in U.S. Pat. Nos. 7,198,784, 9,408,905, 9,862,931, 8,067,156, U.S. Pat. Appl. Pub. Nos. 20150291935, 20120220492, 20180291351, and 20170175137, each of which is incorporated herein by reference in its entirety. In one embodiment, the recombinant virus is a retrovirus or retroviral vector, for example, a lentivirus or lentiviral vector. In one embodiment, the recombinant virus is an adenovirus or adenoviral vector, HSV or HSV vector, or influenza virus or viral vector. In one embodiment, the recombinant virus is an adeno-associated virus (AAV). In one embodiment, the recombinant virus is for administration to a subject to prevent or treat HIV infection. In one embodiment, the recombinant virus is an adeno-associated virus (AAV) for administration to a subject to prevent or treat HIV infection. Recombinant AAV particles encoding a polypeptide described herein and methods for producing thereof are known to one skilled in the art, for example, as disclosed in U.S. Pat. No. 8,865,881 and US20190031740, each of which is incorporated by reference herein in its entirety for all purposes. See also, Lin and Balazs, Retro-virology 15:66 (2018) and van den Berg et al., Molecular Therapy: Methods & Clinical Development 14:100-112 (2019), each of which is incorporated by reference herein in its entirety for all purposes.

In certain aspects, provided herein is a host cell comprising a polynucleotide described herein, or a vector described herein. In one embodiment, the vector encodes a polypeptide described herein.

In one embodiment, the host cell is selected from the group consisting of E. coli, Pseudomonas, Bacillus, Streptomyces, yeast, CHO, YB/20, NS0, PER-C6, HEK-293T, NIH-3T3, Helga, BHK, Hep G2, SP2/0, R1.1, B-W, L-M, COS 1, COS 7, BSC1, BSC40, BMT10 cell, plant cell, insect cell, and human cell in tissue culture. In one embodiment, the host cell is CHO.

In certain aspects, provided herein is a method of producing a polypeptide described herein comprising culturing a host cell described herein so that the polynucleotide is expressed and the polypeptide is produced. In one embodiment, the method further comprises recovering the polypeptide.

The isolated polypeptides (e.g., HIV Env trimer or nanoparticle) described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding polypeptides of interest. Recombinant expression vectors are replicable DNA constructs, which have synthetic or cDNA-derived DNA fragments encoding a polypeptide operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor, which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A variety of host-expression vector systems can be utilized to express polypeptide molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express a polypeptide molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces pichia*) transformed with recombinant yeast expression vectors containing polypeptide coding sequences; insect cell systems infected with recombinant virus expression vectors (e.g., baculovirus) containing polypeptide coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing polypeptide coding sequences; or mammalian cell systems (e.g., COS (e.g., COS1 or COS), CHO, BHK, MDCK, HEK 293, NS0, PER. C6, VERO, CRL7O3O, HsS78Bst, Helga, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing polypeptides described herein are CHO cells, for example CHO cells from the CHO GS System™ (Lonza). In a particular embodiment, cells for expressing polypeptides described herein are human cells, e.g., human cell lines. In a specific embodiment, a mammalian expression vector is pOptiVEC™ or pcDNA3.3. In a particular embodiment, bacterial cells such as *E. coli*, or eukaryotic cells (e.g., mammalian cells) are used for the expression of a recombinant polypeptide molecule. For example, mammalian cells such as Chinese hamster ovary (CHO) cells in conjunction with a vector such as the major intermediate early gene promoter element from human cytomegalovirus is an effective expression system for polypeptides. In a specific embodiment, the expression of nucleotide sequence encoding polypeptides described herein is regulated by a constitutive promoter, inducible promoter or tissue specific promoter.

For applications where it is desired that the polypeptides described herein be expressed in vivo, for example in a subject in need of treatment with a polypeptide described herein, any vector that allows for the expression of the polypeptides and is safe for use in vivo can be used. In one embodiment, the vector is a viral vector. Viral vectors can include poxvirus (vaccinia), including vaccinia Ankara and canarypox; adenoviruses, including adenovirus type 5 (Ad5); rubella; sendai virus; rhabdovirus; alphaviruses; and adeno-associated viruses. In one embodiment, the viral vector is an adeno-associated virus. Alternatively, a polynucleotide encoding the polypeptide could be delivered as DNA or RNA to the subject for in vivo expression of the polypeptide.

Suitable host cells for expression of a polypeptide of interest such as a polypeptide described herein include prokaryotes, yeast, insect or higher eukaryotic cells under the control of appropriate promoters. Prokaryotes include gram negative or gram-positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express a recombinant protein such as a polypeptide described herein. Expression of recombinant proteins in mammalian cells can be performed because such proteins are generally correctly folded, appropriately modified and completely functional. Examples of suitable mammalian host cell lines include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7O3O, COS (e.g., COS1 or COS), PER. C6, VERO, HsS78Bst, HEK-293T, HepG2, SP210, R1.1, B-W, L-M, BSC1, BSC40, YB/20, BMT10 and HsS78Bst cells. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza HA peptide sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems, which secrete recombinant protein, e.g., a polypeptide, into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further an agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In specific embodiments, a polypeptide (e.g., HIV Env trimer or nanoparticle) described herein is isolated or purified. Generally, an isolated polypeptide is one that is substantially free of other polypeptides. For example, in a particular embodiment, a preparation of a polypeptide described herein is substantially free of cellular material and/or chemical precursors. The language "substantially free of cellular material" includes preparations of a polypeptide in which the polypeptide is separated from cellular components of the cells from which it is isolated or recombinantly produced. Thus, a polypeptide that is substantially free of cellular material includes preparations having less than about 30%, 20%, 10%, 5%, 2%, 1%, 0.5%, or 0.1% (by dry weight) of heterologous protein (also referred to herein as a "contaminating protein") and/or variants of a polypeptide, for example, different post-translational modified forms of a polypeptide. When the polypeptide (e.g., HIV Env trimer or nanoparticle described herein) is recombinantly produced, it is also generally substantially free of culture medium, i.e., culture medium represents less than about 20%, 10%, 2%, 1%, 0.5%, or 0.1% of the volume of the protein preparation. When the polypeptide (e.g., HIV Env trimer or nanoparticle described herein) is produced by chemical synthesis, it is generally substantially free of chemical precursors or other chemicals, i.e., it is separated from chemical precursors or other chemicals, which are involved in the synthesis of the protein. Accordingly, such preparations of the polypeptide (e.g., HIV Env trimer or nanoparticle described herein) have less than about 30%, 20%, 10%, or 5% (by dry weight) of chemical precursors or compounds other than the polypeptide of interest. In one embodiment, polypeptides described herein are isolated or purified.

V. Pharmaceutical and Immunogenic Compositions

Compositions comprising polypeptides described herein (e.g., HIV Env trimer or nanoparticle) are also provided. Further provided herein are compositions comprising a polynucleotide encoding a polypeptide described herein. In some embodiments, the polynucleotide comprises mRNA. In some embodiments, the composition is a pharmaceutical composition. In some embodiments, the composition is an immunogenic composition.

In one aspect, provided herein are pharmaceutical compositions comprising an HIV Env polypeptide described herein, HIV Env trimer described herein, nanoparticle described herein, polynucleotide described herein, recombinant virus described herein, VLP described herein, or liposome described herein and a pharmaceutically acceptable excipient. In some embodiments, the composition is an immunogenic composition. In some embodiments, the composition is a vaccine. In some embodiments, an immunogenic composition or vaccine further comprises an adjuvant. In some embodiments, the composition (e.g., immunogenic composition) is formulated for subcutaneous administration. In some embodiments, the composition (e.g., immunogenic composition) is formulated for intramuscular administration. In some embodiments, the composition (e.g., immunogenic composition) is formulated for topical administration, and in certain embodiments the composition is formulated for vaginal or rectal administration.

In one aspect, provided herein are immunogenic compositions comprising an HIV Env polypeptide described herein, HIV Env trimer described herein, nanoparticle described herein, polynucleotide described herein, recombinant virus described herein, VLP described herein, or liposome described herein and a pharmaceutically acceptable excipient.

In some embodiments, an immunogenic composition described herein further comprises an adjuvant. In some embodiments, the adjuvant comprises lecithin. In some embodiments, the adjuvant comprises alum. In some embodiments, the adjuvant comprises saponin, cholesterol and phospholipid. In some embodiments, the adjuvant comprises ISCOMATRIX™. In some embodiments, the adjuvant comprises carbomer homopolymer and lecithin. In some embodiments, the adjuvant comprises Adjuplex™.

In some embodiments, an immunogenic composition described herein is capable of eliciting a V2-apex specific anti-HIV Env response. In some embodiments, an immunogenic composition described herein is capable of eliciting a neutralizing anti-HIV response. In some embodiments, an immunogenic composition described herein is capable of eliciting a V2-apex specific anti-HIV Env response in a human subject. In some embodiments, an immunogenic composition described herein is capable of eliciting the production of an antibody that binds to V2-apex of HIV Env. In some embodiments, an immunogenic composition described herein is capable of eliciting the production of a broadly neutralizing antibody in a subject.

In one aspect, provided herein are liposomes comprising an HIV Env polypeptide described herein.

Compositions described herein comprising a polypeptide described herein are intended for prevention and treatment of HIV infection. In some embodiments, compositions described herein (e.g., immunogenic composition) are for eliciting an immune reaction in a subject against HIV. In some embodiments, compositions described herein (e.g., immunogenic composition) are for eliciting a protective immune reaction in a subject against HIV.

In further embodiments of the present disclosure, a composition comprising a polypeptide described herein can additionally be combined with other compositions for the treatment of HIV infection or the prevention of HIV transmission.

In some embodiments, a polypeptide described herein can be administered within a pharmaceutically acceptable diluent, carrier, or excipient, in unit dose form. Conventional pharmaceutical practice can be employed to provide suitable formulations or compositions for administration to individuals. In some embodiments, the administration is prophylactic. Any appropriate route of administration can be employed, for example, administration can be parenteral, intravenous, intra-arterial, subcutaneous, intramuscular, intraperitoneal, intranasal, aerosol, suppository, oral administration, vaginal, or anal.

In some embodiments, the polypeptides and polynucleotides described herein are administered as a component of an immunogenic composition comprising the polypeptides and/or polynucleotides described herein in admixture with a pharmaceutically acceptable carrier. The immunogenic compositions described herein are useful to stimulate an immune response against HIV-1 and can be used as one or more components of a prophylactic or therapeutic vaccine against HIV-1 for the prevention, amelioration or treatment of AIDS. The polynucleotides and vectors described herein are particularly useful for providing genetic vaccines, i.e. vaccines for delivering the polynucleotides encoding the antigenic polypeptides described herein to a subject, such as a human, such that the antigenic polypeptides are then expressed in the subject to elicit an immune response.

In some embodiments, immunogenic compositions described herein comprise injectable suspensions, solutions, sprays, lyophilized powders, syrups, elixirs and the like. Any suitable form of composition can be used. To prepare such a composition, a polypeptide and/or polynucleotide described herein, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol. In some embodiments, immunogenic compositions described herein are formulated in the form of an oil-in-water emulsion. In some embodiments, the oil-in-water emulsion is based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. In some embodiments, the oil is used in combination with an emulsifier to form the emulsion. In some embodiments, the emulsifier comprises a nonionic surfactant, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. In some embodiments, the adjuvant can be a mixture of emulsifier(s), micelle-forming agent, and oil such as that which is commercially available under the name Provax® (IDEC Pharmaceuticals, San Diego, CA). (PEG).

In some embodiments, an immunogenic composition described herein comprises additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

In some embodiments, an immunogenic composition described herein comprises an adjuvant. Suitable adjuvants include, but are not limited to, mineral salts (e.g., AlK(SO$_4$)$_2$, AlNa(SO$_4$)$_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC3 1; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, AK. et al (2004) 22(13-14): 1791-8), and the CCR5 inhibitor CMPD167 (see Veazey, R S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-a, IFN-, and IFN-y (Boyer et al., (2002) J. Liposome Res. 121:137-142; WOOl/095919), immunoregulatory proteins such as CD40L (ADX40; see, for example, WO03/063899), and the CD1a ligand of natural killer cells (also known as CRONY or a-galactosyl ceramide; see Green, T. D. et al, (2003) J. Virol. 77(3): 2046-2055), immunostimulatory fusion proteins such as IL-2 fused to the Fe fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens described herein or on separate expression vectors. In some embodiments, the adjuvant comprises lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced Bio-Adjuvants (ABA)).

In some embodiments, an immunogenic composition described herein is formulated to introduce the polypeptides and polynucleotides disclosed herein (collectively, the immunogens) to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Pharmaceutical compositions described herein can be, for example, in unit dose form, such as in the form of ampoules, vials, suppositories, tablets, pills, or capsules. The formulations can be administered to human individuals in therapeutically or prophylactic effective amounts (e.g., amounts which prevent, eliminate, or reduce a pathological condition) to provide therapy or prophylaxis for a disease or condition (e.g., HIV infection). The preferred dosage of therapeutic or prophylactic agent to be administered is likely to depend on such variables as the type and extent of the disorder, the overall health status of the particular patient, the formulation of the compound excipients, and its route of administration. Suitable dosages of the polypeptides and polynucleotides disclosed herein (collectively, the immunogens) in the immunogenic composition disclosed herein can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

VI. Uses and Methods

Therapeutic Uses and Methods:

In one aspect, provided herein are methods for eliciting an immune response to HIV Env gp120 in a subject, comprising administering to the subject an effective amount of an immunogenic composition described herein, thereby generating the immune response. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition comprises an HIV Env polypeptide described herein. In some embodiments, the immunogenic composition comprises an HIV Env trimer described herein. In some embodiments, the immunogenic composition comprises a nanoparticle described herein. In some embodiments, the immunogenic composition comprises a nucleic acid described herein. In some embodiments, the immunogenic composition comprises more than one (for example, 2, 3, 4, or 5) HIV Env polypeptides (e.g., HIV Env trimer or nanoparticle) described herein. In some embodiments, the pharmaceutical composition comprises a recombinant virus described herein. In some embodiments, an immunogenic composition further comprises an adjuvant. In some embodiments, the immunogenic composition is formulated for subcutaneous administration. In some embodiments, the immunogenic composition is formulated for intramuscular administration.

In one aspect, provided herein are methods of reducing the likelihood of HIV infection in a subject exposed to HIV comprising administering to the subject an effective amount of an immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition comprises an HIV Env polypeptide described herein. In some embodiments, the immunogenic composition comprises an HIV Env trimer described herein. In some embodiments, the immunogenic composition comprises a nanoparticle described herein. In some embodiments, the immunogenic composition comprises a nucleic acid described herein. In some embodiments, the immunogenic composition comprises more than one (for example, 2, 3, 4, or 5) HIV Env polypeptides (e.g., HIV Env trimer or nanoparticle) described herein. In some embodiments, the pharmaceutical composition comprises a recombinant virus described herein. In some embodiments, an immunogenic composition further comprises an adjuvant. In some embodiments, the immunogenic composition is formulated for subcutaneous administration. In some embodiments, the immunogenic composition is formulated for intramuscular administration.

In one aspect, provided herein are methods of reducing the risk of a subject becoming infected with HIV comprising administering to the subject in need thereof an effective amount of an immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition comprises an HIV Env polypeptide described herein. In some embodiments, the immunogenic composition comprises an HIV Env trimer described herein. In some embodiments, the immunogenic composition comprises a nanoparticle described herein. In some embodiments, the immunogenic composition comprises a nucleic acid described herein. In some embodiments, the immunogenic composition comprises more than one (for example, 2, 3, 4, or 5) HIV Env polypeptides (e.g., HIV Env trimer or nanoparticle) described herein. In some embodiments, the pharmaceutical composition comprises a recombinant virus described herein. In some embodiments, an immunogenic composition further comprises an adjuvant. In some embodiments, the immunogenic composition is formulated for subcutaneous administration. In some embodiments, the immunogenic composition is formulated for intramuscular administration.

In one aspect, provided herein are methods of preventing HIV infection comprising administering to a subject in need thereof an effective amount of the immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition comprises an HIV Env polypeptide described herein. In some embodiments, the immunogenic composition comprises an HIV Env trimer described herein. In some embodiments, the immunogenic composition comprises a nanoparticle described herein. In some embodiments, the immunogenic composition comprises a nucleic acid described herein. In some embodiments, the immunogenic composition comprises more than one (for example, 2, 3, 4, or 5) HIV Env polypeptides (e.g., HIV Env trimer or nanoparticle) described herein. In some embodiments, the pharmaceutical composition comprises a recombinant virus described herein. In some embodiments, an immunogenic composition further comprises an adjuvant. In some embodiments, the immunogenic composition is formulated for subcutaneous administration. In some embodiments, the immunogenic composition is formulated for intramuscular administration.

In one aspect, provided herein are methods of treating HIV/AIDS comprising administering to a subject in need thereof an effective amount of the immunogenic composition described herein, or the pharmaceutical composition described herein. In some embodiments, the subject is a human. In some embodiments, the subject has been exposed to HIV. In some embodiments, the subject is at risk of being exposed to HIV. In some embodiments, the subject at risk of being exposed to HIV is a health care worker, a sexual partner of an HIV infected individual, or a sex worker. In some embodiments, the subject is a non-human primate. In some embodiments, the immunogenic composition comprises an HIV Env polypeptide described herein. In some embodiments, the immunogenic composition comprises an HIV Env trimer described herein. In some embodiments, the immunogenic composition comprises a nanoparticle described herein. In some embodiments, the immunogenic composition comprises a nucleic acid described herein. In some embodiments, the immunogenic composition comprises more than one (for example, 2, 3, 4, or 5) HIV Env polypeptides (e.g., HIV Env trimer or nanoparticle) described herein. In some embodiments, the pharmaceutical composition comprises a recombinant virus described herein. In some embodiments, an immunogenic composition further comprises an adjuvant. In some embodiments, the immunogenic composition is formulated for subcutaneous administration. In some embodiments, the immunogenic composition is formulated for intramuscular administration.

In some embodiments, a method disclosed herein comprises administering two or more of the HIV Env polypeptides disclosed herein. In some embodiments, each of the two or more HIV Env polypeptides comprises a V2 apex epitope of ZM233 trimer. In some embodiments, two or more different HIV Env polypeptides are administered. In some embodiments, the HIV Env polypeptides are administered sequentially. In some embodiments, the HIV Env polypeptides are administered together. In some embodiments, the two or more HIV Env polypeptides are administered with an adjuvant.

In some embodiments, the immunogenic composition comprises an isolated polypeptide described herein. In some embodiments, the immunogenic composition comprises an HIV Env trimer described herein. In some embodiments, the immunogenic composition comprises a nanoparticle described herein. In some embodiments, the immunogenic composition comprises a nucleic acid described herein. In some embodiments, the immunogenic composition comprises more than one (for example, 2, 3, 4, or 5) HIV Env polypeptides (e.g., HIV Env trimer or nanoparticle) described herein. In some embodiments, the pharmaceutical composition comprises a recombinant virus described herein. In some embodiments, the immunogenic composition comprises an isolated polypeptide described herein. In some embodiments, the immunogenic composition comprises an HIV Env trimer described herein. In some embodiments, the immunogenic composition comprises a nanoparticle described herein. In some embodiments, the immunogenic composition comprises a nucleic acid described herein. In some embodiments, the pharmaceutical composition comprises a recombinant virus described herein. In some embodiments, an immunogenic composition further comprises an adjuvant. In some embodiments, the immunogenic composition is formulated for subcutaneous administration. In some embodiments, the immunogenic composition is formulated for intramuscular administration.

In some embodiments, a method described herein further comprises administering at least one additional therapeutic agent. In some embodiments, the additional therapeutic agent is an antiretroviral agent. In some embodiments, the additional therapeutic agent comprises an antiretroviral therapy (ART) agent, a reservoir activator, an immuno-modulator, a second antibody, or a broadly neutralizing anti-BIV antibody.

In one embodiment, the administering to the subject is by at least one mode selected from oral, parenteral, subcutane-ous, intramuscular, intravenous, vaginal, rectal, buccal, sub-lingual, and transdermal.

In certain embodiments, the subject is at risk for exposure to HIV. In some embodiments, the subject is infected with HIV. In some embodiments, the subject is diagnosed with AIDS. In certain embodiments, the subject at risk for exposure to HIV is a health care worker. In certain embodi-ments, the subject at risk for exposure to HIV is a sex worker. In certain embodiments, the subject at risk for exposure to HIV is a sexual partner of an HIV infected individual. In certain embodiments, the subject at risk for exposure to HIV is a newborn.

In some embodiments, the polypeptides and/or polynucle-otides described herein are administered in vivo, for example where the aim is to produce an immunogenic response in a subject. In some embodiments, the "subject" may be any animal. In some embodiments, it will be desirable to express the antigens described herein in human subjects, such as in clinical trials and for actual clinical use of the immunogenic compositions and vaccine of the inven-tion. In some embodiments, the subject is a human, for example a human that is infected with, or is at risk of infection with, HIV-1.

For such in vivo applications the polypeptides and/or polynucleotides described herein can be administered as a component of an immunogenic composition comprising the polypeptides and/or polynucleotides described herein in admixture with a pharmaceutically acceptable carrier. The immunogenic compositions described herein are useful to stimulate an immune response against HIV-1 and can be used as one or more components of a prophylactic or therapeutic vaccine against HIV-1 for the prevention, ame-lioration or treatment of AIDS. The polynucleotides described herein are particularly useful for providing genetic vaccines, i.e. vaccines for delivering the polynucleotides encoding the polypeptides described herein to a subject, such as a human, such that the polypeptides are then expressed in the subject to elicit an immune response.

When provided prophylactically, the immunogenic com-positions described herein can be administered to a subject in advance of HIV infection, or evidence of HIV infection, or in advance of any symptom due to AIDS, especially in high-risk subjects. The prophylactic administration of the immunogenic compositions described herein can serve to provide protective immunity of a subject against HIV-1 infection or to prevent or attenuate the progression of AIDS in a subject already infected with HIV-1. When provided therapeutically, the immunogenic compositions described herein can serve to ameliorate and treat AIDS symptoms and can be used as soon after infection as possible, for example, before appearance of any symptoms of AIDS, but can also be used at (or after) the onset of the disease symptoms.

Immunization schedules (or regimens) are well known for animals (including humans) and can be readily determined for the particular subject and immunogenic composition. Hence, the immunogens can be administered one or more times to the subject. In some embodiments, there is a set time interval between separate administrations of the immu-nogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immuno-genic composition, but can have as few as one or two or four. The methods of inducing an immune response described herein can also include administration of an adjuvant with the immunogens. In some instances, annual, biannual or other long interval (5-10 years) booster immunization can supplement the initial immunization protocol.

The methods described herein also include a variety of prime-boost regimens. In these methods, one or more prim-ing immunizations are followed by one or more boosting immunizations. The actual immunogenic composition can be the same or different for each immunization and the type of immunogenic composition (e.g., containing protein or expression vector), the route, and formulation of the immu-nogens can also be varied. For example, if an expression vector is used for the priming and boosting steps, it can either be of the same or different type (e.g., DNA or bacterial or viral expression vector). In some embodiments, the prime-boost regimen provides for two priming immuniza-tions, four weeks apart, followed by two boosting immuni-zations at 4 and 8 weeks after the last priming immunization. It should also be readily apparent to one of skill in the art that there are several permutations and combinations that are encompassed using a polypeptide (e.g., Env trimer or nan-oparticle) described herein to provide priming and boosting regimens.

In some embodiments, a method of inducing an immune response against HIV in a subject described herein com-prises administering an immunogenic composition of the invention comprising an adenovirus vector containing DNA encoding one or more of the polypeptides described herein, one or more times to a subject wherein the polypeptides are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequen-tially administered, with other HIV immunogens and/or HIV immunogenic compositions, e.g., with "other" immunologi-cal, antigenic or vaccine or therapeutic compositions thereby providing multivalent or "cocktail" or combination compo-sitions. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In some embodiments, the other HIV immunogen is Env, for example, an HIV Env trimer.

Immunogen Design

Provided herein are methods for identifying immunogens capable of eliciting a V2 epitope specific broadly neutraliz-ing antibody (bnAb) response in a subject (e.g., a human subject).

In one aspect, provided herein are methods for vaccine candidate HIV Env polypeptides (e.g., HIV Env trimers), the method comprising providing a library comprising a plural-ity of HIV Env polypeptides; contacting the library with a germline or germline reverted HIV broadly neutralizing antibody (bnAb) directed to the V2 apex region of HIV envelope; identifying a donor HIV Env polypeptide that specifically binds to the antibody, and generating a plurality of chimeric Env polypeptides comprising a backbone and the V1V2 region of the donor HIV Env polypeptide. In some embodiments, the library comprises a plurality of variant HIV Env polypeptides comprising one or more substitutions in the V1V2 region. In some embodiments, the germline or germline reverted bnAb is CAP256 UCA, PG9 iGL, CH01 iGL, or PGT145 iGL. In some embodiments, the germline or germline reverted bnAb is CH01 iGL. In some embodiments, the backbone comprises a BG505, ZM197, or CFR250 HIV Env backbone. In some embodiments, the V1V2 region of the donor HIV Env polypeptide comprises the amino acid residues corresponding to positions about 131 to about 196, wherein the HIV Env polypeptide positions correspond to the HXB2 reference (SEQ ID NO: 1). In some embodiments, the chimeric Env polypeptides lack glycan sequons at N156 and N130, wherein the HIV Env polypeptide positions correspond to the HXB2 reference (SEQ ID NO: 1).

In one aspect, provided herein are methods for engineering an immunogen capable of eliciting a broadly neutralizing antibody (bnAb) against a V2 epitope of an HIV virus which comprises a) identifying a V2 epitope conserved across two different HIV viruses, b) selecting or designing an antibody that binds to the epitope, and c) designing an immunogen that comprises the V2 epitope and binds to the germline or germline reverted antibody. In some embodiments, the antibody is a germline antibody. In some embodiments, the method comprises engineering the V2 epitope to improve binding of the V2 epitope to the germline or germline reverted antibody. In some embodiments, the designing the immunogen comprises substituting an amino acid in the immunogen.

In one aspect, provided herein are methods for identifying an HIV binder which comprises contacting a candidate binder with an HIV Env polypeptide described herein and identifying a candidate binder that binds to the HIV Env polypeptide.

In one aspect, provided herein are methods for identifying a broadly neutralizing antibody (bnAb) against HIV which comprises contacting a candidate antibody with an HIV Env polypeptide described herein and identifying an antibody that binds to the HIV Env polypeptide as a bnAb. In some embodiments, the bnAb is a germline or germline reverted bnAb.

Embodiments of the present disclosure can be further defined by reference to the following non-limiting examples, which describe in detail materials and methods of the present disclosure. It will be apparent to those skilled in the art that many modifications, both to materials and methods, can be practiced without departing from the scope of the present disclosure.

All documents, patent, and patent applications cited herein are hereby incorporated by reference, and may be employed in the practice described herein.

EXAMPLES

Experimental Design

Induction of HIV protective broadly neutralizing antibodies (bnAbs), i.e. Abs that neutralize multiple global isolates, will likely be a key feature of a prophylactic HIV vaccine. BnAbs to HIV envelope (Env) trimer protein are produced over time in a subset of infected donors in natural infection but their elicitation through vaccination has so far proved elusive (reviewed in (Burton and Hangartner, 2016; Escolano et al., 2017; Kwong and Mascola, 2018). In natural infection, bnAbs are produced through highly intricate B cell maturation pathways (Bonsignori et al., 2016; Doria-Rose et al., 2014; Landais et al., 2017; Liao et al., 2013; MacLeod et al., 2016). The complex nature of the HIV Env surface, densely packed with glycans, means that bnAbs must incorporate multiple features in their variable (V) domains, such as high levels of somatic hypermutation (SHM), insertions and deletions (indels) and long CDRH3s, to navigate the glycans and access small islands of relatively conserved protein surface underneath (Crispin et al., 2018; Mascola and Haynes, 2013; West et al., 2012). Of note, bnAb precursors are often very rare meaning that the initiation of bnAb responses is often a severe bottleneck (Briney et al., 2012; Kepler and Wiehe, 2017; West et al., 2012). The need for a B cell receptor (BCR) to then accumulate extraordinary levels of secondary modifications that include high-levels of SHM and/or indels to acquire neutralization breadth is then a further barrier to bnAb development (Kelsoe and Haynes, 2017; Kepler et al., 2014; Klein et al., 2013; Victora and Mouquet, 2017). Overall, this is has led to a consensus (Andrabi et al., 2018; Escolano et al., 2017; Haynes and Mascola, 2017; Kwong and Mascola, 2018; Sanders and Moore, 2017; Williams et al., 2017) that the route to the induction of bnAbs lies through a sequential multi-immunogen vaccination process. Such a sequential strategy has been shown successful for V3-glycan bnAbs (Escolano et al., 2017; Steichen et al., 2016) and partially successful for VRC01-class CD4 binding site (CD4bs) bnAbs in engineered mice (Briney et al., 2016; Dosenovic et al., 2015; Jardine et al., 2015; McGuire et al., 2013; Stamatatos et al., 2017; Tian et al., 2016). This work, and other work on HIV Env trimers (Andrabi et al., 2015; Gorman et al., 2016; Pauthner et al., 2017; Sanders et al., 2015), has helped to bring a number of immunogens based on sequential strategies to the stage of manufacturing and to entering the clinic.

A recognized challenge in inducing bnAbs is to design strategies that can guide an immunofocused response to a bnAb epitope and reduce off-target B cell responses. The virus has clearly evolved immunodominance (Havenar-Daughton et al., 2017) as a mechanism to encourage non-functional Ab responses at the expense of relatively immunoquiescent bnAb responses. Multiple strategies are being employed to reduce non-desirable Ab responses (Burton and Hangartner, 2016; Sok et al., 2013). These include designs that specifically sequester non-desired immunodominant B cell epitopes (de Taeye et al., 2015; Kulp et al., 2017). Another approach uses the immunization protocol itself to minimize off-target responses (Havenar-Daughton et al., 2017; Silva et al., 2017; Victora and Wilson, 2015). Using this type of approach in a sequential HIV Env immunization strategy means that each immunization must generate a sufficient population of memory B cells to be activated and expanded by the next immunogen in the sequence (Andrabi et al., 2018; Briney et al., 2016; Burton, 2017; Escolano et al., 2016; Li et al., 2012; Steichen et al., 2016; Victora and Mouquet, 2017). In this case, affinity distances between sequentially administered immunogens becomes a critical consideration and must be optimally regulated to efficiently recall an Ab response but sufficient to drive further affinity maturation (Abbott et al., 2018; Batista and Neuberger, 1998; Dosenovic et al., 2018; Victora and Mouquet, 2017). Overall, design strategies that can select rare bnAb precursors, reduce off-target responses and effectively recall epitope-specific B cells at secondary immunization may be needed to drive a B cell response towards a desired bnAb epitope.

In this study, we have investigated the conditions for initiating and propagating a V2-apex nAb response in an animal model. BnAbs target a number of sites on HIV (Escolano et al., 2017; Kwong and Mascola, 2018; McCoy and Burton, 2017) that have both advantages and disadvantages from a vaccine-targeting standpoint. A popular target is the V2-apex that is well-exposed at the "top" of the Env trimer and is typically recognized by a substantial proportion of HIV-infected individuals who develop bnAbs responses (Georgiev et al., 2013; Landais et al., 2016; Walker et al., 2010). The bnAb-site is formed by a patch of positively charged lysine-rich residues surrounded by glycans at the 3-fold axis of Env trimer (Andrabi et al., 2017; Andrabi et al., 2015; Gorman et al., 2016; Lee et al., 2017; McLellan et al., 2011). In attempts to guide an epitope-focused nAb response to an HIV bnAb-site, we previously immunized rabbits with native Env trimer immunogens that bind to inferred germline (iGL) versions of V2-apex bnAbs (Andrabi et al., 2015; Gorman et al., 2016; Voss et al., 2017). Repeated immunizations with the individual V2-apex iGL binding trimers in rabbits produced V2-specific nAb responses whose reproducibility varied markedly for each immunogen (Voss et al., 2017). Surprisingly, in sequential and cocktail immunization strategies, with differing immunogens that are thought to be critical for expansion of neutralization breadth, the protocol failed to induce V2-specific nAb responses at all despite the cross-reactive binding and neutralization by V2-apex bnAb prototypes of the Env immunogens used (Andrabi et al., 2015; Voss et al., 2017). This result was particularly surprising as the immunogens used in the sequential and cocktail immunization strategies included Env trimers that successfully induced V2-apex nAb responses when administered repeatedly as individual trimers. To understand the immunological basis for this failure to induce nAb responses, we hypothesized that the differences in the sequences of the bnAb epitopes regions on these sequential immunogens could potentially create affinity gaps that may contribute to failure of an antibody recall response.

To reproducibly initiate and expand a V2-apex specific nAb response, we engrafted a common V1V2 loop on three distinct Env backbones to generate chimeric HIV Env trimer immunogens. Like their parental Envs, the soluble chimeric V1V2 trimers showed native-like properties and bound V2 apex bnAbs, their iGL versions and bnAbs targeting other Env epitopes. Immunization in rabbits using sequential and cocktail strategies produced potent immunofocused nAb responses that were highly reproducible and largely mapped to the V2-epitope region recognized by human V2-apex bnAbs. We observed quantitative and qualitative differences between the two immunization schemes, sequential being superior at the primary response level. However, the responses equalized across the two groups as the immunization progressed to the secondary boosting stages. Overall, the study demonstrates how rational vaccine focusing can drive deterministic B cell selection to a complex antigen surface to favor an epitope directed nAb responses and the approach may be highly useful to harness vaccine strategies to induce bnAbs in humans. We further propose that these immunofocusing strategies may have broad implications to design robust vaccines against complex pathogen surfaces

Example 1. Design of Chimeric V1V2 Trimers and Immunofocusing

As above, an earlier study (Voss et al, 2017) showed that nAbs could be induced by multiple immunizations with the same Env trimers that bound iGL versions of V2-apex bnAbs and had a glycan hole near the apex of the trimer. However, immunization schedules employing trimers in sequence or in cocktails generally failed to induce nAbs. This observation was not due to the lack of a common T-cell helper epitope amongst the trimers since non-neutralizing serum Ab responses did display cross-reactive Env binding activity. We hypothesized, the failure to recall nAb responses when boosting with a different Env trimer may arise from an "affinity gap" between successive immunogens due to the inherent sequence variability of the HIV bnAb epitopes across the sequentially administered trimer immunogens. Indeed, sequence analysis of the V2-apex iGL binding trimers used in the Voss et. al study revealed considerable sequence variability within and around the V2-apex bnAb epitope. This variability was particularly a result of variation in the length of hypervariable regions (V1'-HXB2-133-150 and V2'-185-191) and the number and positioning of the V1' glycans. These features may orient the V1V2 loops of the individual trimer immunogens into differing conformations and thus affect their affinities for the relevant BCRs and ability to particularly recall an epitope specific B cell response in a sequential immunization scheme.

To overcome this potential B cell recall response problem, we sought to optimize trimer design and/or strategies that could specifically help recall an epitope-focused antibody response to a bnAb epitope in a multi-stage immunization scheme. We homogenized the V2-apex bnAb epitope on multiple trimer immunogens using the SOSIP.664 soluble trimer design platform (Pugach et al., 2015; Sanders et al., 2013; Sanders and Moore, 2017). We generated chimeric trimers by engrafting a common V1V2 loop from ZM233 Env onto three different HIV Env backbones, ZM197, CRF250 and BG505, which have been previously shown to form well-ordered soluble trimers (FIG. 1A-B) (Andrabi et al., 2015; Julien et al., 2015; Sanders et al., 2013). The basis for using a common V1V2 sequence on diverse HIV envelope backbones was to retain the same bnAb epitope that could be repeatedly presented to an animal's immune system through sequential immunizations to improve affinity. Subsequently, this immunization scheme, by conserving the same bnAb epitope should not only help in recalling a V2-apex specific neutralizing B cell response but also facilitate immunofocusing by reducing germinal center competition between the common V1V2 neutralizing epitope and other Env-backbone epitopes on sequential immunogens (Wang et al., 2015).

The ZM233 V1V2 sequence was selected based on its reactivity with inferred germline precursor versions of three V2-apex bnAb prototypes and hence its potential application for inducing bnAbs in humans (Andrabi et al., 2015; Bonsignori et al., 2011; Gorman et al., 2016; Pancera et al., 2010). Unlike the other V2-apex iGL binding trimers that possess a glycan hole formed by missing glycans in the hypervariable-2 region and at position N130 (Andrabi et al., 2015; Voss et al., 2017), the ZM233V1V2 loop glycan hole is created solely by glycans lacking at N130 and N156 positions that presumably enable V2-apex iGL Abs to access the core epitope lysine-rich region. We did attempt engrafting V1V2 loops from a number of HIV Env isolates that bind to the V2-apex bnAb iGL Abs (Andrabi et al., 2015), however, only ZM233V1V2 yielded stable trimers on three distinct Env backbones, with favorable antigenic profiles. Therefore, we pursued the chimeric ZM233V1V2 trimers for further characterization. The advantage of having a common V1V2 loop on multiple Env immunogens would not only enable to assess their ability to recall the epitope specific B cells at boosting but presumably also improve their capability to recruit these responses at the secondary boost immunization (Wang et al., 2015).

The ZM233V1V2 chimeric trimer constructs were expressed in HEK293F cells and yielded well-assembled trimer proteins when purified with a PGT145 Ab affinity column (FIG. 1C). The trimers, like their parental wild-type sequences, were efficiently cleaved and adopted native-like conformations as determined by negative stain electron microscopy (NS-EM) (FIG. 1D-E). These trimers exhibited a high proportion of high-mannose glycans, a characteristic property of native-like soluble Env trimers (Behrens et al., 2016; Bonomelli et al., 2011; Cao et al., 2017; Pritchard et al., 2015). Further, we assessed the binding of V2-apex prototype bnAbs and their germline versions to these chimeric ZM233V1V2 trimers and observed a strong binding in ELISA (FIG. 1F). Interestingly, despite having a common V1V2 sequence (that mainly forms the V2-apex epitope) on different Env backbones, the binding efficiency of the V2-apex iGL Abs to chimeric trimers varied (FIG. 1F). The iGL Abs bound more strongly to ZM233V1V2 chimeric trimer with ZM197 Env backbone than to chimeras with CRF250 or BG505 backbones. This differential binding of V2-apex iGL Abs to chimeric trimers could be a result of the V2-apex epitope exposure on a given chimeric trimer but also highlights the role of additional residues outside of the V1V2 loops that could potentially modulate binding by iGL Ab prototypes. Further, antigen profiling with a range of bnAbs and non-neutralizing Abs (non-nAbs) that represent various specificities on HIV Env showed overall a strong binding with bnAbs and no or weak binding with non-nAbs suggesting that the antigenicity of the chimeric V1V2 trimers was not compromised.

Overall, we successfully designed chimeric V1V2 Env trimers that retain all native-like properties, bind to the iGLs of V2-apex bnAbs and could potentially guide an immuno-focused response to the V2-apex site.

Figure 2:
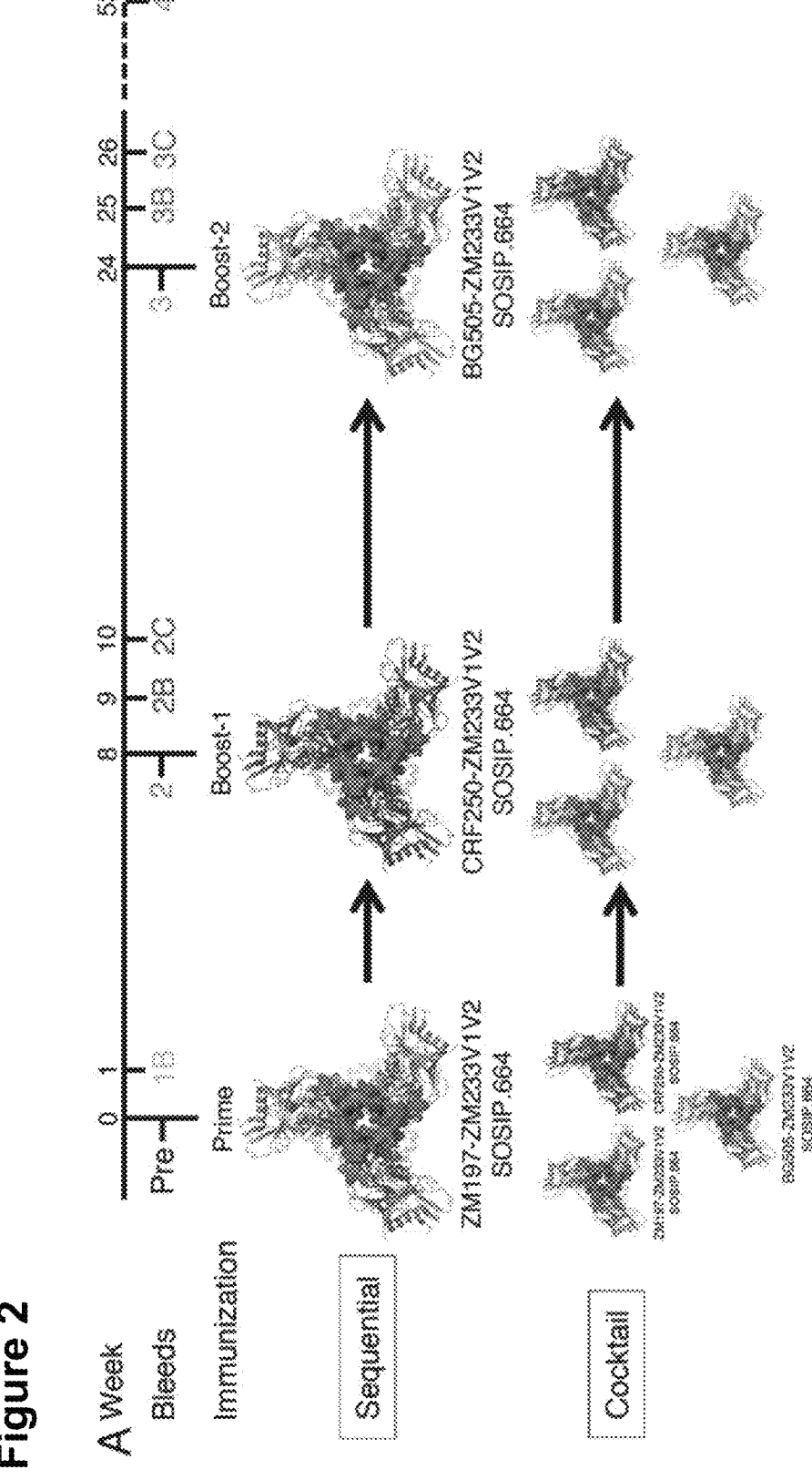
FIG. 2. ZM233V1V2 chimeric trimer immunizations in rabbits and neutralizing Ab responses. A. Schematic showing schedules of sequential and cocktail immunization strategies with chimeric ZM233V1V2 timer immunogens. Two groups of 4-rabbits each were immunized with 50 ug of individual trimer (sequential) or a 3-trimer cocktail (50 ug total) along with the Iscomatrix adjuvant (100 units/dose). The immunogens were administered intra-muscularly (IM) into to each animal and the immunization and bleed time points are indicated. B. Neutralization titrations for pre- (black) and post-bleed immune serum IgG samples at time points as indicated in A. 3-fold diluted immune serum IgG samples (IgG concentration range=1-300 ug/ml) were tested against the ZM233 virus in a TZM-bl reporter cell assay and the neutralizing activities are plotted as percent neutralization. C. Neutralization of ZM233 WT (above), chimeric BG505-ZM233V1V2 and BG505 WT viruses by serum IgG was carried out in the TZM-bl assay and IC50 neutralization titers represent the serum IgG concentration at which 50% reduction in the virus infectivity was achieved. D. Correlation of IC50s of ZM233 WT virus and BG505-ZM233 virus neutralization using serum IgG from sequential and cocktail immunization schedules. Spearman correlation coefficients and p-values are indicated.
Figure 2:
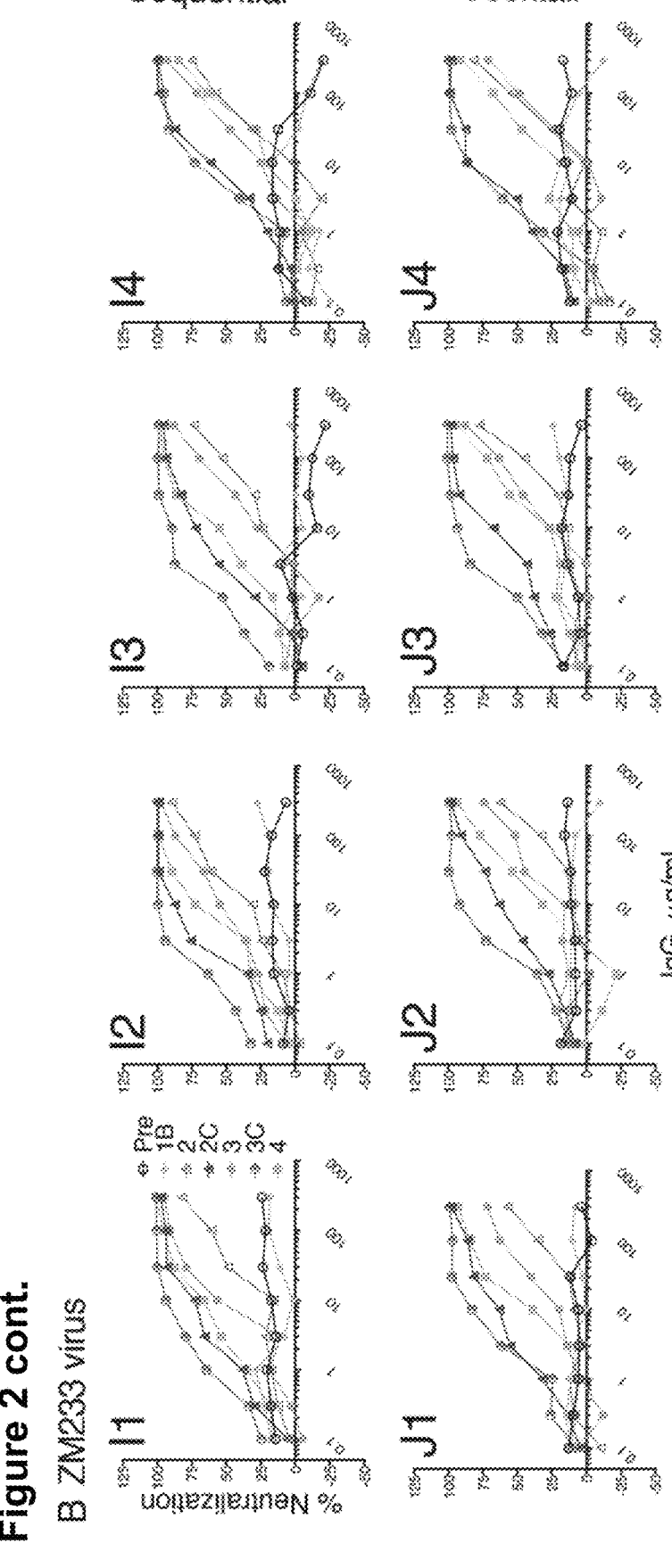

Example 2. Chimeric ZM233V1V2 Trimer Immunogens Induce a Highly Reproducible V1V2-Epitope Focused nAb Response in Rabbits To assess whether the chimeric ZM233V1V2 trimer immunogens can guide a V1V2-specific nAb response in a multi-stage immunization scheme, we immunized 2 groups of New Zealand white rabbits, each group receiving either individual ZM233V1V2 chimeric trimers, sequentially or a cocktail of 3-timers simultaneously, using immunization schemes depicted in FIG. 2A. We chose rabbit as a model to test this immunofocusing vaccine concept, as previous studies have shown the V2-apex region as an immunodominant B cell epitope in the rabbit B cell response and that the sequential and cocktail immunizations with heterologous HIV Envs bearing divergent V1V2 loops have failed to induce a nAb response to this site (Voss et al., 2017). We intra-muscularly (IM) administered 50 g dose of the individual chimeric trimer (sequential) or a 3-trimer cocktail (cocktail) immunogens at 0, 8 and 24 weeks along with 100-units of Iscomatrix as adjuvant (FIG. 2A).

To assess the virus neutralizing ability of the elicited Ab responses, we examined polyclonal serum purified IgG samples from various immunization time points. To specifically probe the presence of V1V2-specific nAb responses, we first tested the serum IgGs for neutralization against the WT-ZM233 Env encoding virus, whose V1V2 region was part of the chimeric trimer immunogens and any neutralizing activities against this virus should presumably reflect responses directed to V1V2-loops. The neutralization titrations of the serum IgG samples with ZM233 virus reveal the induction of a nAb response at primary immunization and its development through secondary boosting stages (FIG. 2B). Interestingly, the nAb responses appeared as early as 2 months post-prime, prior to the second immunization (boost-1), suggesting the immunogens successfully triggered V2-epitope specific B cell responses (FIG. 2B). At this stage, the nAb titers were marginally superior in the sequential compared to the cocktail immunization group. Post boost-1 immunization, the nAb levels sharply increased and the titers were orders of magnitude higher compared to the primary immune responses suggesting a successful Ab recall response. The nAb levels further elevated post boost-2 immunization and the titers became comparable between sequential and cocktail immunization groups (FIG. 2B).

To further confirm the V1V2-directed specificities of these immune responses, we examined the neutralizing activities of the serum IgGs with WT-BG505 virus and a chimeric BG505-ZM233V1V2 Env encoding virus variant, in which the V1V2 region was replaced with ZM233 Env-derived V1V2. Except for the post boost-1 (2C) and boost-2 (3B and 3C) time point serum IgGs from the cocktail immunization group, all the serum IgG samples in both groups failed to show any neutralization of the WT-BG505 virus (FIG. 2C). The serum IgGs, however, displayed potent neutralizing activities against the chimeric BG505-ZM233V1V2 virus (FIG. 2C). The neutralizing activities of the serum IgGs against the chimeric ZM233V1V2 virus strongly correlated with those for the WT-ZM233 virus thus further demonstrating that neutralization activities were almost entirely mediated through V1V2-directed nAbs (FIG. 2C, D). The chimeric ZM233V1V2 trimer immunogens in both the sequential and cocktail immunizations produced a highly reproducible epitope-focused potent neutralizing Ab response (FIG. 2B, D). This is in contrast to trimer immunizations previously conducted with heterologous HIV Env trimers that fail or poorly induce consistent epitope-focused nAb responses in sequential and cocktail immunization strategies (Klasse et al., 2016; Torrents de la Pena et al., 2018; Voss et al., 2017). These epitope-specific nAb titers were superior to those reported in earlier studies and the animals sustained significant levels of nAb titers even 6-months post boost-2 immunization demonstrating the robust durability of the responses (de Taeye et al., 2015; Klasse et al., 2018; Klasse et al., 2016; Sanders et al., 2015; Torrents de la Pena et al., 2018; Torrents de la Pena et al., 2017; Voss et al., 2017). Therefore, the strategy to engraft a common bnAb encoding regions on multiple Envs guides an immunofocused neutralizing antibody response and effectively encourages an Ab recall response.

To evaluate the neutralization breadth of these serum immune responses, we tested in neutralization the 14-days post boost-2 (3C) IgG samples with Env isolates representing global HIV diversity (deCamp et al., 2014). The IgGs displayed sporadic neutralizing activities with easy-to-neutralize tier 1 or 1B viruses on this panel but failed to neutralize more resistant tier 2 or 3 viruses. We also assessed neutralizing activities of the primary and secondary immune IgG samples against tier 1, MW965 (subtype C), SF162 and SS1196 (subtype B) viruses that are generally reflective of V3-specific neutralizing Ab responses that do not neutralize more resistant tier 2 or 3 viruses (Hu et al., 2015; Sanders et al., 2015; Torrents de la Pena et al., 2018; Voss et al., 2017). Both immunization groups developed nAb responses against the MW965 virus but largely failed to neutralize clade B viruses, SS1196 and SF162, albeit few animals that develop nAb responses for SF162 post boost-2 immunization. Notably, compared to previous studies, the SF162-specific nAb titers were lower and only came up late in the immunizations (Sanders et al., 2015; Torrents de la Pena et al., 2018; Voss et al., 2017). The results overall suggest that although these design strategies elicit epitope-focused nAb responses but further trimer boosting strategies will be required to expand the neutralization breadth. Nevertheless, it would also need to be further ascertained whether the failure to induce broad nAb responses in rabbits is due to lack of the long CDRH3 B cell precursors that encode V2-apex bnAb response to this epitope in humans (Briney et al., 2012; Lavinder et al., 2014).

Altogether, we designed trimer immunogens that induce an immunofocused nAb response in rabbits and further successfully recall these responses in a multi-stage vaccine immunization approach. The results overall provide an important example of reproducible elicitation of complex antigen driven bnAb epitope-specific Ab responses in a polyclonal B cell repertoire expressing animal model.

Figure 3:
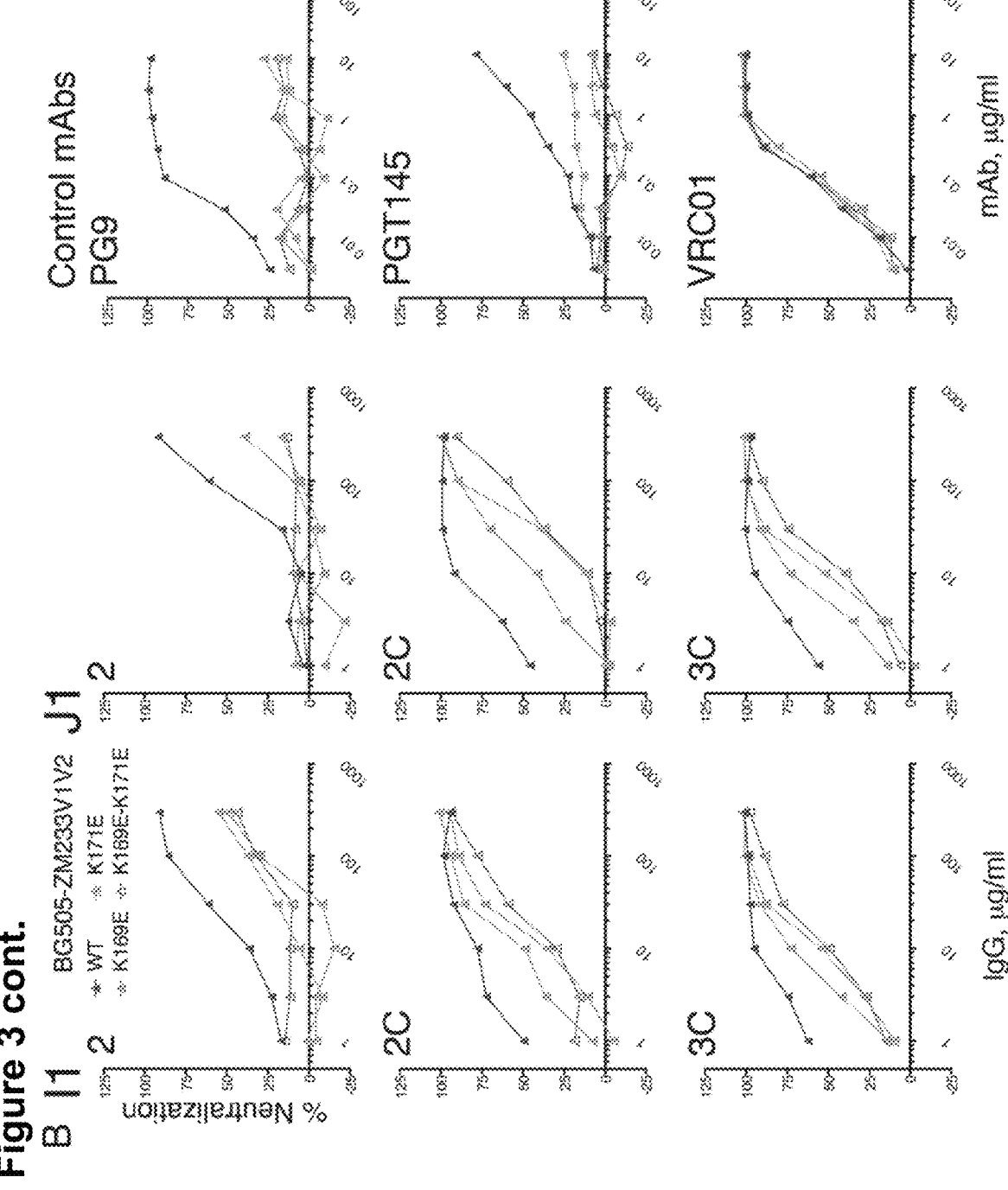
FIG. 3. Fine epitope specificities of the elicited nAb responses. A. IC50 neutralization titers against the BG505-ZM233V1V2 chimeric virus of the serum IgG responses of sequential and cocktail immunization rabbit samples at select time points; pre-bleed (Pre), 8 weeks post prime (2), 2-weeks post boost-1 (2C) and 2 weeks boost-2 (3C) (see FIG. 3A). Fold changes in the IC50 neutralization titers for BG505-ZM233V1V2 K169, K171 and K169/K171residue virus variants are shown. Fold-changes were calculated by (IC50 nAb titers with the virus variant/IC50 nAb titer with the WT-virus) and are shown for each serum IgG sample at different stages of immunization. B. Neutralization titration curves of representative rabbit serum IgG samples from sequential (rabbit I1) and cocktail immunization (rabbit J1) protocols against the BG505-ZM233V1V2 virus and its K-residue variants. The titrations depict changes in the neutralization sensitivities of the neutralizing IgG responses at various stages of immunization. The V2-apex bnAbs (PG9 and PGT145) and a CD4bs directed bnAb (VRC01) were controls for the assay.

Example 3. The Neutralizing Ab Responses Target Strand-C Residues Recognized by Human V2-Apex bnAbs To investigate the fine epitope specificities of the nAb responses targeted we generated strand C variants on BG505-ZM233V1V2 chimeric Env virus (Andrabi et al., 2015; Lee et al., 2017; McLellan et al., 2011; Pancera et al., 2013). We chose to test the fine epitope dependence on chimeric BG505-ZM233V1V2 Env instead of the WT-ZM233 virus, as the strand-C residue substitutions rendered the latter Env pseudovirus variants non-infectious, especially the mutations involving two-amino acid residue substitutions. We examined neutralizing activities by the serum IgGs of all immunization time points against the BG505-ZM233V1V2 chimeric virus and its V2-strand C variants and observed strong dependence, particularly on residues, K169 and K171 that form the core epitope for V2-apex bnAbs (FIG. 3A) (Andrabi et al., 2015). FIG. 3 shows the neutralizing activities of the serum IgG responses of the select samples that represent the primary (2; 2-months post-prime) and the secondary (2B and 2C; 2-weeks post boost-1 and boost-2 respectively) immunization time points (FIG. 3A) and their sensitivity to stand C substitutions.

We further inspected how fine epitope specificities of these nAb responses changed over time at primary and secondary immunization stages. The analysis of the serum IgG responses revealed that the nAb activities in both sequential and cocktail groups were dependent on the V2-strand C K169 and K171 residues, however, the fine specificities differed subtly across these two groups. While nAb responses in sequential immunization group showed relatively more dependence on K171 residue, the cocktail group displayed slightly higher dependence on the K169 residue. Nevertheless, the neutralizing activities of both immunization groups were almost entirely dependent on the K169 and K171 residues at the primary immune response. However, this dependence on the strand-C residues was invariably increased at the boost-1 but diminished substantially, as the immunizations progressed to the boost-2 (FIG. 3A-B). In contrast to the serum nAb responses, in which the neutralizing activities were only partially eliminated upon K-residue substitutions, both individual K169 or K171 substitutions and the double residue variants completely abrogated neutralizing activities of V2-apex bnAbs (FIG. 3B). The results suggest that the early Ab responses focus more on the strand-C residues, however as the immunizations progress, especially after the boost-2, the secondary nAb responses rely less on the strand C K-rich residues. These results suggest that the nAb response at the secondary immune stages either begins to focus on more elements within this bnAb epitope, or probably their dependence spreads to non-strand C residues within the V1V2 loops. Therefore, although a substantial proportion of neutralizing activities came from the core-epitope lysine residues but significant responses targeted outside of these elements suggesting further strategies to funnel responses that are more focused on K-rich residues would be required, especially at the boosting immunization steps.

Overall, the nAb responses targeted the V1V2 loop including regions recognized by human V2-apex bnAbs, although the fine specificities may have marginally differed at the primary and secondary immune responses and across the immunization groups.

Example 4. Specificity of Binding and Neutralizing Ab Responses to the Trimer Immunogen Env-Backbones in Sequential and Cocktail Immunization Strategies Next, we sought to examine the presence of immunogen-backbone specific nAb and non-neutralizing Ab (nnAb) responses across the sequential and cocktail immunization groups and further monitor how these responses changed at primary and secondary immunization stages. To investigate nAb responses, we assessed the neutralizing ability of the serum IgG samples against the immunogen backbone-Env encoding viruses, ZM197, CRF250 and BG505. None of the sequential immunization group rabbits developed immunogen Env backbone nAb activity. In contrast, 4 of 4 and 3 of 4 of the cocktail group rabbits respectively developed nAb responses against CRF250 and BG505 Env backbones post boost-1 immunization and these nAb titers further increased post boost-2 immunization. However, none of the rabbits produced nAb responses against the ZM197 Env backbone. Further mapping of the cocktail group post boost-2 IgG responses with CRF250 and BG505 glycan knocked-in viral variants revealed that the BG505 Env backbone specific nAb responses targeted a glycan hole formed by the absence of a glycan at N289 for this strain, as has also been previously observed by others studies as an immunodominant site on BG505 Env (Klasse et al., 2018; McCoy et al., 2016). The CRF250 Env backbone-specific nAb responses did not map to two of the predicted glycan holes at N234 and N276 positions. The lack of backbone Env responses in sequential immunization suggests a possible advantage for this strategy relative to cocktail immunization.

Figure 4:
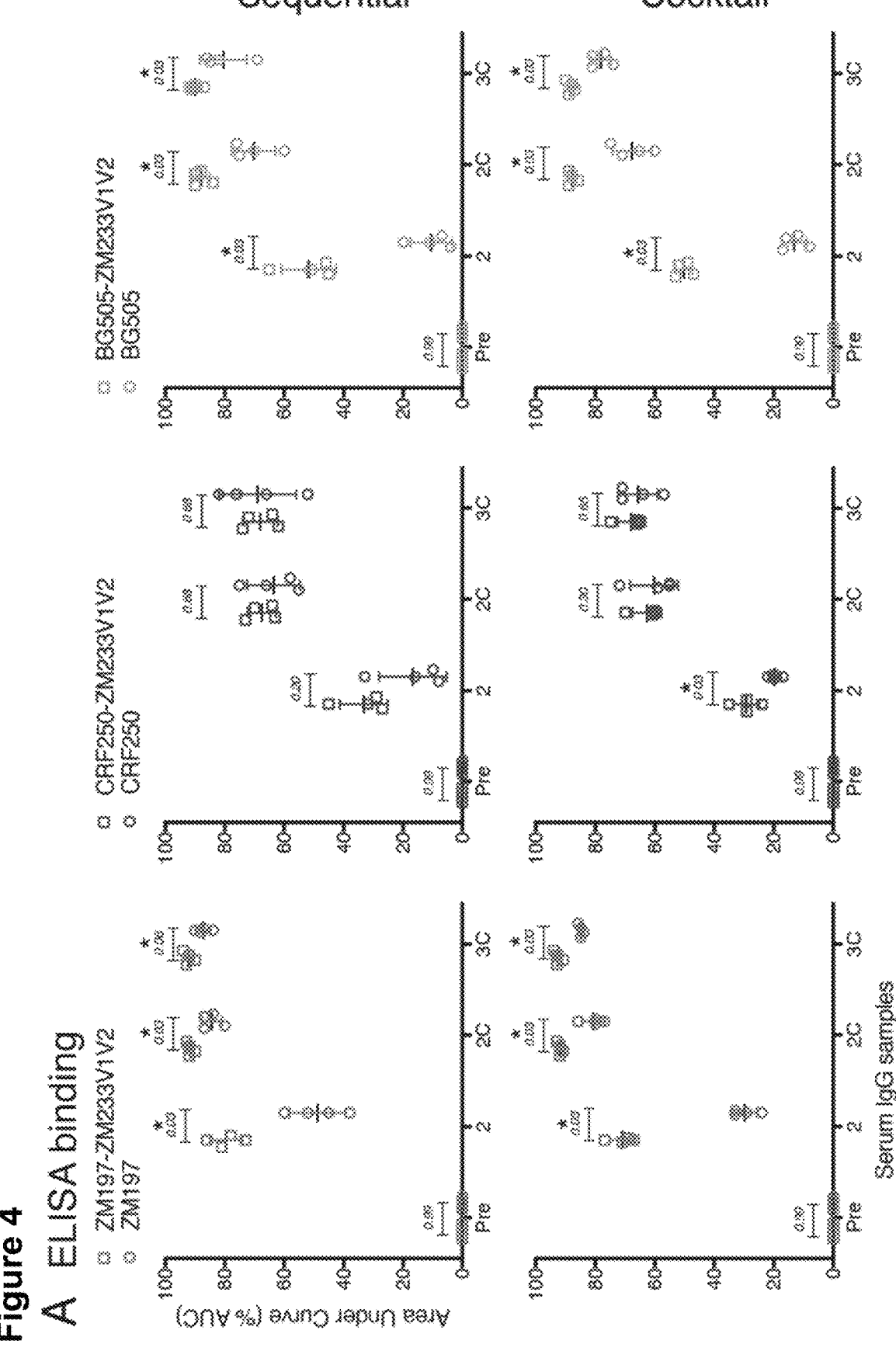
FIG. 4. ELISA binding activities of sequential and cocktail group serum IgG responses against chimeric ZM233V1V2 and the WT Env-backbone trimers. A. Dot plots showing binding activities of the sequential and cocktail immunization elicited serum IgG responses against the chimeric ZM233V1V2 trimers and their corresponding WT Env-trimer backbones. Binding activities of the serum IgG responses at four select time points; pre-bleed (Pre), 2-months post-prime (2), and respectively 14-days post boost-1 (2C) and boost-2 (3C) were derived from IgG binding titrations and expressed as percent area under curve (% AUC). Each dot represents binding response (% AUC) of serum IgG response time points with the respective trimer protein. The binding responses for each serum IgG sample with chimeric ZM233V1V2 trimer and WT Env-backbone trimers were compared in both sequential and cocktail strategies by Mann-Whitney test and the p-value for each time point is indicated. p-values less than 0.05 are treated as significant and indicated by asterisk. B. ELISA binding titrations of representative sequential (I1) and cocktail (J1) group rabbit serum IgG samples with chimeric ZM233V1V2 and the corresponding WT Env-backbone soluble trimers.
Figure 4:
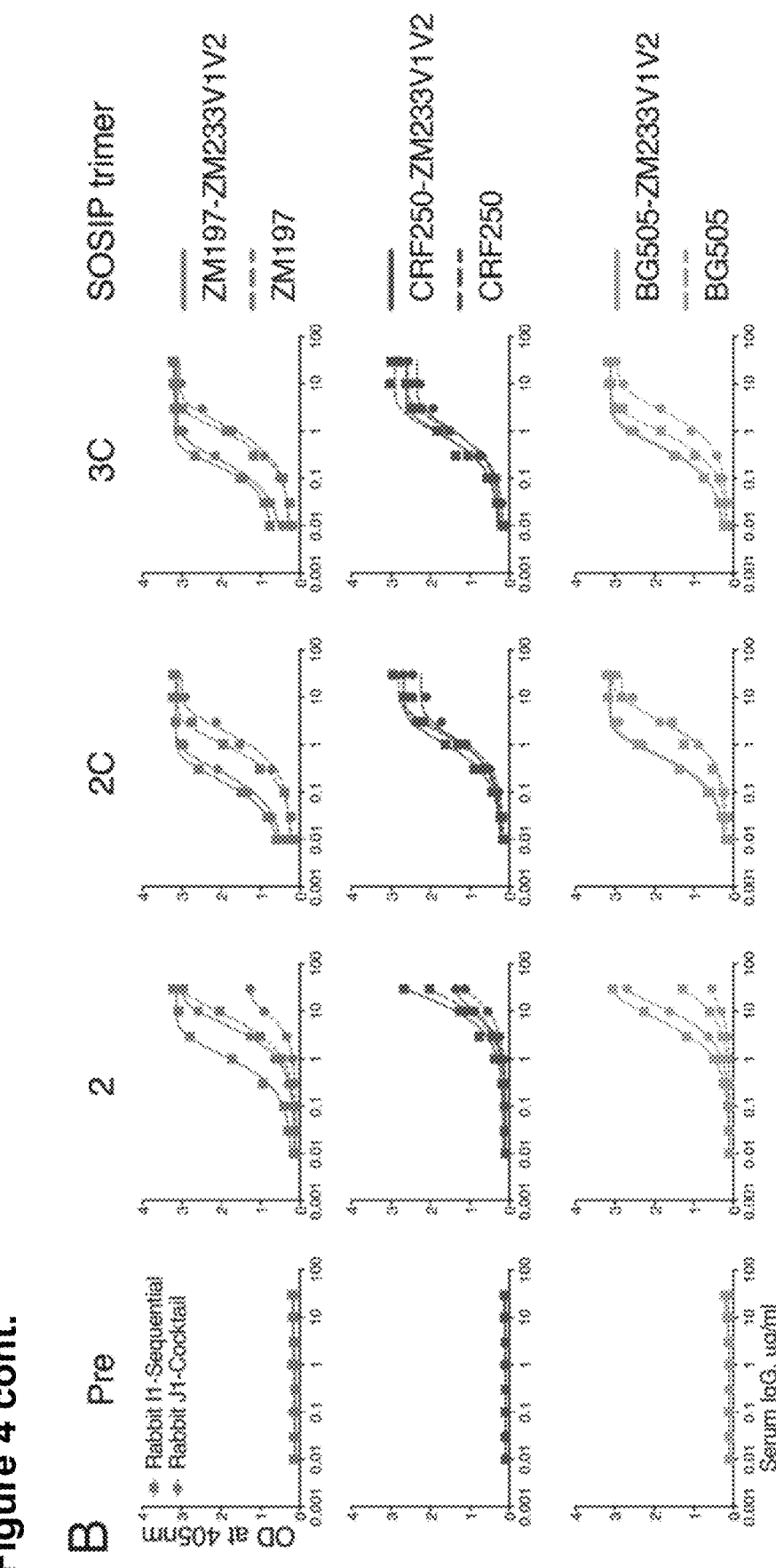
Figure 5:
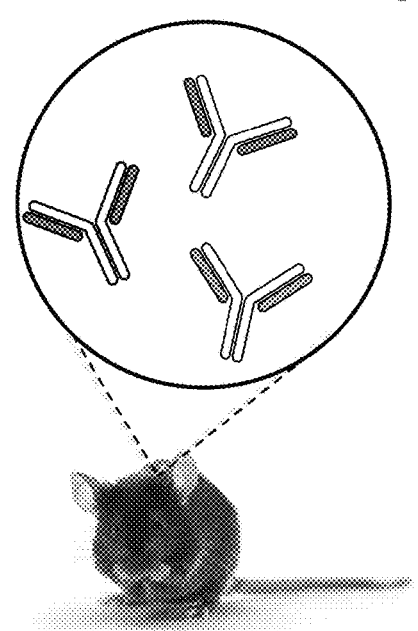
FIG. 5. V2-immunofocusing: Immunizations with ZM233V1V2 chimeric trimers in CH01 UCA HC-only knock-in mice elicit nAb responses with moderate breadth for heterologous HIV isolates. Left: CH01 UCA HC-only knock in mouse model design Top right: Immunization schedule of CH01 UCA HC-only KI mice immunized with ZM233V1V2 chimeric trimers and HIV Env derived trimers. Bottom right: Plot showing $IC_{50}$ Neutralization titers of the Bleed #3 plasma samples (post $2^{nd}$ boost immunization with 4-trimer cocktail) from 5 CH01 UCA HC-only mice, against the priming immunogen-matched autologous virus, ZM233, booster immunogen-matched, CH01 sensitive, and global panel HIV Env-encoding viruses.
Figure 5:
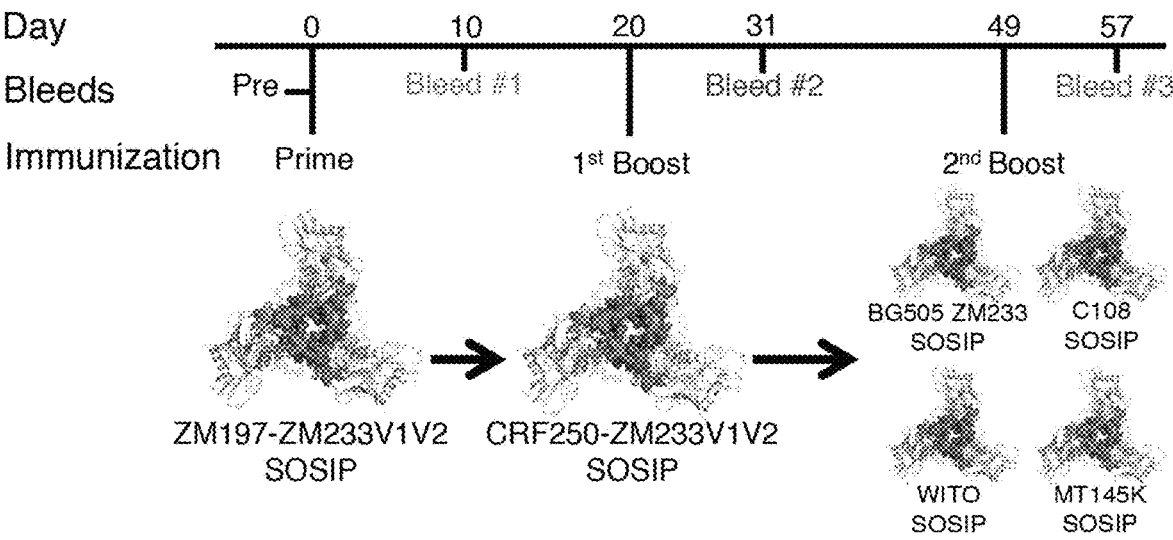

In another approach, to specificity, we evaluated the binding of immune serum IgGs to wild-type (WT) ZM197, CRF250, BG505 soluble trimers and their ZM233V1V2 chimeric variants by ELISA. Both immunization groups developed cross-reactive Ab responses against the chimeric ZM233V1V2 as well as the WT Env-backbone trimers. The ELISA Ab binding titers, represented as percent area under curve (% AUC), in both sequential and cocktail trimer immunized rabbits were significantly higher against the chimeric ZM233V1V2 trimers compared to their respective WT Env-backbone trimers (FIG. 4A), consistent with a strong V1V2 response. The Ab binding titers with chimeric V1V2 trimers were up to a 10-fold higher than their corresponding WT Env-backbone trimers and these differential Ab binding titers varied across the two immunization groups and were largely immunogen and immunization-stage dependent. While ZM233V1V2 on BG505 and ZM197 Env backbones showed the highest differences in the Ab binding titers between the chimeric ZM233V1V2 versus WT backbone trimers, the differences were lower for CRF250 and its V1V2 chimeric trimer suggesting that CRF250 among these three trimers particularly developed the highest Ab responses to the Env-backbone. Overall, the ratios of Ab binding titers with chimeric V1V2 to WT-trimer were highest at the immunization prime, which then gradually dropped as the immunizations progressed but were still substantially higher in both immunization groups even after post boost-2 immunization.

Altogether, among the two immunization strategies, only the cocktail group animals developed nAb responses that targeted WT trimer Env-backbones, including the glycan holes. However, both immunization strategies induced cross-reactive Abs and the responses were heavily dominated by V1V2-specificities at priming and were further maintained at considerable levels at boosting immunizations generation.

Example 5. Dynamics of Sequential Versus Cocktail Immunization-Elicited Ab Responses and Implications for Ab Immunofocusing To study the quality of Ab responses elicited by sequential and cocktail immunizations, and how these changed at primary and secondary immunization stages, we used Bio-Layer Interferometry (BLI). Responses were analyzed with ZM197-ZM233V1V2 chimeric trimer, as it was the priming immunogen in the sequential immunization group. As for ELISA and neutralization studies above, the BLI binding kinetics revealed an overall increase in the apparent binding affinities of serum IgG responses in both groups over the course of immunizations. The primary immune responses began with apparent KD values of high nM to μM affinity range but reached to low nM KD affinities (higher affinity binding) at post boost-2 secondary immunizations. The studies revealed a trend towards higher apparent affinity for sequential as compared to cocktail immunization (FIG. 6A); this trend was mirrored in neutralizing titers (FIG. 6B).

Notably, there was a strong correlation between BLI binding KDs with the ZM197-ZM233V1V2 SOSIP trimer and ZM233 virus IC50 neutralizing titers for both sequential (r=0.85, p=0.009) and cocktail (r=0.9, p=0.002) immunization groups indicating that the BLI binding of IgGs with the trimer largely captured the magnitude of V1V2-specific nAb responses. The result also highlight that the BLI binding of serum IgG responses likely reflects reasonably accurately the dynamics of B cell affinity maturation.

We used a BLI competition approach to compare the abilities of elicited serum IgG responses from sequential and cocktail approaches to compete with the known V2-apex bnAbs, PGT145 and CAP256.09. We focused on representative serum IgG samples that after primary and secondary immunizations. Both approaches generated serum Ab responses that showed competition with the V2-apex bnAbs following multiple immunizations. The most striking difference between the two approaches was the lack of competition by the cocktail group primary immune response except for one IgG sample that displayed competition with PGT145 bnAb. The results suggest that there was less epitope focusing in the cocktail group at priming compared to the sequential strategy but the responses became comparable after multiple immunizations.

Example 6. Discussion

Consensus has built around the need for a multi-immunogen sequential immunization strategy to induce bnAbs. A number of problems are to be faced in this strategy including activating rare naïve B cell precursors, shepherding the response along favorable pathways and generating sufficient Ab breadth and potency in the final response to offer robust protection. In the case of V2-apex bnAbs, naïve B cell precursors have long to very long CDRH3s and are rare in the human repertoire. One approach to initiating a response to the V2-apex is to induce Abs to the general apex region, by immunizing with Env trimers bearing a glycan hole at the apex. This approach was shown to induce nAbs to the apex, including the lysine-rich strand C of V2 recognized by V2-apex bnAbs, when rabbits were repeat immunized with some Env trimers but not others (Voss et al., 2017). However, sequential or cocktail immunization with differing Env trimers to attempt to broaden responses led to no induction of nAbs at all. Reasoning this may be due to affinity differences between the V2 apex epitope on different trimers, we investigated a chimeric Env immunogen approach using a common V1V2 region transplanted on to different backbones.

We showed first that one particular V1V2 from isolate ZM233 could be successfully transplanted onto different Env backbones with maintenance of native trimer structure and antigenicity. We then used a series of chimeric Env constructs bearing the ZM233 V1V2 as immunogens in rabbits in sequential and cocktail modalities. In contrast to previous studies, including our own (Voss et al., 2017) and those with subtype A, B and C Env derived trimer immunogens (Klasse et al., 2018; Torrents de la Pena et al., 2018) that produced sporadic nAb responses, the chimeric V1V2 trimers induced nAb responses that were not only highly reproducible but also consistently focused on the V2-apex region. Specificity was indicated by the adverse effects of V2 substitutions on immune serum IgG neutralization and by competition of V2-apex bnAbs and immune serum for binding to Env trimers. The nAb responses after 3 immunizations were comparable in sequential and cocktail immunization strategies, although there was a trend for the nAb response to appear earlier in the sequential schedule as compared to the cocktail schedule. The off-target responses were also somewhat greater in the cocktail responses suggesting a potential advantage for the sequential strategy.

The most remarkable feature of these immunization strategies was a successful recall of the nAb responses that was highly durable. Thus, design strategy of homogenizing a bnAb epitope region on prime/boost sequential immunogens might be applicable to other HIV Env bnAb epitopes or presumably for variable pathogen bnAb epitopes with intrinsic conformational heterogeneity, especially at steps involving effective Ab recall response In the studies, we failed to produce cross-neutralizing responses despite the fact that the nAb responses targeted strand C core epitope residues that conserve a positive charge character across different virus isolates and are targeted by human V2-apex bnAbs (Andrabi et al., 2015; Gorman et al., 2016; Lee et al., 2017; Sok et al., 2014). In part, this may be due to a different character of the rabbit nAbs as compared to human bnAbs, Assuming favorable bnAb precursors can be selected in humans, further boosting will likely be required to improve neutralization breadth. Two strategies can be envisaged. One attempts to focus developing nAb lineages on the most conserved elements within the V2-apex epitope region. The second seeks to train B cells to recognize the more diverse features within the V1V2 loop, including loop sequence, length, and glycan heterogeneity. Virus-antibody co-evolutionary studies from natural infection support the approach that involves amino acid diversification at certain critical positions rather than changing the entire variable loop sequence region (Bhiman et al., 2015; Doria-Rose et al., 2014; Landais et al., 2017). Hence, a developing bnAb lineage may initially require to mature in response to subtle changes within the bnAb epitope to stay on the right trajectory during the affinity maturation pathways, but sufficient to broaden the Ab response against diverse viruses. Nevertheless, it remains to be seen how polyclonal immune systems with higher frequency of appropriate long CDRH3 B cells will behave to these immunofocusing immunization strategies.

Overall, we developed here immunogens and strategies that can reproducibly induce an immunofocused nAb response to a vulnerable site on HIV Env and potentially similar design strategies could be adapted to other critical targets on variable pathogen surfaces. These design strategies drove antibody responses deterministically, thus, investigating these immunogens in diverse B cell repertoire systems at primary and secondary immune stages using various immunization schemes could provide important clues about how complex antigens drive B cell selection and better our understanding to design more robust vaccines. These immunization design strategies will not only inform on how complex antigen driven B cell lineage structures vary as a function of change in the immunogen surface but also how distribution of the antibody genetic features change at primary and secondary immune responses. Our study overall illustrates how rational design of immunogens and strategies can favorably influence the outcome of B cell responses and the results obtained here will help guide design and strategies of HIV vaccines that can induce protective antibodies in humans.

REFERENCES

Abbott, R. K., Lee, J. H., Menis, S., Skog, P., Rossi, M., Ota, T., Kulp, D. W., Bhullar, D., Kalyuzhniy, O., Havenar-Daughton, C., et al. (2018). Precursor Frequency and Affinity Determine B Cell Competitive Fitness in Germinal Centers, Tested with Germline-Targeting HIV Vaccine Immunogens. Immunity 48, 133-146 e136.

Andrabi, R., Bhiman, J. N., and Burton, D. R. (2018). Strategies for a multi-stage neutralizing antibody-based HIV vaccine. Curr Opin Immunol 53, 143-151.

Andrabi, R., Su, C. Y., Liang, C. H., Shivatare, S. S., Briney, B., Voss, J. E., Nawazi, S. K., Wu, C. Y., Wong, C. H., and Burton, D. R. (2017). Glycans Function as Anchors for Antibodies and Help Drive HIV Broadly Neutralizing Antibody Development. Immunity 47, 524-537 e523.

Andrabi, R., Voss, J. E., Liang, C. H., Briney, B., McCoy, L. E., Wu, C. Y., Wong, C. H., Poignard, P., and Burton, D. R. (2015). Identification of Common Features in Prototype Broadly Neutralizing Antibodies to HIV Envelope V2 Apex to Facilitate Vaccine Design. Immunity 43, 959-973.

Batista, F. D., and Neuberger, M. S. (1998). Affinity dependence of the B cell response to antigen: a threshold, a ceiling, and the importance of off-rate. Immunity 8, 751-759.

Behrens, A. J., Vasiljevic, S., Pritchard, L. K., Harvey, D. J., Andev, R. S., Krumm, S. A., Struwe, W. B., Cupo, A., Kumar, A., Zitzmann, N., et al. (2016). Composition and Antigenic Effects of Individual Glycan Sites of a Trimeric HIV-1 Envelope Glycoprotein. Cell reports 14, 2695-2706.

Bhiman, J. N., Anthony, C., Doria-Rose, N. A., Karimanzira, O., Schramm, C. A., Khoza, T., Kitchin, D., Botha, G., Gorman, J., Garrett, N.J., et al. (2015). Viral variants that initiate and drive maturation of V1V2-directed HIV-1 broadly neutralizing antibodies. Nature medicine 21, 1332-1336.

Bonomelli, C., Doores, K. J., Dunlop, D. C., Thaney, V., Dwek, R. A., Burton, D. R., Crispin, M., and Scanlan, C. N. (2011). The glycan shield of HIV is predominantly oligomannose independently of production system or viral clade. PloS one 6, e23521.

Bonsignori, M., Hwang, K. K., Chen, X., Tsao, C. Y., Morris, L., Gray, E., Marshall, D. J., Crump, J. A., Kapiga, S. H., Sam, N. E., et al. (2011). Analysis of a clonal lineage of HIV-1 envelope V2/V3 conformational epitope-specific broadly neutralizing antibodies and their inferred unmutated common ancestors. Journal of virology 85, 9998-10009.

Bonsignori, M., Zhou, T., Sheng, Z., Chen, L., Gao, F., Joyce, M. G., Ozorowski, G., Chuang, G. Y., Schramm, C. A., Wiehe, K., et al. (2016). Maturation Pathway from Germline to Broad HIV-1 Neutralizer of a CD4-Mimic Antibody. Cell 165, 449-463.

Briney, B., Sok, D., Jardine, J. G., Kulp, D. W., Skog, P., Menis, S., Jacak, R., Kalyuzhniy, O., de Val, N., Sesterhenn, F., et al. (2016). Tailored Immunogens Direct Affinity Maturation toward HIV Neutralizing Antibodies. Cell 166, 1459-1470 e1411.

Briney, B. S., Willis, J. R., and Crowe, J. E., Jr. (2012). Human peripheral blood antibodies with long HCDR3s are established primarily at original recombination using a limited subset of germline genes. PloS one 7, e36750.

Burton, D. R. (2017). What Are the Most Powerful Immunogen Design Vaccine Strategies?Reverse Vaccinology 2.0 Shows Great Promise. Cold Spring Harb Perspect Biol.

Burton, D. R., and Hangartner, L. (2016). Broadly Neutralizing Antibodies to HIV and Their Role in Vaccine Design. Annual review of immunology 34, 635-659.

Cao, L., Diedrich, J. K., Kulp, D. W., Pauthner, M., He, L., Park, S. R., Sok, D., Su, C. Y., Delahunty, C. M., Menis, S., et al. (2017). Global site-specific N-glycosylation analysis of HIV envelope glycoprotein. Nature communications 8, 14954.

Crispin, M., Ward, A. B., and Wilson, I. A. (2018). Structure and Immune Recognition of the HIV Glycan Shield. Annu Rev Biophys.

de Taeye, S. W., Ozorowski, G., Torrents de la Pena, A., Guttman, M., Julien, J. P., van den Kerkhof, T. L., Burger, J. A., Pritchard, L. K., Pugach, P., Yasmeen, A., et al. (2015). Immunogenicity of Stabilized HIV-1 Envelope Trimers with Reduced Exposure of Non-neutralizing Epitopes. Cell 163, 1702-1715.

deCamp, A., Hraber, P., Bailer, R. T., Seaman, M. S., Ochsenbauer, C., Kappes, J., Gottardo, R., Edlefsen, P., Self, S., Tang, H., et al. (2014). Global panel of HIV-1 Env reference strains for standardized assessments of vaccine-elicited neutralizing antibodies. Journal of virology 88, 2489-2507.

Doria-Rose, N. A., Schramm, C. A., Gorman, J., Moore, P. L., Bhiman, J. N., DeKosky, B. J., Ernandes, M. J., Georgiev, I. S., Kim, H. J., Pancera, M., et al. (2014). Developmental pathway for potent V1V2-directed HIV-neutralizing antibodies. Nature 509, 55-62.

Dosenovic, P., Kara, E. E., Pettersson, A. K., McGuire, A. T., Gray, M., Hartweger, H., Thientosapol, E. S., Stamatatos, L., and Nussenzweig, M. C. (2018). Anti-HIV-1 B cell responses are dependent on B cell precursor frequency and antigen-binding affinity. Proceedings of the National Academy of Sciences of the United States of America 115, 4743-4748.

Dosenovic, P., von Boehmer, L., Escolano, A., Jardine, J., Freund, N. T., Gitlin, A. D., McGuire, A. T., Kulp, D. W., Oliveira, T., Scharf, L., et al. (2015). Immunization for HIV-1 Broadly Neutralizing Antibodies in Human Ig Knockin Mice. Cell 161, 1505-1515.

Escolano, A., Dosenovic, P., and Nussenzweig, M. C. (2017). Progress toward active or passive HIV-1 vaccination. The Journal of experimental medicine 214, 3-16.

Escolano, A., Steichen, J. M., Dosenovic, P., Kulp, D. W., Golijanin, J., Sok, D., Freund, N. T., Gitlin, A. D., Oliveira, T., Araki, T., et al. (2016). Sequential Immunization Elicits Broadly Neutralizing Anti-HIV-1 Antibodies in Ig Knockin Mice. Cell 166, 1445-1458 e1412.

Georgiev, I. S., Doria-Rose, N. A., Zhou, T., Kwon, Y. D., Staupe, R. P., Moquin, S., Chuang, G. Y., Louder, M. K., Schmidt, S. D., Altae-Tran, H. R., et al. (2013). Delineating antibody recognition in polyclonal sera from patterns of HIV-1 isolate neutralization. Science 340, 751-756.

Gorman, J., Soto, C., Yang, M. M., Davenport, T. M., Guttman, M., Bailer, R. T., Chambers, M., Chuang, G. Y., DeKosky, B. J., Doria-Rose, N. A., et al. (2016). Structures of HIV-1 Env V1V2 with broadly neutralizing antibodies reveal commonalities that enable vaccine design. Nature structural & molecular biology 23, 81-90.

Havenar-Daughton, C., Lee, J. H., and Crotty, S. (2017). Tfh cells and HIV bnAbs, an immunodominance model of the HIV neutralizing antibody generation problem. Immunological reviews 275, 49-61.

Haynes, B. F., and Mascola, J. R. (2017). The quest for an antibody-based HIV vaccine. Immunol Rev 275, 5-10.

Hu, J. K., Crampton, J. C., Cupo, A., Ketas, T., van Gils, M. J., Sliepen, K., de Taeye, S. W., Sok, D., Ozorowski, G., Deresa, I., et al. (2015). Murine Antibody Responses to Cleaved Soluble HIV-1 Envelope Trimers Are Highly Restricted in Specificity. Journal of virology 89, 10383-10398.

Jardine, J. G., Ota, T., Sok, D., Pauthner, M., Kulp, D. W., Kalyuzhniy, O., Skog, P. D., Thinnes, T. C., Bhullar, D., Briney, B., et al. (2015). HIV-1 VACCINES. Priming a broadly neutralizing antibody response to HIV-1 using a germline-targeting immunogen. Science 349, 156-161.

Julien, J. P., Lee, J. H., Ozorowski, G., Hua, Y., Torrents de la Pena, A., de Taeye, S. W., Nieusma, T., Cupo, A., Yasmeen, A., Golabek, M., et al. (2015). Design and structure of two HIV-1 clade C SOSIP.664 trimers that increase the arsenal of native-like Env immunogens. Proceedings of the National Academy of Sciences of the United States of America 112, 11947-11952.

Kelsoe, G., and Haynes, B. F. (2017). What Are the Primary Limitations in B-Cell Affinity Maturation, and How Much Affinity Maturation Can We Drive with Vaccination-?Breaking through Immunity's Glass Ceiling. Cold Spring Harb Perspect Biol.

Kepler, T. B., Liao, H. X., Alam, S. M., Bhaskarabhatla, R., Zhang, R., Yandava, C., Stewart, S., Anasti, K., Kelsoe, G., Parks, R., et al. (2014). Immunoglobulin gene insertions and deletions in the affinity maturation of HIV-1 broadly reactive neutralizing antibodies. Cell host & microbe 16, 304-313.

Kepler, T. B., and Wiehe, K. (2017). Genetic and structural analyses of affinity maturation in the humoral response to HIV-1. Immunological reviews 275, 129-144.

Klasse, P. J., Ketas, T. J., Cottrell, C. A., Ozorowski, G., Debnath, G., Camara, D., Francomano, E., Pugach, P., Ringe, R. P., LaBranche, C. C., et al. (2018). Epitopes for neutralizing antibodies induced by HIV-1 envelope glycoprotein BG505 SOSIP trimers in rabbits and macaques. PLoS pathogens 14, e1006913.

Klasse, P. J., LaBranche, C. C., Ketas, T. J., Ozorowski, G., Cupo, A., Pugach, P., Ringe, R. P., Golabek, M., van Gils, M. J., Guttman, M., et al. (2016). Sequential and Simultaneous Immunization of Rabbits with HIV-1 Envelope Glycoprotein SOSIP.664 Trimers from Clades A, B and C. PLoS pathogens 12, e1005864.

Klein, F., Diskin, R., Scheid, J. F., Gaebler, C., Mouquet, H., Georgiev, I. S., Pancera, M., Zhou, T., Incesu, R. B., Fu, B. Z., et al. (2013). Somatic mutations of the immunoglobulin framework are generally required for broad and potent HIV-1 neutralization. Cell 153, 126-138.

Kulp, D. W., Steichen, J. M., Pauthner, M., Hu, X., Schiffner, T., Liguori, A., Cottrell, C. A., Havenar-Daughton, C., Ozorowski, G., Georgeson, E., et al. (2017). Structure-based design of native-like HIV-1 envelope trimers to silence non-neutralizing epitopes and eliminate CD4 binding. Nature communications 8, 1655.

Kwong, P. D., and Mascola, J. R. (2018). HIV-1 Vaccines Based on Antibody Identification, B Cell Ontogeny, and Epitope Structure. Immunity 48, 855-871.

Landais, E., Huang, X., Havenar-Daughton, C., Murrell, B., Price, M. A., Wickramasinghe, L., Ramos, A., Bian, C. B., Simek, M., Allen, S., et al. (2016). Broadly Neutralizing Antibody Responses in a Large Longitudinal Sub-Saharan HIV Primary Infection Cohort. PLoS pathogens 12, e1005369.

Landais, E., Murrell, B., Briney, B., Murrell, S., Rantalainen, K., Berndsen, Z. T., Ramos, A., Wickramasinghe, L., Smith, M. L., Eren, K., et al. (2017). HIV Envelope Glycoform Heterogeneity and Localized Diversity Govern the Initiation and Maturation of a V2 Apex Broadly Neutralizing Antibody Lineage. Immunity 47, 990-1003 e1009.

Lavinder, J. J., Hoi, K. H., Reddy, S. T., Wine, Y., and Georgiou, G. (2014). Systematic characterization and comparative analysis of the rabbit immunoglobulin repertoire. PLoS one 9, e101322.

Lee, J. H., Andrabi, R., Su, C. Y., Yasmeen, A., Julien, J. P., Kong, L., Wu, N.C., McBride, R., Sok, D., Pauthner, M., et al. (2017). A Broadly Neutralizing Antibody Targets the Dynamic HIV Envelope Trimer Apex via a Long, Rigidified, and Anionic beta-Hairpin Structure. Immunity 46, 690-702.

Li, G. M., Chiu, C., Wrammert, J., McCausland, M., Andrews, S. F., Zheng, N.Y., Lee, J. H., Huang, M., Qu, X., Edupuganti, S., et al. (2012). Pandemic H1N1 influenza vaccine induces a recall response in humans that favors broadly cross-reactive memory B cells. Proceedings of the National Academy of Sciences of the United States of America 109, 9047-9052.

Liao, H. X., Lynch, R., Zhou, T., Gao, F., Alam, S. M., Boyd, S. D., Fire, A. Z., Roskin, K. M., Schramm, C. A., Zhang, Z., et al. (2013). Co-evolution of a broadly neutralizing HIV-1 antibody and founder virus. Nature 496, 469-476.

MacLeod, D. T., Choi, N. M., Briney, B., Garces, F., Ver, L. S., Landais, E., Murrell, B., Wrin, T., Kilembe, W., Liang, C. H., et al. (2016). Early Antibody Lineage Diversification and Independent Limb Maturation Lead to Broad HIV-1 Neutralization Targeting the Env High-Mannose Patch. Immunity 44, 1215-1226.

Mascola, J. R., and Haynes, B. F. (2013). HIV-1 neutralizing antibodies: understanding nature's pathways. Immunological reviews 254, 225-244.

McCoy, L. E., and Burton, D. R. (2017). Identification and specificity of broadly neutralizing antibodies against HIV. Immunological reviews 275, 11-20.

McCoy, L. E., van Gils, M. J., Ozorowski, G., Messmer, T., Briney, B., Voss, J. E., Kulp, D. W., Macauley, M. S., Sok, D., Pauthner, M., et al. (2016). Holes in the Glycan Shield of the Native HIV Envelope Are a Target of Trimer-Elicited Neutralizing Antibodies. Cell reports 16, 2327-2338.

McGuire, A. T., Hoot, S., Dreyer, A. M., Lippy, A., Stuart, A., Cohen, K. W., Jardine, J., Menis, S., Scheid, J. F., West, A. P., et al. (2013). Engineering HIV envelope protein to activate germline B cell receptors of broadly neutralizing anti-CD4 binding site antibodies. The Journal of experimental medicine 210, 655-663.

McLellan, J. S., Pancera, M., Carrico, C., Gorman, J., Julien, J. P., Khayat, R., Louder, R., Pejchal, R., Sastry, M., Dai, K., et al. (2011). Structure of HIV-1 gp120 V1/V2 domain with broadly neutralizing antibody PG9. Nature 480, 336-343.

Pancera, M., McLellan, J. S., Wu, X., Zhu, J., Changela, A., Schmidt, S. D., Yang, Y., Zhou, T., Phogat, S., Mascola, J. R., et al. (2010). Crystal structure of PG16 and chimeric dissection with somatically related PG9: structure-function analysis of two quaternary-specific antibodies that effectively neutralize HIV-1. Journal of virology 84, 8098-8110.

Pancera, M., Shahzad-Ul-Hussan, S., Doria-Rose, N. A., McLellan, J. S., Bailer, R. T., Dai, K., Loesgen, S., Louder, M. K., Staupe, R. P., Yang, Y., et al. (2013). Structural basis for diverse N-glycan recognition by HIV-1-neutralizing V1-V2-directed antibody PG16. Nature structural & molecular biology 20, 804-813.

Pauthner, M., Havenar-Daughton, C., Sok, D., Nkolola, J. P., Bastidas, R., Boopathy, A. V., Carnathan, D. G., Chandrashekar, A., Cirelli, K. M., Cottrell, C. A., et al. (2017). Elicitation of Robust Tier 2 Neutralizing Antibody Responses in Nonhuman Primates by HIV Envelope Trimer Immunization Using Optimized Approaches. Immunity 46, 1073-1088 e1076.

Pritchard, L. K., Vasiljevic, S., Ozorowski, G., Seabright, G. E., Cupo, A., Ringe, R., Kim, H. J., Sanders, R. W., Doores, K. J., Burton, D. R., et al. (2015). Structural Constraints Determine the Glycosylation of HIV-1 Envelope Trimers. Cell reports 11, 1604-1613.

Pugach, P., Ozorowski, G., Cupo, A., Ringe, R., Yasmeen, A., de Val, N., Derking, R., Kim, H. J., Korzun, J., Golabek, M., et al. (2015). A native-like SOSIP.664 trimer based on a HIV-1 subtype B env gene. Journal of virology.

Sanders, R. W., Derking, R., Cupo, A., Julien, J. P., Yasmeen, A., de Val, N., Kim, H. J., Blattner, C., de la Pena, A. T., Korzun, J., et al. (2013). A next-generation cleaved, soluble HIV-1 Env trimer, BG505 SOSIP.664 gp140, expresses multiple epitopes for broadly neutralizing but not non-neutralizing antibodies. PLoS Pathog 9, e1003618.

Sanders, R. W., and Moore, J. P. (2017). Native-like Env trimers as a platform for HIV-1 vaccine design. Immunological reviews 275, 161-182.

Sanders, R. W., van Gils, M. J., Derking, R., Sok, D., Ketas, T. J., Burger, J. A., Ozorowski, G., Cupo, A., Simonich, C., Goo, L., et al. (2015). HIV-1 VACCINES. HIV-1 neutralizing antibodies induced by native-like envelope trimers. Science 349, aac4223.

Silva, M., Nguyen, T. H., Philbrook, P., Chu, M., Sears, O., Hatfield, S., Abbott, R. K., Kelsoe, G., and Sitkovsky, M. V. (2017). Targeted Elimination of Immunodominant B Cells Drives the Germinal Center Reaction toward Subdominant Epitopes. Cell reports 21, 3672-3680.

Sok, D., Moldt, B., and Burton, D. R. (2013). SnapShot: broadly neutralizing antibodies. Cell 155, 728-728 e721.

Sok, D., van Gils, M. J., Pauthner, M., Julien, J. P., Saye-Francisco, K. L., Hsueh, J., Briney, B., Lee, J. H., Le, K. M., Lee, P. S., et al. (2014). Recombinant HIV envelope trimer selects for quaternary-dependent antibodies targeting the trimer apex. Proceedings of the National Academy of Sciences of the United States of America 111, 17624-17629.

Stamatatos, L., Pancera, M., and McGuire, A. T. (2017). Germline-targeting immunogens. Immunological reviews 275, 203-216.

Steichen, J. M., Kulp, D. W., Tokatlian, T., Escolano, A., Dosenovic, P., Stanfield, R. L., McCoy, L. E., Ozorowski, G., Hu, X., Kalyuzhniy, O., et al. (2016). HIV Vaccine Design to Target Germline Precursors of Glycan-Dependent Broadly Neutralizing Antibodies. Immunity 45, 483-496.

Tian, M., Cheng, C., Chen, X., Duan, H., Cheng, H. L., Dao, M., Sheng, Z., Kimble, M., Wang, L., Lin, S., et al. (2016). Induction of HIV Neutralizing Antibody Lineages in Mice with Diverse Precursor Repertoires. Cell 166, 1471-1484 e1418.

Torrents de la Pena, A., de Taeye, S. W., Sliepen, K., LaBranche, C. C., Burger, J. A., Schermer, E. E., Montefiori, D. C., Moore, J. P., Klasse, P. J., and Sanders, R. W. (2018). Immunogenicity in Rabbits of HIV-1 SOSIP Trimers from Clades A, B, and C, Given Individually, Sequentially, or in Combination. Journal of virology 92.

Torrents de la Pena, A., Julien, J. P., de Taeye, S. W., Garces, F., Guttman, M., Ozorowski, G., Pritchard, L. K., Behrens, A. J., Go, E. P., Burger, J. A., et al. (2017). Improving the Immunogenicity of Native-like HIV-1 Envelope Trimers by Hyperstabilization. Cell reports 20, 1805-1817.

Victora, G. D., and Mouquet, H. (2017). What Are the Primary Limitations in B-Cell Affinity Maturation, and How Much Affinity Maturation Can We Drive with Vaccination? Lessons from the Antibody Response to HIV-1. Cold Spring Harb Perspect Biol.

Victora, G. D., and Wilson, P. C. (2015). Germinal center selection and the antibody response to influenza. Cell 163, 545-548.

Voss, J. E., Andrabi, R., McCoy, L. E., de Val, N., Fuller, R. P., Messmer, T., Su, C. Y., Sok, D., Khan, S. N., Garces, F., et al. (2017). Elicitation of Neutralizing Antibodies Targeting the V2 Apex of the HIV Envelope Trimer in a Wild-Type Animal Model. Cell reports 21, 222-235.

Walker, L. M., Simek, M. D., Priddy, F., Gach, J. S., Wagner, D., Zwick, M. B., Phogat, S. K., Poignard, P., and Burton, D. R. (2010). A limited number of antibody specificities mediate broad and potent serum neutralization in selected HIV-1 infected individuals. PLoS pathogens 6, e1001028.

Wang, S., Mata-Fink, J., Kriegsman, B., Hanson, M., Irvine, D. J., Eisen, H. N., Burton, D. R., Wittrup, K. D., Kardar, M., and Chakraborty, A. K. (2015). Manipulating the Selection Forces during Affinity Maturation to Generate Cross-Reactive HIV Antibodies. Cell 160, 785-797.

West, A. P., Jr., Diskin, R., Nussenzweig, M. C., and Bjorkman, P. J. (2012). Structural basis for germ-line gene usage of a potent class of antibodies targeting the CD4- binding site of HIV-1 gp120. Proceedings of the National Academy of Sciences of the United States of America 109, E2083-2090.

Williams, W. B., Zhang, J., Jiang, C., Nicely, N. I., Fera, D., Luo, K., Moody, M. A., Liao, H. X., Alam, S. M., Kepler, T. B., et al. (2017). Initiation of HIV neutralizing B cell lineages with sequential envelope immunizations. Nature communications 8, 1732.

```
SEQUENCES
HXB2 Env
                                SEQ ID NO: 1
MRVKEKYQHLWRWGWRWGTMLLGMLMICSATEKLWVTVYYGVPVW

KEATTTLFCASDAKAYDTEVHNVWATHACVPTDPNPQEVVLVNVT

ENFNMWKNDMVEQMHEDIISLWDQSLKPCVKLTPLCVSLKCTDLK

NDTNTNSSSGRMIMEKGEIKNCSFNISTSIRGKVQKEYAFFYKLD

IIPIDNDTTSYKLTSCNTSVITQACPKVSFEPIPIHYCAPAGFAI

LKCNNKTFNGTGPCTNVSTVQCTHGIRPVVSTQLLINGSLAEEEV

VIRSVNFTDNAKTIIVQLNISVEINCTRPNNNTRKRIRIQRGPGR

AFVTIGKIGNMRQAHCNISRAKWNNTLKQIASKLREQFGNNKTII

FKQSSGGDPEIVTHSFNCGGEFFYCNSTQLENSTWENSTWSTEGS

NNTEGSDTITLPCRIKQIINMWQKVGKAMYAPPISGQIRCSSNIT

GLLLTRDGGNSNNESEIFRPGGGDMRDNWRSELYKYKVVKIEPLG

VAPTKAKRRVVQREKRAVGIGALFLGFLGAAGSTMGAASMILTVQ

ARQLLSGIVQQQNNLLRAIEAQQHLLQLTVWGIKQLQARILAVER

YLKDQQLLGIWGCSGKLICITAVPWNASWSNKSLEQIWNHTTWME

WDREINNYTSLIHSLIEESQNQQEKNEQELLELDKWASLWNWENI

INWLWYIKLFIMIVGGLVGLRIVFAVLSIVNRVRQGYSPLSFQTH

LPTPRGPDRPEGIEEEGGERDRDRSIRLVNGSLALIWDDLRSLCL

FSYHRLRDLLLIVTRIVELLGRRGWEALKYWWNLLQYWSQELKNS

AVSLLNATAIAVAEGTDRVIEVVQGACRAIRHIPRRIRQGLERIL

L;

BG505 Env
                                SEQ ID NO: 2
MRVMGIQRNCQHLFRWGTMILGMIIICSAAENLWVTVYYGVPVWK

DAETTLFCASDAKAYETEKHNVWATHACVPTDPNPQEIHLENVTE

EFNMWKNNMVEQMHTDIISLWDQSLKPCVKLTPLCVILQCINVIN

NITDDMRGELKNCSFNMTTELRDKKQKVYSLFYRLDVVQINENQG

NRSNNSNKEYRLINCNTSAITQACPKVSFEPIPIHYCAPAGFAIL

KCKDKKFNGTGPCPSVSTVQCTHGIKPVVSTQLLLNGSLAEEEVM

IRSENIINNAKNILVQFNTPVQINCTRPNNNTRKSIRIGPGQAFY

ATGDIIGDIRQAHCTVSKATWNETLGKVVKQLRKHFGNNTIIRFA

NSSGGDLEVTTHSFNCGGEFFYCNTSGLENSTWISNISVQGSNST

GSNDSITLPCRIKQIINMWQRIGQAMYAPPIQGVIRCVSNITGLI

LTRDGGSINSITETFRPGGGDMRDNWRSELYKYKVVKIEPLGVAP

TRAKRRVVGREKRAVGIGAVFLGFLGAAGSTMGAASMTLTVQARN

LLSGIVQQQSNLLRAIEAQQHLLKLTVWGIKQLQARVLAVERYLR
```

```
DQQLLGIWGCSGKLICITNVPWNSSWSNRNLSEIWDNMTWLQWDK

EISNYTQIIYGLLEESQNQQEKNEQDLLALDKWASLWNWFDISNW

LWYIKIFIMIVGGLIGLRIVFAVLSVIHRVRQGYSPLSFQTHTPN

PRGLDRPERIEEEDGEQDRGRSTRLVSGFLALAWDDLRSLCLFCY

HRLRDFILIAARIVELLGHSSLKGLRLGWEGLKYLWNLLAYWGRE

LKISAINLFDTIAIAVAEWTDRVIEIGQRLCRAFLHIPRRIRQGL

ERALL;

ZM197 Env
                                SEQ ID NO: 3
MRVMGILRNWQQWWIWGILGFWMLMICNMEQLWVTVYYGVPVWKE

AKATLFCASDAKAYEKEVHNVWATHACVPTDPNPQEIPLGNVTEN

FNMWKNDMADQMHEDIISLWDQSLKPCVKLIPLCVTLNCSDATSN

ITKNATNTNTTSTDNRNATSNDTEMKGEIKDCTFNITTEVRDRKT

KQRALFYKLDVVPLEEEKNSSSKNSSYKEYRLISCNISTITQACP

KVSFDPIPIHYCAPAGYAILKCNNKTFNGTGPCHNVSTVQCTHGI

KPVVSTQLLLNGSLAEEEIIIRSENLTDNTKTIIVHLNESVEIEC

VRPNNNTRKSVRIGPGQTFFATGEIIGDIRQAHCDLSKSNWTTTL

KRIEKKLKEHFNNATIKFESSAGGDLEITTHSFNCRGEFFYCNTS

GLFNSSLLNDIDGTSNSTSNATITLPCRIKQIINMWQEVGRAMYA

SPIAGIIICKSNIIGLLLIRDGGNKSAGIETFRPGGGNMKDNWRS

ELYKYKVVEIKPLGIAPTSAKRRVVEREKRAAGIGAVILGFLGAA

GSTMGAASVMLTVQARQLLSGIVQQQSNLLRAIEAQQHMLQLTVW

GIKQLQTRVLAIERYLKDQQLLGLWGCSGKLICTTAVPWNTSWSN

KSKDEIWDNMTWMQWDREIDNYTQVIYQLLEVSQNQQEKNENDLL

ALDKWNSLWSWFDITKWLWYIKIFIMIVGGLIGLRIIFAVLSVVN

RVRQGYSPLSFQTLIPNPRGPDRPGGIEEEGGEQDKNRSTRLVSG

FLALVWDDLRSLCLFSYHRLRDFILIAARAVELLGRSSLEGLQWG

WETLKYLRNLVQYWGLELKQSAINLLDTIA;

CRF250 Env
                                SEQ ID NO: 4
MRVMGIQRNYPPLWRWGTMIFWMMMLCSAEKLWVTVYYGVPVWRE

ADTTLFCASDAKGYDTEAHNVWATHACVPTDPRPQEMYLENVTEN

FNMWKNSMVEQMHTDIISLWDESLKPCVKLTPLCVILDCQAFNSS

SHINSSIAMQEMKNCSFNVTTELRDKKKKEYSFFYKTDIEQINKN

GRQYRLINCNTSAITQACPKVSFEPIPIHFCAPAGFAILKCNEKH

FNGKGPCKNVSTVQCTHGIKPVVSTQLLINGSLAEEEVVIRVENT

IDNAKTIIVQLAKPVKINCTRPNNNTRKSIRIGPGQTFYATGDII

GNIRKAYCNVSKREWNNTLQQVAAQLSKSFNNTKIVFEKHSGGDL

EVITHSFVCGGEFFYCNTSGLFNSTWHNSTWINSTTGSNGTESND

TITLQCEIKQFINMWQRVGRAMYAPPIPGVIRCESDITGLLLTRD

GPNSTQNETFRPGGGDMRDNWRSELYKYKVVQIEPLGVAPTHAKR

RVVEREKRAVGLGAVFFGFLGAAGSTMGAASITLTVQARQLLSGI
```

-continued

VQQQSNWLKAIEAQQHLLRLTVWGIKQLQARVLALERYLKDQQLL

GIWGCSGKLICTTTVPWNSSWSNKNYTDIWDNMTWLQWDREISNY

TDEIYRLIEQSQNQQEKNEQDLLALDKWASLWNWFDITNWLWYIK

IFIMIVGGLIGLRIIFTVLNVINRVRQGYSPLSFQTLTHHQREPD

RPERIEEGGGEQDRDRSVRLVSGFLALAWDDLRSLCLFSFHRLRD

LVLIAARGVELLGHSSLKGLRLGWEALKLLGNLLSYWGQELKNSA

INLLDAVAIAVANWTDRVIKIGQRAGRAILNIPIRIRQGLERALL;

ZM233 Env

SEQ ID NO: 5

MRVRGIMRNWQQWWIWGSLGFWMLIICNVMGSLWVTVYYGVPVWR

EAKTTLFCASDAKAYETEAHSVWATHACVPTDPNPQEMVLENVTE

NFNMWKNDMVDQMHEDVISIWDQSLKPCVKLTPLCVILDCSTYNN

THNISKEMKICSFNMTTELRDKKRKVNVLFYKLDLVPLINSSNIT

NYRLISCNTSTITQACPKVSFDPIPIHYCAPAGYAILKCNNKTFN

GTGPCNNVSTVQCTHGIKPVVSTQLLLNGSLAEEEIIIRFENLTD

NVKIIIVQLNETINITCTRPNNNTRKSIRIGPGQSFYATGEIVGN

IREAHCNISASKWNKTLERVRTKLKEHFPNKTIEFEPSSGGDLEI

TTHSFNCGGEFFYCNTSGLENSAINGILISNVILPCRIKQIINMW

QEVGRAMYAPPIAGNITCKSNITGLLLTRDGGENSSSTTETFRPI

GGDMKNNWRSELYKYKVVEIKPLGIAPTEAKRRVVEREKRAVGIG

AVFLGFLGAAGSTMGAASMTLTVQARQLLSGIVQQQSNLLKAIEA

QQHMLQLTVWGIKQLQARVLAIERYLKDQQLLGLWGCSGKLICIT

NVPWNASWSNKSKNDIWDNMTWMQWDREISNHTDTIYRLLEDSQN

QQEKNEKDLLALDSWKNLWNWFSITKWLWYIKIFIMIVGGLIGLR

IIFAVLSIVNRVRQGYSPLSFQTLTPNPRGPDRLGGIEEEGGEQD

KNKSRRLVTGFLPVVWDDLRSLCLFSYHLLRDFILIVARTVELLG

RRGWEALKYLGGLVQYWGLELKKSTISLLDTIAIVVAEGTDRIIE

VLQRIGRAIYNIPRRIRQGFETALL;

BG505-ZM233V1V2 chimeric SOSIP

SEQ ID NO: 6

MDAMKRGLCCVLLLCGAVFVSPSQEIHARFRRGARAENLWVTVYY

GVPVWKDAETTLFCASDAKAYETEKHNVWATHACVPTDPNPQEIH

LENVTEEFNMWKNNMVEQMHTDIISLWDQSLKPCVKLTPLCVTLD

CSTYNNTHNISKEMKICSFNMTTELRDKKRKVNVLFYKLDLVPLI

NSSNTTNYRLISCNTSAITQACPKVSFEPIPIHYCAPAGFAILKC

KDKKFNGTGPCPSVSTVQCTHGIKPVVSTQLLLNGSLAEEEVMIR

SENITNNAKNILVQFNTPVQINCTRPNNNTRKSIRIGPGQAFYAT

GDIIGDIRQAHCNVSKATWNETLGKVVKQLRKHFGNNTIIRFANS

SGGDLEVTTHSFNCGGEFFYCNTSGLENSTWISNTSVQGSNSTGS

NDSITLPCRIKQIINMWQRIGQAMYAPPIQGVIRCVSNITGLILT

RDGGSINSTTETFRPGGGDMRDNWRSELYKYKVVKIEPLGVAPTR

CKRRVVGRRRRRRAVGIGAVFLGFLGAAGSTMGAASMTLTVQARN

LLSGIVQQQSNLLRAPEAQQHLLKLTVWGIKQLQARVLAVERYLR

DQQLLGIWGCSGKLICCTNVPWNSSWSNRNLSEIWDNMTWLQWDK

EISNYTQIIYGLLEESQNQQEKNEQDLLALD;

ZM197-ZM233V1V2 chimeric SQSIPM

SEQ ID NO: 7

DAMKRGLCCVLLLCGAVFVSPSQEIHARFRRGARMEQLWVTVYYG

VPVWKEAKATLFCASDAKAYEKEVHNVWATHACVPTDPNPQEIPL

GNVTENFNMWKNDMADQMHEDIISLWDQSLKPCVKLTPLCVTLDC

STYNNTHNISKEMKICSFNMTTELRDKKRKVNVLFYKLDLVPLIN

SSNTTNYRLISCNTSTITQACPKVSFDPIPIHYCAPAGYAILKCN

NKTFNGTGPCHNVSTVQCTHGIKPVVSTQLLLNGSLAEEEIIIRS

ENLTDNIKTIIVHLNESVEIECVRPNNNTRKSVRIGPGQTFFATG

EIIGDIRQAHCDLSKSNWTTILKRIEKKLKEHFNNATIKFESSAG

GDLEITTHSFNCRGEFFYCNTSGLFNSSLLNDTDGTSNSTSNATI

TLPCRIKQIINMWQEVGRAMYASPIAGIITCKSNITGLLLTRDGG

NKSAGIETFRPGGGNMKDNWRSELYKYKVVEIKPLGIAPTSCKRR

VVERRRRRRAAGIGAVILGFLGAAGSTMGAASVMLTVQARQLLSG

IVQQQSNLLRAPEAQQHMLQLTVWGIKQLQTRVLAIERYLKDQQL

LGLWGCSGKLICCTAVPWNTSWSNKSKDEIWDNMTWMQWDREIDN

YTQVIYQLLEVSQNQQEKNENDLLALD;

CRF250-ZM233V1V2 SOSIP

SEQ ID NO: 8

MDAMKRGLCCVLLLCGAVFVSPSQEIHARFRRGARAEKLWVTVYY

GVPVWREADTTLFCASDAKGYDTEAHNVWATHACVPTDPRPQEMY

LENVTENFNMWKNSMVEQMHTDIISLWDESLKPCVKLTPLCVTLD

CSTYNNTHNISKEMKICSFNMTTELRDKKRKVNVLFYKLDLVPLI

NSSNITNYRLISCNTSAITQACPKVSFEPIPIHFCAPAGFAILKC

NEKHFNGKGPCKNVSTVQCTHGIKPVVSTQLLLNGSLAEEEVVIR

VENTIDNAKTIIVQLAKPVKINCTRPNNNTRKSIRIGPGQTFYAT

GDIIGNIRKAYCNVSKREWNNTLQQVAAQLSKSENNTKIVFEKHS

GGDLEVITHSFVCGGEFFYCNTSGLFNSTWHNSTWINSTTGSNGT

ESNDTITLQCEIKQFINMWQRVGRAMYAPPIPGVIRCESDITGLL

LTRDGPNSTQNETFRPGGGDMRDNWRSELYKYKVVQIEPLGVAPT

HCKRRVVERRRRRRAVGLGAVFFGFLGAAGSTMGAASITLTVQAR

QLLSGIVQQQSNWLKAPEAQQHLLRLTVWGIKQLQARVLALERYL

KDQQLLGIWGCSGKLICCITVPWNSSWSNKNYTDIWDNMTWLQWD

REISNYTDEIYRLIEQSQNQQEKNEQDLLALD;

ZM233V1V2

SEQ ID NO: 9

DCSTYNNTHNISKEMKICSFNMTTELRDKKRKVNVLFYKLDLVPL

INSSNTTNYRLIS;

-continued

SEQ ID NO: 10

I-C-X$_1$-F-N-X$_2$-X$_3$-X$_4$-X$_5$-X$_6$-X$_7$-X$_8$-X$_9$-X$_{10}$-

X$_{11}$-X$_{12}$-V-N-V-L;

wherein X$_1$ comprises S, T, N, or F;

X$_2$ comprises I, V, T, Q, of M;

X$_3$ comprises S or T;

X$_4$ comprises S or T;

X$_5$ comprises S, E, or G;

-continued

X$_6$ comprises I, L, or V;

X$_7$ comprises K or R;

X$_8$ comprises G or D;

X$_9$ comprises K, R, E, or Q;

X$_{10}$ comprises K, R, E, or Q;

X$_{11}$ comprises K, R, E, or Q;

and X$_{12}$ comprises K, E, or Q.

SEQ ID NO: 11

ICSFNMTTELRDKKRKVNVL

---

What is claimed is:

1. An engineered or non-naturally occurring HIV Env polypeptide, wherein a) the engineered or non-naturally occurring HIV Env polypeptide is missing glycan sequons at N156 and N130 and has one or more basic residues at positions 168 to 171, wherein the HIV Env polypeptide; or b) the engineered or non-naturally occurring HIV Env polypeptide is an engineered or non-naturally occurring ZM233 HIV Env polypeptide missing glycan sequons at N156 and N130, wherein the HIV Env polypeptide positions correspond to the HXB2 reference (SEQ ID NO: 1).

2. The engineered or non-naturally occurring HIV Env polypeptide of claim 1, which binds to an HIV broadly neutralizing antibody (bnAb) directed to the V2 apex region of HIV envelope.

3. The engineered or non-naturally occurring HIV ENV polypeptide of claim 1, which is a chimeric HIV Env polypeptide comprising an HIV Env polypeptide backbone and the V1V2 region of the ZM233 HIV Env polypeptide.

4. The engineered or non-naturally occurring HIV Env polypeptide of claim 3, wherein the V1V2 region of the ZM233 HIV Env polypeptide comprises the amino acid sequence of SEQ ID NO: 9.

5. The engineered or non-naturally occurring HIV Env polypeptide of claim 3, wherein the HIV Env polypeptide backbone comprises a BG505, ZM197, or CFR250 backbone.

6. The engineered or non-naturally occurring HIV Env polypeptide of claim 1, which is a chimeric HIV Env polypeptide comprising an HIV Env polypeptide backbone and the amino acid residues of the ZM233 HIV Env polypeptide corresponding to positions about 131 to about 196.

7. The engineered or non-naturally occurring HIV Env polypeptide of claim 6, wherein the HIV Env polypeptide backbone comprises a BG505, ZM197, or CFR250 backbone.

8. The engineered or non-naturally occurring HIV Env polypeptide of claim 1, which comprises a complex of gp120 and gp41 or a stabilized trimer, optionally wherein the trimer is a SOSIP, NFL, or UFO trimer.

9. The engineered or non-naturally occurring HIV Env polypeptide of claim 1, which comprises a V2 apex epitope of ZM233 Env.

10. The HIV Env polypeptide of claim 9, (a) which comprises basic amino acid substitutions at positions 168 to 171, wherein the HIV Env polypeptide positions correspond to the HXB2 reference, (b) wherein the V2 apex region of positions 156 to 175 comprises one glycan and four consecutive basic amino acids, or (c) wherein the amino acid sequence of ICSFNMTTELRDKKRKVNVL (SEQ ID NO: 11) at positions 156 to 175.

11. The engineered or non-naturally occurring HIV Env polypeptide of claim 1 comprising the amino acid sequence of I-C-$X_1$-F-N-$X_2$-$X_3$-$X_4$-$X_5$-$X_6$-$X_7$-$X_8$-$X_9$-$X_{10}$-$X_{11}$-$X_{12}$-V-N-V-L (SEQ ID NO: 10) at positions 156 to 175, wherein $X_1$ comprises S, T, N, or F; $X_2$ comprises I, V, T, Q, or M; $X_3$ comprises S or T; $X_4$ comprises S or T; $X_5$ comprises S, E, or G; $X_6$ comprises I, L, or V; $X_7$ comprises K or R; $X_8$ comprises G or D; $X_9$ comprises K, R, E, or Q; $X_{10}$ comprises K, R, E, or Q; $X_{11}$ comprises K, R, E, or Q; and $X_{12}$ comprises K, E, or Q.

12. The engineered or non-naturally occurring HIV Env polypeptide of claim 11, wherein at least three of X9, X10, X11, and X12 comprise basic amino acid residues, all of X9, X10, X11, and X12 comprise basic amino acid residues, or X9, X10, X11, and X12 comprise K.

13. A nucleic acid molecule encoding the engineered or non-naturally occurring HIV Env polypeptide of claim 1.

14. A vector comprising a regulatory element operable in a eukaryotic cell operably linked to the nucleic acid molecule of claim 13.

15. The vector of claim 14, wherein the vector comprises AAV.

16. A method of eliciting an immune response or stimulating of a broadly neutralizing HIV antibody (bnAb) in a mammal comprising administering a) at least one engineered or non-naturally occurring HIV Env polypeptide of claim 1;

b) a nucleic acid molecule encoding at least one engineered or non-naturally occurring HIV Env polypeptide of claim 1; or c) a vector comprising a nucleic acid molecule encoding at least one engineered or non-naturally occurring HIV Env polypeptide of claim 1.

17. The method of claim 16, wherein the engineered or non-naturally occurring HIV Env polypeptide comprises a V2 apex epitope of ZM233 trimer.

18. A chimeric HIV Env polypeptide comprising an HIV Env polypeptide backbone and a) the V1V2 region of the ZM233 HIV Env polypeptide; or b) the amino acid residues of the ZM233 HIV Env polypeptide corresponding to positions about 131 to about 196, wherein the HIV Env polypeptide positions correspond to the HXB2 reference.

19. An HIV Env polypeptide comprising the amino acid sequence of SEQ ID NO: 6, 7, or 8.

* * * * *

SEQUENCE LISTING

<160> NUMBER OF SEQ ID NOS: 11

<210> SEQ ID NO 1
<211> LENGTH: 856
<212> TYPE: PRT
<213> ORGANISM: Human immunodeficiency virus
<220> FEATURE:
<223> OTHER INFORMATION: HIV HXB2 Env

<400> SEQUENCE: 1

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
            275                 280                 285
```

-continued

```
Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
                355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
                420                 425                 430

Ala Met Tyr Ala Pro Pro Ile Ser Gly Gln Ile Arg Cys Ser Ser Asn
                435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
                500                 505                 510

Val Gly Ile Gly Ala Leu Phe Leu Gly Phe Leu Gly Ala Ala Gly Ser
                515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
                580                 585                 590

Leu Gly Ile Trp Gly Cys Ser Gly Lys Leu Ile Cys Thr Thr Ala Val
                595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
                660                 665                 670

Phe Asn Ile Thr Asn Trp Leu Trp Tyr Ile Lys Leu Phe Ile Met Ile
                675                 680                 685

Val Gly Gly Leu Val Gly Leu Arg Ile Val Phe Ala Val Leu Ser Ile
    690                 695                 700
```

-continued

```
Val Asn Arg Val Arg Gln Gly Tyr Ser Pro Leu Ser Phe Gln Thr His
705             710                 715                 720

Leu Pro Thr Pro Arg Gly Pro Asp Arg Pro Glu Gly Ile Glu Glu Glu
                725             730                 735

Gly Gly Glu Arg Asp Arg Asp Arg Ser Ile Arg Leu Val Asn Gly Ser
            740             745                 750

Leu Ala Leu Ile Trp Asp Asp Leu Arg Ser Leu Cys Leu Phe Ser Tyr
            755             760             765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
                820                 825                 830

Val Gln Gly Ala Cys Arg Ala Ile Arg His Ile Pro Arg Arg Ile Arg
            835                 840                 845

Gln Gly Leu Glu Arg Ile Leu Leu
        850                 855

<210> SEQ ID NO 2
<211> LENGTH: 860
<212> TYPE: PRT
<213> ORGANISM: Human immunodeficiency virus
<220> FEATURE:
<223> OTHER INFORMATION: HIV HXB2 Env

<400> SEQUENCE: 2

Met Arg Val Met Gly Ile Gln Arg Asn Cys Gln His Leu Phe Arg Trp
1               5                   10                  15

Gly Thr Met Ile Leu Gly Met Ile Ile Ile Cys Ser Ala Ala Glu Asn
                20                  25                  30

Leu Trp Val Thr Val Tyr Tyr Gly Val Pro Val Trp Lys Asp Ala Glu
            35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
                100                 105                 110

Gln Ser Leu Lys Pro Cys Val Lys Leu Thr Pro Leu Cys Val Thr Leu
            115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
                180                 185                 190

Ile Asn Cys Asn Thr Ser Ala Ile Thr Gln Ala Cys Pro Lys Val Ser
            195                 200                 205
```

-continued

```
Phe Glu Pro Ile Pro Ile His Tyr Cys Ala Pro Ala Gly Phe Ala Ile
    210             215                 220

Leu Lys Cys Lys Asp Lys Lys Phe Asn Gly Thr Gly Pro Cys Pro Ser
225             230                 235                 240

Val Ser Thr Val Gln Cys Thr His Gly Ile Lys Pro Val Val Ser Thr
            245                 250                 255

Gln Leu Leu Leu Asn Gly Ser Leu Ala Glu Glu Glu Val Met Ile Arg
            260                 265                 270

Ser Glu Asn Ile Thr Asn Asn Ala Lys Asn Ile Leu Val Gln Phe Asn
            275                 280                 285

Thr Pro Val Gln Ile Asn Cys Thr Arg Pro Asn Asn Asn Thr Arg Lys
    290                 295                 300

Ser Ile Arg Ile Gly Pro Gly Gln Ala Phe Tyr Ala Thr Gly Asp Ile
305                 310                 315                 320

Ile Gly Asp Ile Arg Gln Ala His Cys Thr Val Ser Lys Ala Thr Trp
                325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
            355                 360                 365

Val Thr Thr His Ser Phe Asn Cys Gly Gly Glu Phe Phe Tyr Cys Asn
    370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
                405                 410                 415

Ile Lys Gln Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly
            435                 440                 445

Leu Ile Leu Thr Arg Asp Gly Gly Ser Thr Asn Ser Thr Thr Glu Thr
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Arg Ala Lys Arg Arg Val Val Gly Arg Glu Lys Arg Ala Val Gly Ile
            500                 505                 510

Gly Ala Val Phe Leu Gly Phe Leu Gly Ala Ala Gly Ser Thr Met Gly
            515                 520                 525

Ala Ala Ser Met Thr Leu Thr Val Gln Ala Arg Asn Leu Leu Ser Gly
    530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Asn Val Pro Trp Asn
            595                 600                 605

Ser Ser Trp Ser Asn Arg Asn Leu Ser Glu Ile Trp Asp Asn Met Thr
    610                 615                 620

Trp Leu Gln Trp Asp Lys Glu Ile Ser Asn Tyr Thr Gln Ile Ile Tyr
```

-continued

| 625 | | | 630 | | | 635 | | | 640 |

Gly Leu Leu Glu Glu Ser Gln Asn Gln Gln Glu Lys Asn Glu Gln Asp
                  645                   650               655

Leu Leu Ala Leu Asp Lys Trp Ala Ser Leu Trp Asn Trp Phe Asp Ile
             660                 665               670

Ser Asn Trp Leu Trp Tyr Ile Lys Ile Phe Ile Met Ile Val Gly Gly
          675                 680               685

Leu Ile Gly Leu Arg Ile Val Phe Ala Val Leu Ser Val Ile His Arg
          690                 695               700

Val Arg Gln Gly Tyr Ser Pro Leu Ser Phe Gln Thr His Thr Pro Asn
705                  710                 715               720

Pro Arg Gly Leu Asp Arg Pro Glu Arg Ile Glu Glu Glu Asp Gly Glu
             725                 730               735

Gln Asp Arg Gly Arg Ser Thr Arg Leu Val Ser Gly Phe Leu Ala Leu
             740                 745               750

Ala Trp Asp Asp Leu Arg Ser Leu Cys Leu Phe Cys Tyr His Arg Leu
          755                 760               765

Arg Asp Phe Ile Leu Ile Ala Ala Arg Ile Val Glu Leu Leu Gly His
          770                 775               780

Ser Ser Leu Lys Gly Leu Arg Leu Gly Trp Glu Gly Leu Lys Tyr Leu
785                  790                 795               800

Trp Asn Leu Leu Ala Tyr Trp Gly Arg Glu Leu Lys Ile Ser Ala Ile
             805                 810               815

Asn Leu Phe Asp Thr Ile Ala Ile Ala Val Ala Glu Trp Thr Asp Arg
             820                 825               830

Val Ile Glu Ile Gly Gln Arg Leu Cys Arg Ala Phe Leu His Ile Pro
          835                 840               845

Arg Arg Ile Arg Gln Gly Leu Glu Arg Ala Leu Leu
          850                 855               860

<210> SEQ ID NO 3
<211> LENGTH: 840
<212> TYPE: PRT
<213> ORGANISM: Human immunodeficiency virus
<220> FEATURE:
<223> OTHER INFORMATION: HIV ZM197 Env

<400> SEQUENCE: 3

Met Arg Val Met Gly Ile Leu Arg Asn Trp Gln Gln Trp Trp Ile Trp
1              5                 10               15

Gly Ile Leu Gly Phe Trp Met Leu Met Ile Cys Asn Met Glu Gln Leu
          20                 25               30

Trp Val Thr Val Tyr Tyr Gly Val Pro Val Trp Lys Glu Ala Lys Ala
          35                 40               45

Thr Leu Phe Cys Ala Ser Asp Ala Lys Ala Tyr Glu Lys Glu Val His
        50                 55               60

Asn Val Trp Ala Thr His Ala Cys Val Pro Thr Asp Pro Asn Pro Gln
65                  70                 75               80

Glu Ile Pro Leu Gly Asn Val Thr Glu Asn Phe Asn Met Trp Lys Asn
             85                 90               95

Asp Met Ala Asp Gln Met His Glu Asp Ile Ile Ser Leu Trp Asp Gln
             100                 105               110

Ser Leu Lys Pro Cys Val Lys Leu Thr Pro Leu Cys Val Thr Leu Asn
          115                 120               125

Cys Ser Asp Ala Thr Ser Asn Thr Thr Lys Asn Ala Thr Asn Thr Asn

```
        130              135                 140

Thr Thr Ser Thr Asp Asn Arg Asn Ala Thr Ser Asn Asp Thr Glu Met
145              150                 155              160

Lys Gly Glu Ile Lys Asp Cys Thr Phe Asn Ile Thr Thr Glu Val Arg
            165              170              175

Asp Arg Lys Thr Lys Gln Arg Ala Leu Phe Tyr Lys Leu Asp Val Val
            180              185              190

Pro Leu Glu Glu Glu Lys Asn Ser Ser Ser Lys Asn Ser Ser Tyr Lys
            195              200              205

Glu Tyr Arg Leu Ile Ser Cys Asn Thr Ser Thr Ile Thr Gln Ala Cys
            210              215              220

Pro Lys Val Ser Phe Asp Pro Ile Pro Ile His Tyr Cys Ala Pro Ala
225              230              235              240

Gly Tyr Ala Ile Leu Lys Cys Asn Asn Lys Thr Phe Asn Gly Thr Gly
            245              250              255

Pro Cys His Asn Val Ser Thr Val Gln Cys Thr His Gly Ile Lys Pro
            260              265              270

Val Val Ser Thr Gln Leu Leu Leu Asn Gly Ser Leu Ala Glu Glu Glu
            275              280              285

Ile Ile Ile Arg Ser Glu Asn Leu Thr Asp Asn Thr Lys Thr Ile Ile
            290              295              300

Val His Leu Asn Glu Ser Val Glu Ile Glu Cys Val Arg Pro Asn Asn
305              310              315              320

Asn Thr Arg Lys Ser Val Arg Ile Gly Pro Gly Gln Thr Phe Phe Ala
            325              330              335

Thr Gly Glu Ile Ile Gly Asp Ile Arg Gln Ala His Cys Asp Leu Ser
            340              345              350

Lys Ser Asn Trp Thr Thr Thr Leu Lys Arg Ile Glu Lys Lys Leu Lys
            355              360              365

Glu His Phe Asn Asn Ala Thr Ile Lys Phe Glu Ser Ser Ala Gly Gly
            370              375              380

Asp Leu Glu Ile Thr Thr His Ser Phe Asn Cys Arg Gly Glu Phe Phe
385              390              395              400

Tyr Cys Asn Thr Ser Gly Leu Phe Asn Ser Ser Leu Leu Asn Asp Thr
            405              410              415

Asp Gly Thr Ser Asn Ser Thr Ser Asn Ala Thr Ile Thr Leu Pro Cys
            420              425              430

Arg Ile Lys Gln Ile Ile Asn Met Trp Gln Glu Val Gly Arg Ala Met
            435              440              445

Tyr Ala Ser Pro Ile Ala Gly Ile Ile Thr Cys Lys Ser Asn Ile Thr
            450              455              460

Gly Leu Leu Leu Thr Arg Asp Gly Gly Asn Lys Ser Ala Gly Ile Glu
465              470              475              480

Thr Phe Arg Pro Gly Gly Gly Asn Met Lys Asp Asn Trp Arg Ser Glu
            485              490              495

Leu Tyr Lys Tyr Lys Val Val Glu Ile Lys Pro Leu Gly Ile Ala Pro
            500              505              510

Thr Ser Ala Lys Arg Arg Val Val Glu Arg Glu Lys Arg Ala Ala Gly
            515              520              525

Ile Gly Ala Val Ile Leu Gly Phe Leu Gly Ala Ala Gly Ser Thr Met
            530              535              540

Gly Ala Ala Ser Val Met Leu Thr Val Gln Ala Arg Gln Leu Leu Ser
545              550              555              560
```

-continued

```
Gly Ile Val Gln Gln Gln Ser Asn Leu Leu Arg Ala Ile Glu Ala Gln
             565                 570                 575

Gln His Met Leu Gln Leu Thr Val Trp Gly Ile Lys Gln Leu Gln Thr
             580                 585                 590

Arg Val Leu Ala Ile Glu Arg Tyr Leu Lys Asp Gln Gln Leu Leu Gly
             595                 600                 605

Leu Trp Gly Cys Ser Gly Lys Leu Ile Cys Thr Thr Ala Val Pro Trp
         610                 615                 620

Asn Thr Ser Trp Ser Asn Lys Ser Lys Asp Glu Ile Trp Asp Asn Met
625                 630                 635                 640

Thr Trp Met Gln Trp Asp Arg Glu Ile Asp Asn Tyr Thr Gln Val Ile
             645                 650                 655

Tyr Gln Leu Leu Glu Val Ser Gln Asn Gln Gln Glu Lys Asn Glu Asn
             660                 665                 670

Asp Leu Leu Ala Leu Asp Lys Trp Asn Ser Leu Trp Ser Trp Phe Asp
             675                 680                 685

Ile Thr Lys Trp Leu Trp Tyr Ile Lys Ile Phe Ile Met Ile Val Gly
         690                 695                 700

Gly Leu Ile Gly Leu Arg Ile Ile Phe Ala Val Leu Ser Val Val Asn
705                 710                 715                 720

Arg Val Arg Gln Gly Tyr Ser Pro Leu Ser Phe Gln Thr Leu Ile Pro
             725                 730                 735

Asn Pro Arg Gly Pro Asp Arg Pro Gly Gly Ile Glu Glu Glu Gly Gly
             740                 745                 750

Glu Gln Asp Lys Asn Arg Ser Thr Arg Leu Val Ser Gly Phe Leu Ala
             755                 760                 765

Leu Val Trp Asp Asp Leu Arg Ser Leu Cys Leu Phe Ser Tyr His Arg
         770                 775                 780

Leu Arg Asp Phe Ile Leu Ile Ala Ala Arg Ala Val Glu Leu Leu Gly
785                 790                 795                 800

Arg Ser Ser Leu Glu Gly Leu Gln Trp Gly Trp Glu Thr Leu Lys Tyr
             805                 810                 815

Leu Arg Asn Leu Val Gln Tyr Trp Gly Leu Glu Leu Lys Gln Ser Ala
             820                 825                 830

Ile Asn Leu Leu Asp Thr Ile Ala
         835                 840

<210> SEQ ID NO 4
<211> LENGTH: 855
<212> TYPE: PRT
<213> ORGANISM: Human immunodeficiency virus
<220> FEATURE:
<223> OTHER INFORMATION: HIV CRF250 Env

<400> SEQUENCE: 4

Met Arg Val Met Gly Ile Gln Arg Asn Tyr Pro Pro Leu Trp Arg Trp
1               5                   10                  15

Gly Thr Met Ile Phe Trp Met Met Leu Cys Ser Ala Glu Lys Leu
             20                  25                  30

Trp Val Thr Val Tyr Tyr Gly Val Pro Val Trp Arg Glu Ala Asp Thr
             35                  40                  45

Thr Leu Phe Cys Ala Ser Asp Ala Lys Gly Tyr Asp Thr Glu Ala His
         50                  55                  60

Asn Val Trp Ala Thr His Ala Cys Val Pro Thr Asp Pro Arg Pro Gln
65                  70                  75                  80
```

-continued

```
Glu Met Tyr Leu Glu Asn Val Thr Glu Asn Phe Asn Met Trp Lys Asn
                85                  90                  95

Ser Met Val Glu Gln Met His Thr Asp Ile Ile Ser Leu Trp Asp Glu
               100             105             110

Ser Leu Lys Pro Cys Val Lys Leu Thr Pro Leu Cys Val Thr Leu Asp
               115             120             125

Cys Gln Ala Phe Asn Ser Ser Ser His Thr Asn Ser Ser Ile Ala Met
           130             135             140

Gln Glu Met Lys Asn Cys Ser Phe Asn Val Thr Thr Glu Leu Arg Asp
145             150             155             160

Lys Lys Lys Lys Glu Tyr Ser Phe Phe Tyr Lys Thr Asp Ile Glu Gln
               165             170             175

Ile Asn Lys Asn Gly Arg Gln Tyr Arg Leu Ile Asn Cys Asn Thr Ser
           180             185             190

Ala Ile Thr Gln Ala Cys Pro Lys Val Ser Phe Glu Pro Ile Pro Ile
           195             200             205

His Phe Cys Ala Pro Ala Gly Phe Ala Ile Leu Lys Cys Asn Glu Lys
       210             215             220

His Phe Asn Gly Lys Gly Pro Cys Lys Asn Val Ser Thr Val Gln Cys
225             230             235             240

Thr His Gly Ile Lys Pro Val Val Ser Thr Gln Leu Leu Leu Asn Gly
           245             250             255

Ser Leu Ala Glu Glu Glu Val Val Ile Arg Val Glu Asn Thr Ile Asp
           260             265             270

Asn Ala Lys Thr Ile Ile Val Gln Leu Ala Lys Pro Val Lys Ile Asn
           275             280             285

Cys Thr Arg Pro Asn Asn Asn Thr Arg Lys Ser Ile Arg Ile Gly Pro
       290             295             300

Gly Gln Thr Phe Tyr Ala Thr Gly Asp Ile Ile Gly Asn Ile Arg Lys
305             310             315             320

Ala Tyr Cys Asn Val Ser Lys Arg Glu Trp Asn Asn Thr Leu Gln Gln
               325             330             335

Val Ala Ala Gln Leu Ser Lys Ser Phe Asn Asn Thr Lys Ile Val Phe
           340             345             350

Glu Lys His Ser Gly Gly Asp Leu Glu Val Ile Thr His Ser Phe Val
           355             360             365

Cys Gly Gly Glu Phe Phe Tyr Cys Asn Thr Ser Gly Leu Phe Asn Ser
       370             375             380

Thr Trp His Asn Ser Thr Trp Thr Asn Ser Thr Thr Gly Ser Asn Gly
385             390             395             400

Thr Glu Ser Asn Asp Thr Ile Thr Leu Gln Cys Glu Ile Lys Gln Phe
           405             410             415

Ile Asn Met Trp Gln Arg Val Gly Arg Ala Met Tyr Ala Pro Pro Ile
           420             425             430

Pro Gly Val Ile Arg Cys Glu Ser Asp Ile Thr Gly Leu Leu Leu Thr
           435             440             445

Arg Asp Gly Pro Asn Ser Thr Gln Asn Glu Thr Phe Arg Pro Gly Gly
       450             455             460

Gly Asp Met Arg Asp Asn Trp Arg Ser Glu Leu Tyr Lys Tyr Lys Val
465             470             475             480

Val Gln Ile Glu Pro Leu Gly Val Ala Pro Thr His Ala Lys Arg Arg
               485             490             495
```

-continued

```
Val Val Glu Arg Glu Lys Arg Ala Val Gly Leu Gly Ala Val Phe Phe
            500                 505                 510

Gly Phe Leu Gly Ala Ala Gly Ser Thr Met Gly Ala Ala Ser Ile Thr
            515                 520                 525

Leu Thr Val Gln Ala Arg Gln Leu Leu Ser Gly Ile Val Gln Gln Gln
            530                 535                 540

Ser Asn Trp Leu Lys Ala Ile Glu Ala Gln Gln His Leu Leu Arg Leu
545                 550                 555                 560

Thr Val Trp Gly Ile Lys Gln Leu Gln Ala Arg Val Leu Ala Leu Glu
            565                 570                 575

Arg Tyr Leu Lys Asp Gln Gln Leu Leu Gly Ile Trp Gly Cys Ser Gly
            580                 585                 590

Lys Leu Ile Cys Thr Thr Thr Val Pro Trp Asn Ser Ser Trp Ser Asn
            595                 600                 605

Lys Asn Tyr Thr Asp Ile Trp Asp Asn Met Thr Trp Leu Gln Trp Asp
            610                 615                 620

Arg Glu Ile Ser Asn Tyr Thr Asp Glu Ile Tyr Arg Leu Ile Glu Gln
625                 630                 635                 640

Ser Gln Asn Gln Gln Glu Lys Asn Glu Gln Asp Leu Leu Ala Leu Asp
            645                 650                 655

Lys Trp Ala Ser Leu Trp Asn Trp Phe Asp Ile Thr Asn Trp Leu Trp
            660                 665                 670

Tyr Ile Lys Ile Phe Ile Met Ile Val Gly Gly Leu Ile Gly Leu Arg
            675                 680                 685

Ile Ile Phe Thr Val Leu Asn Val Ile Asn Arg Val Arg Gln Gly Tyr
            690                 695                 700

Ser Pro Leu Ser Phe Gln Thr Leu Thr His His Gln Arg Glu Pro Asp
705                 710                 715                 720

Arg Pro Glu Arg Ile Glu Glu Gly Gly Gly Glu Gln Asp Arg Asp Arg
            725                 730                 735

Ser Val Arg Leu Val Ser Gly Phe Leu Ala Leu Ala Trp Asp Asp Leu
            740                 745                 750

Arg Ser Leu Cys Leu Phe Ser Phe His Arg Leu Arg Asp Leu Val Leu
            755                 760                 765

Ile Ala Ala Arg Gly Val Glu Leu Leu Gly His Ser Ser Leu Lys Gly
            770                 775                 780

Leu Arg Leu Gly Trp Glu Ala Leu Lys Leu Leu Gly Asn Leu Leu Ser
785                 790                 795                 800

Tyr Trp Gly Gln Glu Leu Lys Asn Ser Ala Ile Asn Leu Leu Asp Ala
            805                 810                 815

Val Ala Ile Ala Val Ala Asn Trp Thr Asp Arg Val Ile Lys Ile Gly
            820                 825                 830

Gln Arg Ala Gly Arg Ala Ile Leu Asn Ile Pro Ile Arg Ile Arg Gln
            835                 840                 845

Gly Leu Glu Arg Ala Leu Leu
    850                 855
```

```
<210> SEQ ID NO 5
<211> LENGTH: 835
<212> TYPE: PRT
<213> ORGANISM: Human immunodeficiency virus
<220> FEATURE:
<223> OTHER INFORMATION: HIV ZM233 Env

<400> SEQUENCE: 5
```

-continued

```
Met Arg Val Arg Gly Ile Met Arg Asn Trp Gln Gln Trp Trp Ile Trp
1               5                   10                  15

Gly Ser Leu Gly Phe Trp Met Leu Ile Ile Cys Asn Val Met Gly Ser
            20                  25                  30

Leu Trp Val Thr Val Tyr Tyr Gly Val Pro Val Trp Arg Glu Ala Lys
        35                  40                  45

Thr Thr Leu Phe Cys Ala Ser Asp Ala Lys Ala Tyr Glu Thr Glu Ala
    50                  55                  60

His Ser Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Val Ile Ser Ile Trp Asp
            100                 105                 110

Gln Ser Leu Lys Pro Cys Val Lys Leu Thr Pro Leu Cys Val Thr Leu
        115                 120                 125

Asp Cys Ser Thr Tyr Asn Asn Thr His Asn Ile Ser Lys Glu Met Lys
    130                 135                 140

Ile Cys Ser Phe Asn Met Thr Thr Glu Leu Arg Asp Lys Lys Arg Lys
145                 150                 155                 160

Val Asn Val Leu Phe Tyr Lys Leu Asp Leu Val Pro Leu Thr Asn Ser
                165                 170                 175

Ser Asn Thr Thr Asn Tyr Arg Leu Ile Ser Cys Asn Thr Ser Thr Ile
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
    210                 215                 220

Asn Gly Thr Gly Pro Cys Asn Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Glu Glu Ile Ile Ile Arg Phe Glu Asn Leu Thr Asp Asn Val
            260                 265                 270

Lys Ile Ile Ile Val Gln Leu Asn Glu Thr Ile Asn Ile Thr Cys Thr
        275                 280                 285

Arg Pro Asn Asn Asn Thr Arg Lys Ser Ile Arg Ile Gly Pro Gly Gln
    290                 295                 300

Ser Phe Tyr Ala Thr Gly Glu Ile Val Gly Asn Ile Arg Glu Ala His
305                 310                 315                 320

Cys Asn Ile Ser Ala Ser Lys Trp Asn Lys Thr Leu Glu Arg Val Arg
                325                 330                 335

Thr Lys Leu Lys Glu His Phe Pro Asn Lys Thr Ile Glu Phe Glu Pro
            340                 345                 350

Ser Ser Gly Gly Asp Leu Glu Ile Thr Thr His Ser Phe Asn Cys Gly
        355                 360                 365

Gly Glu Phe Phe Tyr Cys Asn Thr Ser Gly Leu Phe Asn Ser Ala Ile
    370                 375                 380

Asn Gly Thr Leu Thr Ser Asn Val Thr Leu Pro Cys Arg Ile Lys Gln
385                 390                 395                 400

Ile Ile Asn Met Trp Gln Glu Val Gly Arg Ala Met Tyr Ala Pro Pro
                405                 410                 415

Ile Ala Gly Asn Ile Thr Cys Lys Ser Asn Ile Thr Gly Leu Leu Leu
```

-continued

```
              420              425                430

Thr Arg Asp Gly Gly Glu Asn Ser Ser Ser Thr Thr Glu Thr Phe Arg
        435              440              445

Pro Thr Gly Gly Asp Met Lys Asn Asn Trp Arg Ser Glu Leu Tyr Lys
    450              455              460

Tyr Lys Val Val Glu Ile Lys Pro Leu Gly Ile Ala Pro Thr Glu Ala
465              470              475              480

Lys Arg Arg Val Val Glu Arg Glu Lys Arg Ala Val Gly Ile Gly Ala
            485              490              495

Val Phe Leu Gly Phe Leu Gly Ala Ala Gly Ser Thr Met Gly Ala Ala
        500              505              510

Ser Met Thr Leu Thr Val Gln Ala Arg Gln Leu Leu Ser Gly Ile Val
    515              520              525

Gln Gln Gln Ser Asn Leu Leu Lys Ala Ile Glu Ala Gln Gln His Met
    530              535              540

Leu Gln Leu Thr Val Trp Gly Ile Lys Gln Leu Gln Ala Arg Val Leu
545              550              555              560

Ala Ile Glu Arg Tyr Leu Lys Asp Gln Gln Leu Leu Gly Leu Trp Gly
            565              570              575

Cys Ser Gly Lys Leu Ile Cys Thr Thr Asn Val Pro Trp Asn Ala Ser
            580              585              590

Trp Ser Asn Lys Ser Lys Asn Asp Ile Trp Asp Asn Met Thr Trp Met
    595              600              605

Gln Trp Asp Arg Glu Ile Ser Asn His Thr Asp Thr Ile Tyr Arg Leu
    610              615              620

Leu Glu Asp Ser Gln Asn Gln Gln Glu Lys Asn Glu Lys Asp Leu Leu
625              630              635              640

Ala Leu Asp Ser Trp Lys Asn Leu Trp Asn Trp Phe Ser Ile Thr Lys
            645              650              655

Trp Leu Trp Tyr Ile Lys Ile Phe Ile Met Ile Val Gly Gly Leu Ile
            660              665              670

Gly Leu Arg Ile Ile Phe Ala Val Leu Ser Ile Val Asn Arg Val Arg
            675              680              685

Gln Gly Tyr Ser Pro Leu Ser Phe Gln Thr Leu Thr Pro Asn Pro Arg
    690              695              700

Gly Pro Asp Arg Leu Gly Gly Ile Glu Glu Glu Gly Gly Glu Gln Asp
705              710              715              720

Lys Asn Lys Ser Arg Arg Leu Val Thr Gly Phe Leu Pro Val Val Trp
            725              730              735

Asp Asp Leu Arg Ser Leu Cys Leu Phe Ser Tyr His Leu Leu Arg Asp
            740              745              750

Phe Ile Leu Ile Val Ala Arg Thr Val Glu Leu Leu Gly Arg Arg Gly
    755              760              765

Trp Glu Ala Leu Lys Tyr Leu Gly Gly Leu Val Gln Tyr Trp Gly Leu
    770              775              780

Glu Leu Lys Lys Ser Thr Ile Ser Leu Leu Asp Thr Ile Ala Ile Val
785              790              795              800

Val Ala Glu Gly Thr Asp Arg Ile Ile Glu Val Leu Gln Arg Ile Gly
            805              810              815

Arg Ala Ile Tyr Asn Ile Pro Arg Arg Ile Arg Gln Gly Phe Glu Thr
            820              825              830

Ala Leu Leu
        835
```

```
<210> SEQ ID NO 6
<211> LENGTH: 661
<212> TYPE: PRT
<213> ORGANISM: Artificial Sequence
<220> FEATURE:
<223> OTHER INFORMATION: BG505-ZM233V1V2 chimeric SOSIP

<400> SEQUENCE: 6

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Glu Asn Leu Trp Val Thr Val Tyr Tyr Gly Val Pro
        35                  40                  45

Val Trp Lys Asp Ala Glu Thr Thr Leu Phe Cys Ala Ser Asp Ala Lys
    50                  55                  60

Ala Tyr Glu Thr Glu Lys His Asn Val Trp Ala Thr His Ala Cys Val
65                  70                  75                  80

Pro Thr Asp Pro Asn Pro Gln Glu Ile His Leu Glu Asn Val Thr Glu
                85                  90                  95

Glu Phe Asn Met Trp Lys Asn Asn Met Val Glu Gln Met His Thr Asp
            100                 105                 110

Ile Ile Ser Leu Trp Asp Gln Ser Leu Lys Pro Cys Val Lys Leu Thr
            115                 120                 125

Pro Leu Cys Val Thr Leu Asp Cys Ser Thr Tyr Asn Asn Thr His Asn
        130                 135                 140

Ile Ser Lys Glu Met Lys Ile Cys Ser Phe Asn Met Thr Thr Glu Leu
145                 150                 155                 160

Arg Asp Lys Lys Arg Lys Val Asn Val Leu Phe Tyr Lys Leu Asp Leu
                165                 170                 175

Val Pro Leu Thr Asn Ser Ser Asn Thr Thr Asn Tyr Arg Leu Ile Ser
            180                 185                 190

Cys Asn Thr Ser Ala Ile Thr Gln Ala Cys Pro Lys Val Ser Phe Glu
            195                 200                 205

Pro Ile Pro Ile His Tyr Cys Ala Pro Ala Gly Phe Ala Ile Leu Lys
        210                 215                 220

Cys Lys Asp Lys Lys Phe Asn Gly Thr Gly Pro Cys Pro Ser Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Glu Val Met Ile Arg Ser Glu
            260                 265                 270

Asn Ile Thr Asn Asn Ala Lys Asn Ile Leu Val Gln Phe Asn Thr Pro
            275                 280                 285

Val Gln Ile Asn Cys Thr Arg Pro Asn Asn Asn Thr Arg Lys Ser Ile
    290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Val Ser Lys Ala Thr Trp Asn Glu
                325                 330                 335

Thr Leu Gly Lys Val Val Lys Gln Leu Arg Lys His Phe Gly Asn Asn
            340                 345                 350

Thr Ile Ile Arg Phe Ala Asn Ser Ser Gly Gly Asp Leu Glu Val Thr
            355                 360                 365
```

```
Thr His Ser Phe Asn Cys Gly Gly Glu Phe Phe Tyr Cys Asn Thr Ser
    370             375             380

Gly Leu Phe Asn Ser Thr Trp Ile Ser Asn Thr Ser Val Gln Gly Ser
385             390             395             400

Asn Ser Thr Gly Ser Asn Asp Ser Ile Thr Leu Pro Cys Arg Ile Lys
            405             410             415

Gln Ile Ile Asn Met Trp Gln Arg Ile Gly Gln Ala Met Tyr Ala Pro
            420             425             430

Pro Ile Gln Gly Val Ile Arg Cys Val Ser Asn Ile Thr Gly Leu Ile
            435             440             445

Leu Thr Arg Asp Gly Gly Ser Thr Asn Ser Thr Thr Glu Thr Phe Arg
    450             455             460

Pro Gly Gly Gly Asp Met Arg Asp Asn Trp Arg Ser Glu Leu Tyr Lys
465             470             475             480

Tyr Lys Val Val Lys Ile Glu Pro Leu Gly Val Ala Pro Thr Arg Cys
            485             490             495

Lys Arg Arg Val Val Gly Arg Arg Arg Arg Arg Ala Val Gly Ile
            500             505             510

Gly Ala Val Phe Leu Gly Phe Leu Gly Ala Ala Gly Ser Thr Met Gly
            515             520             525

Ala Ala Ser Met Thr Leu Thr Val Gln Ala Arg Asn Leu Leu Ser Gly
    530             535             540

Ile Val Gln Gln Gln Ser Asn Leu Leu Arg Ala Pro Glu Ala Gln Gln
545             550             555             560

His Leu Leu Lys Leu Thr Val Trp Gly Ile Lys Gln Leu Gln Ala Arg
            565             570             575

Val Leu Ala Val Glu Arg Tyr Leu Arg Asp Gln Gln Leu Leu Gly Ile
            580             585             590

Trp Gly Cys Ser Gly Lys Leu Ile Cys Cys Thr Asn Val Pro Trp Asn
            595             600             605

Ser Ser Trp Ser Asn Arg Asn Leu Ser Glu Ile Trp Asp Asn Met Thr
    610             615             620

Trp Leu Gln Trp Asp Lys Glu Ile Ser Asn Tyr Thr Gln Ile Ile Tyr
625             630             635             640

Gly Leu Leu Glu Glu Ser Gln Asn Gln Gln Glu Lys Asn Glu Gln Asp
            645             650             655

Leu Leu Ala Leu Asp
            660
```

```
<210> SEQ ID NO 7
<211> LENGTH: 658
<212> TYPE: PRT
<213> ORGANISM: Artificial Sequence
<220> FEATURE:
<223> OTHER INFORMATION: ZM197-ZM233V1V2 chimeric SOSIP

<400> SEQUENCE: 7

Met Asp Ala Met Lys Arg Gly Leu Cys Cys Val Leu Leu Leu Cys Gly
1               5               10              15

Ala Val Phe Val Ser Pro Ser Gln Glu Ile His Ala Arg Phe Arg Arg
            20              25              30

Gly Ala Arg Met Glu Gln Leu Trp Val Thr Val Tyr Tyr Gly Val Pro
        35              40              45

Val Trp Lys Glu Ala Lys Ala Thr Leu Phe Cys Ala Ser Asp Ala Lys
    50              55              60
```

-continued

```
Ala Tyr Glu Lys Glu Val His Asn Val Trp Ala Thr His Ala Cys Val
65                  70                  75                  80

Pro Thr Asp Pro Asn Pro Gln Glu Ile Pro Leu Gly Asn Val Thr Glu
                85                  90                  95

Asn Phe Asn Met Trp Lys Asn Asp Met Ala Asp Gln Met His Glu Asp
                100                 105                 110

Ile Ile Ser Leu Trp Asp Gln Ser Leu Lys Pro Cys Val Lys Leu Thr
                115                 120                 125

Pro Leu Cys Val Thr Leu Asp Cys Ser Thr Tyr Asn Asn Thr His Asn
        130                 135                 140

Ile Ser Lys Glu Met Lys Ile Cys Ser Phe Asn Met Thr Thr Glu Leu
145                 150                 155                 160

Arg Asp Lys Lys Arg Lys Val Asn Val Leu Phe Tyr Lys Leu Asp Leu
                165                 170                 175

Val Pro Leu Thr Asn Ser Ser Asn Thr Thr Asn Tyr Arg Leu Ile Ser
                180                 185                 190

Cys Asn Thr Ser Thr Ile Thr Gln Ala Cys Pro Lys Val Ser Phe Asp
                195                 200                 205

Pro Ile Pro Ile His Tyr Cys Ala Pro Ala Gly Tyr Ala Ile Leu Lys
        210                 215                 220

Cys Asn Asn Lys Thr Phe Asn Gly Thr Gly Pro Cys His Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Glu Ile Ile Ile Arg Ser Glu
                260                 265                 270

Asn Leu Thr Asp Asn Thr Lys Thr Ile Ile Val His Leu Asn Glu Ser
                275                 280                 285

Val Glu Ile Glu Cys Val Arg Pro Asn Asn Asn Thr Arg Lys Ser Val
        290                 295                 300

Arg Ile Gly Pro Gly Gln Thr Phe Phe Ala Thr Gly Glu Ile Ile Gly
305                 310                 315                 320

Asp Ile Arg Gln Ala His Cys Asp Leu Ser Lys Ser Asn Trp Thr Thr
                325                 330                 335

Thr Leu Lys Arg Ile Glu Lys Lys Leu Lys Glu His Phe Asn Asn Ala
                340                 345                 350

Thr Ile Lys Phe Glu Ser Ser Ala Gly Gly Asp Leu Glu Ile Thr Thr
                355                 360                 365

His Ser Phe Asn Cys Arg Gly Glu Phe Phe Tyr Cys Asn Thr Ser Gly
        370                 375                 380

Leu Phe Asn Ser Ser Leu Leu Asn Asp Thr Asp Gly Thr Ser Asn Ser
385                 390                 395                 400

Thr Ser Asn Ala Thr Ile Thr Leu Pro Cys Arg Ile Lys Gln Ile Ile
                405                 410                 415

Asn Met Trp Gln Glu Val Gly Arg Ala Met Tyr Ala Ser Pro Ile Ala
                420                 425                 430

Gly Ile Ile Thr Cys Lys Ser Asn Ile Thr Gly Leu Leu Leu Thr Arg
        435                 440                 445

Asp Gly Gly Asn Lys Ser Ala Gly Ile Glu Thr Phe Arg Pro Gly Gly
        450                 455                 460

Gly Asn Met Lys Asp Asn Trp Arg Ser Glu Leu Tyr Lys Tyr Lys Val
465                 470                 475                 480
```

-continued

```
Val Glu Ile Lys Pro Leu Gly Ile Ala Pro Thr Ser Cys Lys Arg Arg
              485             490             495

Val Val Glu Arg Arg Arg Arg Arg Ala Ala Gly Ile Gly Ala Val
          500             505             510

Ile Leu Gly Phe Leu Gly Ala Ala Gly Ser Thr Met Gly Ala Ala Ser
          515             520             525

Val Met Leu Thr Val Gln Ala Arg Gln Leu Leu Ser Gly Ile Val Gln
      530             535             540

Gln Gln Ser Asn Leu Leu Arg Ala Pro Glu Ala Gln Gln His Met Leu
545             550             555             560

Gln Leu Thr Val Trp Gly Ile Lys Gln Leu Gln Thr Arg Val Leu Ala
              565             570             575

Ile Glu Arg Tyr Leu Lys Asp Gln Gln Leu Leu Gly Leu Trp Gly Cys
              580             585             590

Ser Gly Lys Leu Ile Cys Cys Thr Ala Val Pro Trp Asn Thr Ser Trp
              595             600             605

Ser Asn Lys Ser Lys Asp Glu Ile Trp Asp Asn Met Thr Trp Met Gln
          610             615             620

Trp Asp Arg Glu Ile Asp Asn Tyr Thr Gln Val Ile Tyr Gln Leu Leu
625             630             635             640

Glu Val Ser Gln Asn Gln Gln Glu Lys Asn Glu Asn Asp Leu Leu Ala
              645             650             655

Leu Asp
```

```
<210> SEQ ID NO 8
<211> LENGTH: 662
<212> TYPE: PRT
<213> ORGANISM: Artificial Sequence
<220> FEATURE:
<223> OTHER INFORMATION: CRF250-ZM233V1V2 SOSIP

<400> SEQUENCE: 8

Met Asp Ala Met Lys Arg Gly Leu Cys Cys Val Leu Leu Leu Cys Gly
1               5               10              15

Ala Val Phe Val Ser Pro Ser Gln Glu Ile His Ala Arg Phe Arg Arg
              20              25              30

Gly Ala Arg Ala Glu Lys Leu Trp Val Thr Val Tyr Tyr Gly Val Pro
          35              40              45

Val Trp Arg Glu Ala Asp Thr Thr Leu Phe Cys Ala Ser Asp Ala Lys
      50              55              60

Gly Tyr Asp Thr Glu Ala His Asn Val Trp Ala Thr His Ala Cys Val
65              70              75              80

Pro Thr Asp Pro Arg Pro Gln Glu Met Tyr Leu Glu Asn Val Thr Glu
              85              90              95

Asn Phe Asn Met Trp Lys Asn Ser Met Val Glu Gln Met His Thr Asp
              100             105             110

Ile Ile Ser Leu Trp Asp Glu Ser Leu Lys Pro Cys Val Lys Leu Thr
          115             120             125

Pro Leu Cys Val Thr Leu Asp Cys Ser Thr Tyr Asn Asn Thr His Asn
      130             135             140

Ile Ser Lys Glu Met Lys Ile Cys Ser Phe Asn Met Thr Thr Glu Leu
145             150             155             160

Arg Asp Lys Lys Arg Lys Val Asn Val Leu Phe Tyr Lys Leu Asp Leu
              165             170             175

Val Pro Leu Thr Asn Ser Ser Asn Thr Thr Asn Tyr Arg Leu Ile Ser
```

-continued

```
            180              185              190

Cys Asn Thr Ser Ala Ile Thr Gln Ala Cys Pro Lys Val Ser Phe Glu
            195              200              205

Pro Ile Pro Ile His Phe Cys Ala Pro Ala Gly Phe Ala Ile Leu Lys
            210              215              220

Cys Asn Glu Lys His Phe Asn Gly Lys Gly Pro Cys Lys Asn Val Ser
225              230              235              240

Thr Val Gln Cys Thr His Gly Ile Lys Pro Val Val Ser Thr Gln Leu
            245              250              255

Leu Leu Asn Gly Ser Leu Ala Glu Glu Glu Val Val Ile Arg Val Glu
            260              265              270

Asn Thr Ile Asp Asn Ala Lys Thr Ile Ile Val Gln Leu Ala Lys Pro
            275              280              285

Val Lys Ile Asn Cys Thr Arg Pro Asn Asn Asn Thr Arg Lys Ser Ile
            290              295              300

Arg Ile Gly Pro Gly Gln Thr Phe Tyr Ala Thr Gly Asp Ile Ile Gly
305              310              315              320

Asn Ile Arg Lys Ala Tyr Cys Asn Val Ser Lys Arg Glu Trp Asn Asn
            325              330              335

Thr Leu Gln Gln Val Ala Ala Gln Leu Ser Lys Ser Phe Asn Asn Thr
            340              345              350

Lys Ile Val Phe Glu Lys His Ser Gly Gly Asp Leu Glu Val Ile Thr
            355              360              365

His Ser Phe Val Cys Gly Gly Glu Phe Phe Tyr Cys Asn Thr Ser Gly
            370              375              380

Leu Phe Asn Ser Thr Trp His Asn Ser Thr Trp Thr Asn Ser Thr Thr
385              390              395              400

Gly Ser Asn Gly Thr Glu Ser Asn Asp Thr Ile Thr Leu Gln Cys Glu
            405              410              415

Ile Lys Gln Phe Ile Asn Met Trp Gln Arg Val Gly Arg Ala Met Tyr
            420              425              430

Ala Pro Pro Ile Pro Gly Val Ile Arg Cys Glu Ser Asp Ile Thr Gly
            435              440              445

Leu Leu Leu Thr Arg Asp Gly Pro Asn Ser Thr Gln Asn Glu Thr Phe
            450              455              460

Arg Pro Gly Gly Gly Asp Met Arg Asp Asn Trp Arg Ser Glu Leu Tyr
465              470              475              480

Lys Tyr Lys Val Val Gln Ile Glu Pro Leu Gly Val Ala Pro Thr His
            485              490              495

Cys Lys Arg Arg Val Val Glu Arg Arg Arg Arg Arg Ala Val Gly
            500              505              510

Leu Gly Ala Val Phe Phe Gly Phe Leu Gly Ala Ala Gly Ser Thr Met
            515              520              525

Gly Ala Ala Ser Ile Thr Leu Thr Val Gln Ala Arg Gln Leu Leu Ser
            530              535              540

Gly Ile Val Gln Gln Gln Ser Asn Trp Leu Lys Ala Pro Glu Ala Gln
545              550              555              560

Gln His Leu Leu Arg Leu Thr Val Trp Gly Ile Lys Gln Leu Gln Ala
            565              570              575

Arg Val Leu Ala Leu Glu Arg Tyr Leu Lys Asp Gln Gln Leu Leu Gly
            580              585              590

Ile Trp Gly Cys Ser Gly Lys Leu Ile Cys Cys Thr Thr Val Pro Trp
            595              600              605
```

```
Asn Ser Ser Trp Ser Asn Lys Asn Tyr Thr Asp Ile Trp Asp Asn Met
    610             615             620

Thr Trp Leu Gln Trp Asp Arg Glu Ile Ser Asn Tyr Thr Asp Glu Ile
625             630             635             640

Tyr Arg Leu Ile Glu Gln Ser Gln Asn Gln Gln Glu Lys Asn Glu Gln
            645             650             655

Asp Leu Leu Ala Leu Asp
            660

<210> SEQ ID NO 9
<211> LENGTH: 58
<212> TYPE: PRT
<213> ORGANISM: Artificial Sequence
<220> FEATURE:
<223> OTHER INFORMATION: ZM233V1V2

<400> SEQUENCE: 9

Asp Cys Ser Thr Tyr Asn Asn Thr His Asn Ile Ser Lys Glu Met Lys
1               5               10              15

Ile Cys Ser Phe Asn Met Thr Thr Glu Leu Arg Asp Lys Lys Arg Lys
            20              25              30

Val Asn Val Leu Phe Tyr Lys Leu Asp Leu Val Pro Leu Thr Asn Ser
        35              40              45

Ser Asn Thr Thr Asn Tyr Arg Leu Ile Ser
    50              55

<210> SEQ ID NO 10
<211> LENGTH: 20
<212> TYPE: PRT
<213> ORGANISM: Artificial Sequence
<220> FEATURE:
<223> OTHER INFORMATION: Artificial Polypeptide
<220> FEATURE:
<221> NAME/KEY: MISC_FEATURE
<222> LOCATION: (3)..(3)
<223> OTHER INFORMATION: Xaa can be Ser, Thr, Asn, or Phe
<220> FEATURE:
<221> NAME/KEY: MISC_FEATURE
<222> LOCATION: (6)..(6)
<223> OTHER INFORMATION: Xaa can be Ile, Val, Thr, Gln, or Met
<220> FEATURE:
<221> NAME/KEY: MISC_FEATURE
<222> LOCATION: (7)..(7)
<223> OTHER INFORMATION: Xaa can be Ser or Thr
<220> FEATURE:
<221> NAME/KEY: MISC_FEATURE
<222> LOCATION: (8)..(8)
<223> OTHER INFORMATION: Xaa can be Ser or Thr
<220> FEATURE:
<221> NAME/KEY: MISC_FEATURE
<222> LOCATION: (9)..(9)
<223> OTHER INFORMATION: Xaa can be Ser, Glu, or Gly
<220> FEATURE:
<221> NAME/KEY: MISC_FEATURE
<222> LOCATION: (10)..(10)
<223> OTHER INFORMATION: Xaa can be Ile, Leu, or Val
<220> FEATURE:
<221> NAME/KEY: MISC_FEATURE
<222> LOCATION: (11)..(11)
<223> OTHER INFORMATION: Xaa can be Lys or Arg
<220> FEATURE:
<221> NAME/KEY: MISC_FEATURE
<222> LOCATION: (12)..(12)
<223> OTHER INFORMATION: Xaa can be Gly or Asp
<220> FEATURE:
<221> NAME/KEY: MISC_FEATURE
<222> LOCATION: (13)..(13)
<223> OTHER INFORMATION: Xaa can be Lys, Arg, Glu, or Gln
<220> FEATURE:
```

-continued

```
<221> NAME/KEY: MISC_FEATURE
<222> LOCATION: (14)..(14)
<223> OTHER INFORMATION: Xaa can be Lys, Arg, Glu, or Gln
<220> FEATURE:
<221> NAME/KEY: MISC_FEATURE
<222> LOCATION: (15)..(15)
<223> OTHER INFORMATION: Xaa can be Lys, Arg, Glu, or Gln
<220> FEATURE:
<221> NAME/KEY: MISC_FEATURE
<222> LOCATION: (16)..(16)
<223> OTHER INFORMATION: Xaa can be Lys, Glu, or Gln

<400> SEQUENCE: 10

Ile Cys Xaa Phe Asn Xaa Xaa Xaa Xaa Xaa Xaa Xaa Xaa Xaa Xaa Xaa
1               5                   10                  15

Val Asn Val Leu
            20

<210> SEQ ID NO 11
<211> LENGTH: 20
<212> TYPE: PRT
<213> ORGANISM: Artificial Sequence
<220> FEATURE:
<223> OTHER INFORMATION: Artificial Polypeptide

<400> SEQUENCE: 11

Ile Cys Ser Phe Asn Met Thr Thr Glu Leu Arg Asp Lys Lys Arg Lys
1               5                   10                  15

Val Asn Val Leu
            20
```